United States Patent
Wu et al.

(10) Patent No.: US 12,304,910 B2
(45) Date of Patent: May 20, 2025

(54) JANUS KINASE (JAK) FAMILY INHIBITOR, PREPARATION OF SAME, AND APPLICATIONS THEREOF

(71) Applicant: JIANGSU VCARE PHARMATECH CO., LTD., Jiangsu (CN)

(72) Inventors: Yong Wu, Jiangsu (CN); Yanchun Gong, Jiangsu (CN); Wenbin Zhou, Jiangsu (CN); Daan Qin, Jiangsu (CN); Ya Zhang, Jiangsu (CN); Yongqiang Liu, Jiangsu (CN)

(73) Assignee: JIANGSU VCARE PHARMATECH CO., LTD., Jiangsu (CN)

( * ) Notice: Subject to any disclaimer, the term of this patent is extended or adjusted under 35 U.S.C. 154(b) by 877 days.

(21) Appl. No.: 17/425,844

(22) PCT Filed: Jan. 19, 2020

(86) PCT No.: PCT/CN2020/072949
§ 371 (c)(1),
(2) Date: Jul. 26, 2021

(87) PCT Pub. No.: WO2020/156271
PCT Pub. Date: Aug. 6, 2020

(65) Prior Publication Data
US 2022/0177467 A1    Jun. 9, 2022

(30) Foreign Application Priority Data

Feb. 2, 2019   (CN) .................. 201910106479.X
Jan. 13, 2020  (CN) .................. 202010050671.4

(51) Int. Cl.
| | | |
|---|---|---|
| C07D 471/04 | (2006.01) |
| A61P 1/00 | (2006.01) |
| A61P 3/10 | (2006.01) |
| A61P 7/00 | (2006.01) |
| A61P 7/02 | (2006.01) |
| A61P 9/10 | (2006.01) |
| A61P 11/02 | (2006.01) |
| A61P 11/06 | (2006.01) |
| A61P 17/00 | (2006.01) |
| A61P 19/02 | (2006.01) |
| A61P 25/00 | (2006.01) |
| A61P 25/28 | (2006.01) |
| A61P 27/02 | (2006.01) |
| A61P 29/00 | (2006.01) |
| A61P 31/12 | (2006.01) |
| A61P 31/20 | (2006.01) |
| A61P 31/22 | (2006.01) |
| A61P 35/00 | (2006.01) |
| A61P 35/02 | (2006.01) |
| A61P 37/00 | (2006.01) |
| A61P 37/02 | (2006.01) |
| A61P 37/06 | (2006.01) |

(Continued)

(52) U.S. Cl.
CPC ............ *C07D 471/04* (2013.01); *A61P 37/06* (2018.01); *C07D 519/00* (2013.01)

(58) Field of Classification Search
CPC .. C07D 471/04; C07D 471/08; C07D 471/10; C07D 519/00; C07D 487/04; C07D 487/10; C07D 498/08; A61P 37/06; A61P 37/02; A61P 37/00; A61P 35/00; A61P 35/02; A61P 29/00; A61P 1/00; A61P 3/10; A61P 7/00; A61P 7/02; A61P 9/10; A61P 11/02; A61P 11/06; A61P 17/00; A61P 17/06; A61P 19/02; A61P 25/00; A61P 25/28; A61P 27/02; A61P 31/12; A61P 31/20; A61P 31/22; A61P 31/437; A61P 31/4545
See application file for complete search history.

(56) References Cited

U.S. PATENT DOCUMENTS

2022/0177467 A1    6/2022   Wu et al.

FOREIGN PATENT DOCUMENTS

| AU | 2020214895 A1 | 9/2021 |
| CN | 108570048 A | 9/2018 |

(Continued)

OTHER PUBLICATIONS

Cancerprevention, 2024, https://www.mayoclinic.org/healthy-lifestyle/adult-health/in-depth/cancer-prevention/art-20044816.*

(Continued)

*Primary Examiner* — Sun Jae Yoo
(74) *Attorney, Agent, or Firm* — Bret E. Field; Bozicevic, Field & Francis LLP

(57) ABSTRACT

A 7-azaindole derivative having the structure of formula (I), a pharmaceutical composition containing the compound of formula (I), and uses of the compound in preparing a medicament for preventing or treating Janus kinase (JAK) family-related diseases, specifically, uses in preventing or treating inflammatory diseases related to protein tyrosine kinase.

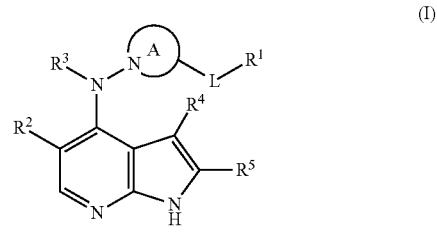

(I)

13 Claims, 17 Drawing Sheets

(51) Int. Cl.
  *C07D 471/08* (2006.01)
  *C07D 471/10* (2006.01)
  *C07D 487/04* (2006.01)
  *C07D 487/10* (2006.01)
  *C07D 498/08* (2006.01)
  *C07D 519/00* (2006.01)

(56) References Cited

FOREIGN PATENT DOCUMENTS

| EP | 3919494 A1 | 12/2021 |
|---|---|---|
| JP | 2009-501130 A | 1/2009 |
| JP | 2018-502899 A | 2/2018 |
| JP | 2018-536634 A | 12/2018 |
| JP | 7344304 B2 | 9/2023 |
| KR | 10-2017-0101309 A | 9/2017 |
| WO | WO2008144253 A1 | 11/2008 |
| WO | WO2013114113 A1 | 8/2013 |
| WO | WO2016116025 A1 | 7/2016 |
| WO | WO2018169700 A1 | 9/2018 |
| WO | WO2020156271 A1 | 8/2020 |

OTHER PUBLICATIONS

MultipleSclerosis Prevention, 2024, https://www.healthline.com/health/multiple-sclerosis-prevention.*

Rhematoidarthritis, 2024, https://www.healthcentral.com/condition/rheumatoid-arthritis/rheumatoid-arthritis-prevention.*

First Office Action & Search Report mailed Feb. 19, 2021, for Chinese Patent Application No. 202010050671.4, and English translation, 11 pages.

Second Office Action & Search Report mailed Jul. 16, 2021, for Chinese Patent Application No. 202010050671.4, and English translation, 9 pages.

First Office Action mailed Apr. 4, 2022, for Australian Patent Application No. 2020214895, 4 pages.

First Office Action mailed Sep. 20, 2021, for Indian Patent Application No. 202137036354, 6 pages.

Merour et al., The Azaindole Framework in the Design of Kinase Inhibitors, Molecules, Nov. 2014, vol. 19, p. 19935-19979.

The First Korean Office Action from the corresponding Korean Patent Application No. 10-2021-7027137, mailed on Oct. 8, 2023, and its English translation, 13 pages.

The Second Korean Office Action from the corresponding Korean Patent Application No. 10-2021-7027137, mailed on Jun. 25, 2024, and its English translation, 7 pages.

The Third Canadian Office Action from the corresponding Canadian Patent Application No. 3, 128,421, mailed on Mar. 11, 2024, 3 pages.

The First Japanese Office Action from the corresponding Japanese Patent Application No. 2023-088385 (Divisional of JP2021-543350), mailed on May 14, 2024, and its English translation, 8 pages.

Office Action for corresponding Canada Patent Application No. 3,128,421, dated Aug. 3, 2023, 6 pages.

First Office Action mailed on Jul. 26, 2022, for corresponding Japanese Patent Application No. 2021-543350 and its English translation, 6 pages.

Second Office Action mailed on Feb. 7, 2023, for corresponding Japanese Patent Application No. 2021-543350 and its English translation, 7 pages.

Notification on Grant of Patent Right for Invention for Chinese Patent Application No. 202010050671.4 and its English translation, 3 pages, 2022.

First Office Action mailed on Oct. 17, 2022, for corresponding Canadian Patent Application No. 3,128,421, 5 pages.

First Office Action mailed on Jul. 4, 2022, for corresponding European Patent Application No. 20749430.3, 5 pages.

* cited by examiner

JANUS KINASE (JAK) FAMILY INHIBITOR, PREPARATION OF SAME, AND APPLICATIONS THEREOF

TECHNICAL FIELD

The present application relates to the field of medical technology, and in particular to a 7-azaindole derivative and uses thereof in preparing an anti-inflammatory medicament.

BACKGROUND ART

Janus kinase (JAK) is a kind of tyrosine kinases, including four members: JAK1, JAK 2, JAK3 and TYK2. JAKs play an important role in the signaling process of a variety of cytokines, and mediate, together with their downstream signal transducer and activator of transcription (STAT), the regulation of transcription and expression of intranuclear genes by cytokine receptors.

Cytokine is bound to its receptor, resulting in dimerization of the receptor molecule, and JAKs coupled with the receptor are in proximity to each other and are activated through phosphorylation of interactive tyrosine residues. The activated JAKs catalyze the phosphorylation of tyrosine residues of the receptor itself, forming corresponding sites for binding ST ATs to the receptor complex. STATs are bound through their SH2 domains to the phosphotyrosine residues on the receptor molecule, and the phosphorylation of their C-terminal tyrosine residues is achieved under the effect of JAKs. Two phosphorylated STAT molecules interact with each other to form homologous/heterologous dimers, which leaves the receptor molecules into the cell nucleus, bind to a promoter region of a target gene and regulate the transcription and expression of the gene (J. Biol Chem. 2007, 282, 20059).

The JAK/STAT system is the most important intracellular signaling system for cytokines in immunocompetent cells; and about 40 cytokines can signal through combinations of 4 JAKs and 7 STATs (Immunol Rev. 2009, 228, 273). JAK3 can be specifically bound to the common γ chain (Fcγ) of cytokine receptor, while JAK1 is bound to a beta chain, and both of them are activated by IL-2, IL-4, IL-7, IL-9, IL-15 and IL-21 cytokines (Immunol. Rev. 2009, 228, 273). Some important inflammation-related cytokines, such as IL-6, only signal through JAK1 (EMBO J. 1995, 14, 1421), and one IL-6 monoclonal antibody, such as tocilizumab, has already been proved to be an effective medicament for treating rheumatoid arthritis (Arthritis Rheum. 2006, 54, 2817). Therefore, JAK1 is an ideal anti-inflammatory target. JAK2 plays an important role in the erythropoietin (EPO) signaling pathway, including promoting red blood cell differentiation and activating STAT5. In addition, JAK2 is also associated with the lipid metabolism pathway (Obesity. 2008, 16, 492). JAK1, JAK2 and TYK2 widely exist in various tissues and cells, while JAK3 is mainly found in lymphocytes, and excessive inhibition may increase the risk of infection. Abnormal cytokine production and abnormal cytokine signaling are not only associated with various immunological diseases and inflammatory diseases such as autoimmune diseases and allergy, but also are closely related to multiple diseases with different pathologies such as cancer. The modulations of many abnormal immune responses, such as autoimmune diseases including allergy, asthma, (allogeneic) transplant rejection, rheumatoid arthritis, amyotrophic lateral sclerosis and multiple sclerosis, myelodysplastic disorders, and hematological malignancies including leukemia and lymphoma, are all associated with the JAK/STAT signaling pathway.

Tofatinib is the first marketed oral JAK inhibitor. However, as a pan-JAK inhibitor, it has poor selectivity and inhibits JAK1 as well as JAK2 and JAK3, and shows great clinical side effects, including anemia and infection, thereby affecting the clinical dosage and final efficacy (Transplantation. 2005, 79, 791, Annals of the Rheumatic Diseases. 2016, 75, 1133.). A JAK1/JAK2 inhibitor Baricitinib shows a better anti-inflammatory effect than Humira (adalimumab) in clinical trials, but leads to a significant side effect of increasing blood lip ids (Ann Rheum Dis. 2018, 77, 988.), and thus is only approved by FDA to be sold as a low-dose version. A selective JAK1 inhibitor ABT-494 also shows an excellent anti-inflammatory effect in clinical trials, but still has a clinical risk of increasing low density lipoprotein (LDL) (Arthritis & Rheumatology. 2016, 68, 2857). As a result, developing a JAK inhibitor with better selectivity still has an important clinical significance.

Tyk2 is also a member of the JAK family. As an important immunoregulatory site, it participates in the transduction of the IFN-α, IL-6, IL-10, IL-12 and IL-23 signaling pathways, and can phosphorylate the downstream STAT proteins of IL-12, IL-23 and type I interferon receptor and transduce an inflammation signal. The above-mentioned inflammatory factors are associated with multiple autoimmune diseases, including systemic lupus erythematosus (SLE), psoriasis (POS) and inflammatory bowel disease (IBD). Therefore, Tyk2 is also an important target for treating inflammatory diseases. Several Tyk2 inhibitors have now proceeded to clinical trial research of systemic lupus erythematosus, psoriasis, inflammatory bowel disease and alopecia areata (J. Med. Chem. 2018, 61, 8597; J. Med. Chem., 2018, 61, 85 94).

WO2018169700 and WO2016116025 disclose compounds of JAK inhibitors, but the compound of the present invention has different structures and has an overall better inhibitory activity on JAK1 than the compounds in the patents WO2018169700 and WO2016116025.

SUMMARY OF THE INVENTION

An objective of the present invention is to provide a 7-azaindole JAK family inhibitor.

Another objective of the present invention is to provide uses of a high-selectivity JAK family inhibitor in preparing a medicament for preventing or treating JAK family-related diseases. To achieve the above-mentioned objectives, the present invention provides the following technical solution:

The compound of formula (I) of the present invention, a stereoisomer thereof or a pharmaceutically acceptable salt thereof:

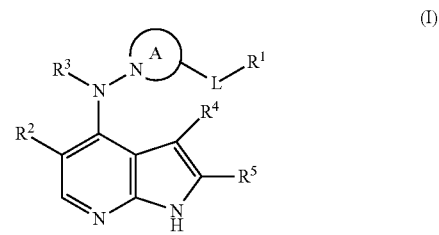

wherein the ring A is selected from optionally substituted 4-12-membered heterocyclyl or 5-10-membered heteroaryl;

$R^1$ is selected from H, hydroxyl, optionally substituted $C_1$-$C_8$ alkyl, $C_3$-$C_8$ cycloalkyl, $C_2$-$C_8$ alkenyl, $C_2$-$C_8$ alkynyl, 4-12-membered heterocyclyl, 6-10-membered aryl or 5-10-membered heteroaryl;

$R^2$ is selected from cyano, —C=ONR$^6$R$^7$, —C=ONR$^6$NR$^7$R$^8$, —C=ONHOR$^6$, —S(O)$_m$R$^8$, —S(O)$_m$—NHR$^8$ or —C=OOR$^6$;

L is selected from amino, —NR$^6$C=O—, —NR$^6$C=ONR$^{10}$—, —C=ONR$^{10}$—, —C=ONR$^6$O—, —C=O NR$^6$NR$^{10}$—, —NR$^6$S(O)$_m$—, —S(O)$_m$NR$^6$—, —NR$^6$S(O)$_m$NR$^7$—, —S(O)$_m$—, —C=O— or —C=OO—; or L is absent;

$R^3$ is selected from H, optionally substituted $C_1$-$C_8$ alkyl, $C_3$-$C_8$ cycloalkyl or —C=OR$^6$;

$R^4$ and $R^5$ are each independently selected from H, deuterium, halogen, cyano, nitro, optionally substituted $C_1$-$C_8$ alkyl, $C_3$-$C_8$ cycloalkyl, 6-10-membered aryl or 5-10-membered heteroaryl;

$R^6$, $R^7$ and $R^{10}$ are each independently selected from H, optionally substituted $C_1$-$C_8$ alkyl or $C_3$-$C_8$ cycloalkyl;

or, $R^{10}$ taken with N and $R^1$ to which it is attached can form an optionally substituted 4-12-membered heterocyclyl;

wherein the substituent groups in the ring A and $R^1$ are each independently selected from one or more of halogen, hydroxyl, cyano, amino, sulfydryl, nitro, $C_1$-$C_8$ alkyl, $C_1$-$C_8$ alkoxy, $C_3$-$C_8$ cycloalkyl, 4-12-membered heterocyclyl, 6-10-membered aryl, 5-10-membered heteroaryl, —(CH$_2$)$_n$C=OOR$^8$, —OC=OR$^8$, —C=OR$^8$, —C=ONR$^8$R$^9$, —NHC=OR$^8$, —NR$^8$R$^9$, —OC=ONR$^8$R$^9$, —NHC=ONR$^8$R$^9$, —S(O)$_m$R$^8$, —S(O)$_m$—NHR$^8$, —NHC=OOR$^8$ or —NHS(O)$_m$R$^8$;

m is selected from 1 or 2:

n is selected from 1, 2, 3, 4 or 5:

$R^8$ and $R^9$ are each independently selected from H, optionally substituted $C_1$-$C_8$ alkyl or $C_3$-$C_8$ cycloalkyl; and the substituent groups in the $R^3$, $R^4$, $R^5$, $R^6$, $R^7$, $R^8$, $R^9$ and $R^{10}$ are each independently selected from one or more of deuterium, halogen, hydroxyl, cyano, amino, sulfydryl, nitro, $C_1$-$C_8$ alkyl, $C_1$-$C_8$ alkoxy or $C_3$-$C_8$ cycloalkyl.

In some embodiments of the present invention, the ring A is selected from optionally substituted 4-12-membered heterocyclyl:

$R^1$ is selected from H, hydroxyl, optionally substituted $C_1$-$C_8$ alkyl, $C_3$-$C_8$ cycloalkyl, $C_2$-$C_8$ alkenyl, $C_2$-$C_8$ alkynyl, 4-12-membered heterocyclyl, 6-10-membered aryl or 5-10-membered heteroaryl;

$R^2$ is selected from cyano or —C=ONR$^6$R$^7$;

L is selected from amino, —NR$^6$C=O—, —NR$^6$C=ONR$^{10}$—, —C=ONR$^{10}$—, —C=ONR$^6$O—, —C=O NR$^6$NR$^{10}$—, —NR$^6$S(O)$_m$—, —S(O)$_m$NR$^6$—, —NR$^6$S(O)$_m$NR$^7$—, —S(O)$_m$—, —C=O— or —C=OO—; or L is absent;

$R^3$ is selected from H, optionally substituted $C_1$-$C_8$ alkyl, $C_3$-$C_8$ cycloalkyl or —C=OR$^6$;

$R^4$ and $R^5$ are each independently selected from H, deuterium, halogen, cyano, nitro, optionally substituted $C_1$-$C_8$ alkyl or $C_3$-$C_8$ cycloalkyl;

$R^6$, $R^7$ and $R^{10}$ are each independently selected from H, optionally substituted $C_1$-$C_8$ alkyl or $C_3$-$C_8$ cycloalkyl;

or, $R^{10}$ taken with N and $R^1$ to which it is attached can form an optionally substituted 4-12-membered heterocyclyl;

wherein the substituent groups in the ring A and $R^1$ are each independently selected from one or more of halogen, hydroxyl, cyano, amino, $C_1$-$C_8$ alkyl, $C_1$-$C_8$ alkoxy, $C_3$-$C_8$ cycloalkyl, 4-12-membered heterocyclyl, 6-10-membered aryl, 5-10-membered heteroaryl, —C=ONR$^8$R$^9$, —NHC=OR$^8$, —NR$^8$R$^9$, —OC=ONR$^8$R$^9$, —NHC=ONR$^8$R$^9$, —S(O)$_m$R$^8$, —S(O)$_m$—NHR$^8$, —NHC=OOR$^8$ or —NHS(O)$_m$R$^8$;

m is selected from 1 or 2;

$R^8$ and $R^9$ are each independently selected from H, optionally substituted $C_1$-$C_8$ alkyl or $C_3$-$C_8$ cycloalkyl; and the substituent groups in the $R^3$, $R^4$, $R^5$, $R^6$, $R^7$, $R^8$, $R^9$ and $R^{10}$ are each independently selected from one or more of deuterium, halogen, hydroxyl, cyano, amino, $C_1$-$C_8$ alkyl, $C_1$-$C_8$ alkoxy or $C_3$-$C_8$ cycloalkyl.

In some embodiments of the present invention, the ring A is selected from optionally substituted 4-12-membered heterocyclyl;

$R^1$ is selected from H, hydroxyl, optionally substituted $C_1$-$C_8$ alkyl, $C_3$-$C_8$ cycloalkyl, $C_2$-$C_8$ alkenyl, $C_2$-$C_8$ alkynyl, 4-12-membered heterocyclyl, 6-10-membered aryl or 5-10-membered heteroaryl;

$R^2$ is selected from cyano or —C=ONR$^6$R$^7$;

L is selected from amino, —NR$^6$C=O—, —NR$^6$C=ONR$^{10}$—, —C=ONR$^{10}$—, —C=ONR$^6$O—, —C=O NR$^6$NR$^{10}$—, —NR$^6$S(O)$_m$—, —S(O)$_m$NR$^6$—, —NR$^6$S(O)$_m$NR$^7$—, —S(O)$_m$—, —C=O— or —C=OO—; or L is absent;

$R^3$ is selected from H or methyl;

$R^4$ and $R^5$ are each independently selected from H, deuterium, halogen, cyano, nitro, optionally substituted $C_1$-$C_8$ alkyl or $C_3$-$C_8$ cycloalkyl;

$R^6$, $R^7$ and $R^{10}$ are each independently selected from H, optionally substituted $C_1$-$C_8$ alkyl or $C_3$-$C_8$ cycloalkyl;

or, $R^{10}$ taken with N and $R^1$ to which it is attached can form an optionally substituted 4-12-membered heterocyclyl;

wherein the substituent groups in the ring A and $R^1$ are each independently selected from one or more of halogen, hydroxyl, cyano, amino, $C_1$-$C_8$ alkyl, $C_1$-$C_8$ alkoxy, $C_3$-$C_8$ cycloalkyl, 4-12-membered heterocyclyl, 6-10-membered aryl, 5-10-membered heteroaryl, —C=ONR$^8$R$^9$, —NHC=OR$^8$, —NR$^8$R$^9$, —OC=ONR$^8$R$^9$, —NHC=ONR$^8$R$^9$, —S(O)$_m$R$^8$, —S(O)$_m$—NHR$^8$, —NHC=OOR$^8$ or —NHS(O)$_m$R$^8$;

m is selected from 1 or 2;

$R^8$ and $R^9$ are each independently selected from H, optionally substituted $C_1$-$C_8$ alkyl or $C_3$-$C_8$ cycloalkyl; and the substituent groups in the $R^4$, $R^5$, $R^6$, $R^7$, $R^8$, $R^9$ and $R^{10}$ are each independently selected from one or more of deuterium, halogen, hydroxyl, cyano, amino, $C_1$-$C_8$ alkyl, $C_1$-$C_8$ alkoxy or $C_3$-$C_8$ cycloalkyl.

In some embodiments of the present invention, the ring A is selected from the following optionally substituted groups:

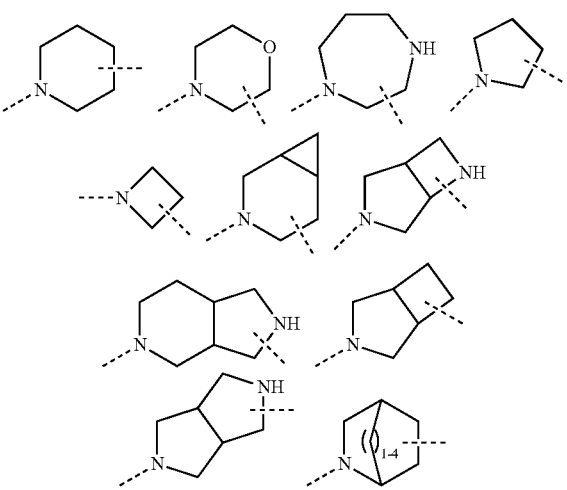

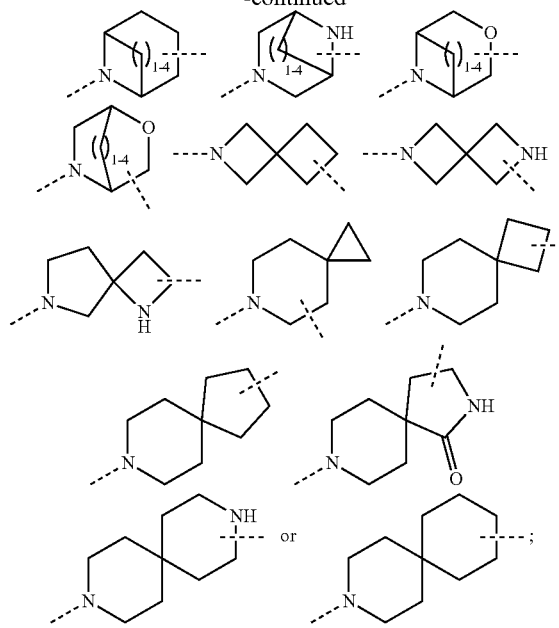

R[1] is selected from H, hydroxyl, optionally substituted C$_1$-C$_8$ alkyl, C$_3$-C$_8$ cycloalkyl, 4-12-membered heterocyclyl, 6-10-membered aryl or 5-10-membered heteroaryl;

R[2] is selected from cyano or —C=ONR[6]R[7];

L is selected from amino, —NR[6]C=O—, —NR[6]C=ONR[10]—, —C=ONR[10]—, —C=ONR[6]O—, —C=O NR[6]NR[10]—, —NR[6]S(O)$_m$—, —S(O)$_m$NR[6]—, —NR[6]S(O)$_m$NR[7], S(O)$_m$—, —C=O— or —C=OO—;

or L is absent;

R[3] is selected from H or methyl;

R[4] and R[5] are each independently selected from H, deuterium, halogen, cyano, nitro, optionally substituted C$_1$-C$_8$ alkyl or C$_3$-C$_8$ cycloalkyl;

R[6], R[7] and R[10] are each independently selected from H, optionally substituted C$_1$-C$_8$ alkyl or C$_3$-C$_8$ cycloalkyl;

or, R[10] taken with N and R[1] to which it is attached can form an optionally substituted 4-12-membered heterocyclyl; and m is selected from 1 or 2;

wherein the substituent groups in the ring A and R[1] are each independently selected from one or more of halogen, hydroxyl, cyano, amino, C$_1$-C$_8$ alkyl, C$_1$-C$_8$ alkoxy, C$_3$-C$_8$ cycloalkyl, 4-12-membered heterocyclyl, 6-10-membered aryl, 5-10-membered heteroaryl, —C=ONR[8]R[9], —NHC=OR[8], —NR[8]R[9], —OC=ONR[8]R[9], —NHC=ONR[8]R[9], —S(O)$_m$R[8], —S(O)$_m$—NHR[8], —NHC=OOR[8] or —NHS(O)$_m$R[8];

R[8] and R[9] are each independently selected from H, optionally substituted C$_1$-C$_8$ alkyl or C$_3$-C$_8$ cycloalkyl; and the substituent groups in the R[4], R[5], R[6], R[7], R[8], R[9] and R[10] are each independently selected from one or more of deuterium, halogen, hydroxyl, cyano, amino. C$_1$-C$_8$ alkyl, C$_1$-C$_8$ alkoxy or C$_3$-C$_8$ cycloalkyl.

In some embodiments of the present invention, the ring A is selected from the following optionally substituted groups:

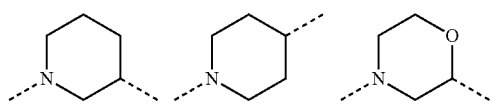

R[1] is selected from H, hydroxyl, optionally substituted methyl, ethyl, propyl, cyclopropyl, n-butyl, tert-butyl, cyclobutyl, phenyl, pyridinyl, imidazolyl, pyrazolyl, oxazolyl, thiazolyl or

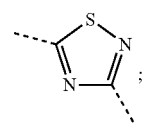

R[2] is selected from cyano or —C=ONR[6]R[7];

L is selected from amino, —NR[6]C=O—, —NR[6]C=ONR[10]—, —C=ONR[10]—, —C=ONR[6]O—, —C=O NR[6]NR[10]—, —NRS(O)$_m$—, —S(O)$_m$NR[6]—, —NR[6]S(O)$_m$NR[7]—, —S(O)$_m$—, —C=O— or —C=OO—;

or L is absent;

R[3] is selected from H or methyl;

R[4] and R[5] are each independently selected from H, deuterium, halogen or cyano:

R⁶, R⁷ and R¹⁰ are each independently selected from H, optionally substituted $C_1$-$C_8$ alkyl or $C_3$-$C_8$ cycloalkyl;

or, R¹⁰ taken with N and R¹ to which it is attached can form an optionally substituted 4-12-membered heterocyclyl; and m is selected from 1 or 2;

wherein the substituent groups in the ring A and R¹ are each independently selected from one or more of halogen, hydroxyl, cyano, amino, $C_1$-$C_8$ alkyl, $C_1$-$C_8$ alkoxy, $C_3$-$C_8$ cycloalkyl, 4-12-membered heterocyclyl, 6-10-membered aryl or 5-10-membered heteroaryl:

the substituent groups in the R⁶, R⁷ and R¹⁰ are each independently selected from one or more of deuterium, halogen, hydroxyl, cyano, amino, $C_1$-$C_8$ alkyl, $C_1$-$C_8$ alkoxy or $C_3$-$C_8$ cycloalkyl.

In some embodiments of the present invention, the ring A is selected from the following optionally substituted groups:

R¹ is selected from H, hydroxyl, optionally substituted methyl, ethyl, propyl, cyclopropyl, n-butyl, tert-butyl, cyclobutyl, phenyl, pyridinyl, imidazolyl, pyrazolyl, oxazolyl, thiazolyl or:

R² is selected from cyano or —C=ONR⁶R⁷;

L is selected from amino, —NR⁶C=O—, —C=ONR¹⁰—, —S(O)$_m$—, —C=O— or —C=OO—;

or L is absent;

R³ is selected from H or methyl:

R⁴ and R⁵ are each independently selected from H, deuterium, F, Cl or cyano;

R⁶, R⁷ and R¹⁰ are each independently selected from H, optionally substituted $C_1$-$C_8$ alkyl or $C_3$-$C_8$ cycloalkyl;

or, R¹⁰ taken with N and R¹ to which it is attached can form an optionally substituted 4-12-membered heterocyclyl; and m is selected from 1 or 2;

wherein the substituent groups in the ring A and R¹ are each independently selected from one or more of halogen, hydroxyl, cyano, amino, $C_1$-$C_4$ alkyl or $C_1$-$C_4$ alkoxy;

the substituent groups in the R⁶, R⁷ and R¹⁰ are each independently selected from one or more of deuterium, halogen, hydroxyl, cyano or amino.

In some embodiments of the present invention, the ring A is selected from the following optionally substituted groups:

R¹ is selected from H, hydroxyl, optionally substituted methyl, ethyl, propyl, cyclopropyl, tert-butyl, cyclobutyl or;

R² is selected from cyano or —C=ONR⁶R⁷;

R⁶ and R⁷ are selected from H, methyl or deuterated methyl;

L is selected from —C=ONR¹⁰—, —S(O)$_m$—, —C=O— or —C=OO—;

or L is absent;

R³ is selected from H or methyl:

R⁴ and R⁵ are each independently selected from H or deuterium:

R¹⁰ is H; and m is selected from 1 or 2;

wherein the substituent groups in the ring A and R¹ are each independently selected from one or more of F, Cl, hydroxyl, cyano, amino, methyl or methoxy.

In some embodiments of the present invention, the compound is a compound as shown below or a pharmaceutically acceptable salt thereof:

-continued
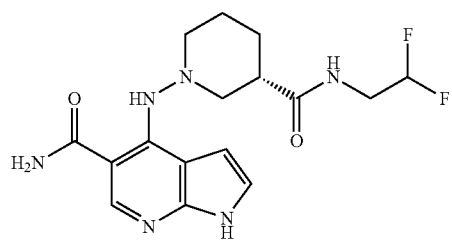
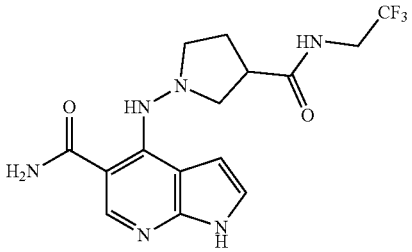
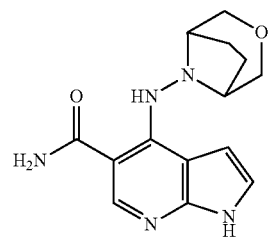
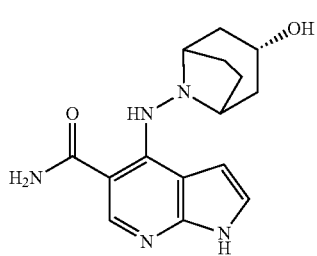
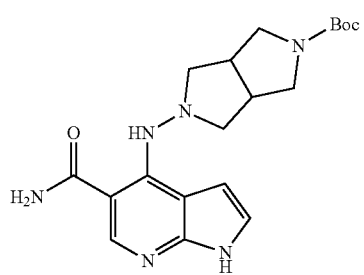
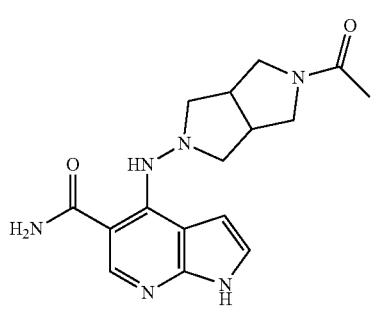
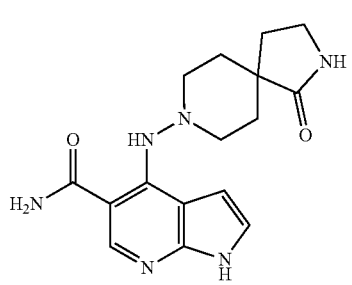

-continued
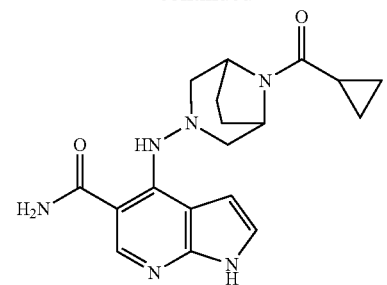
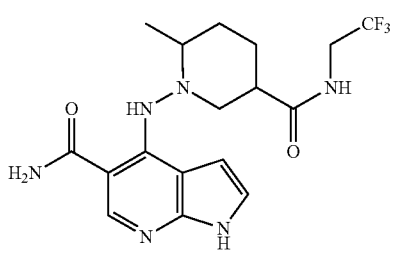
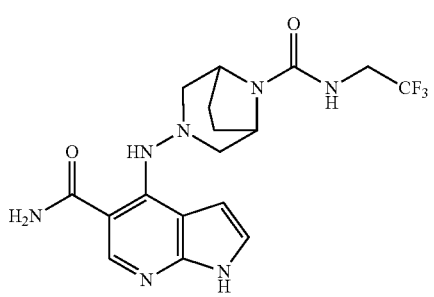
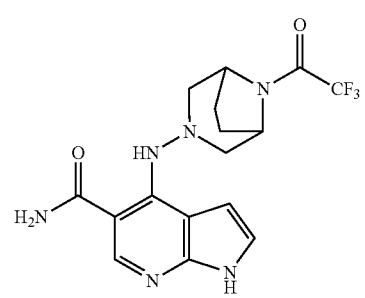
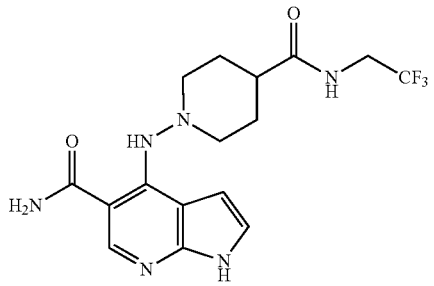
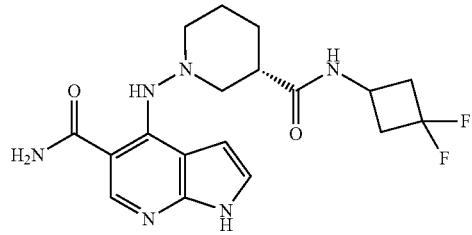
-continued
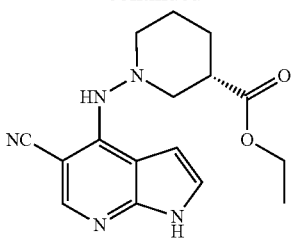
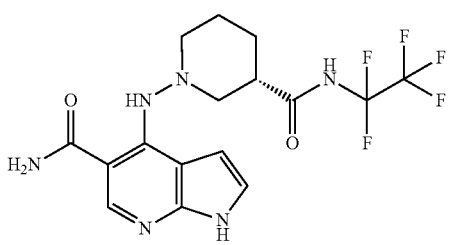
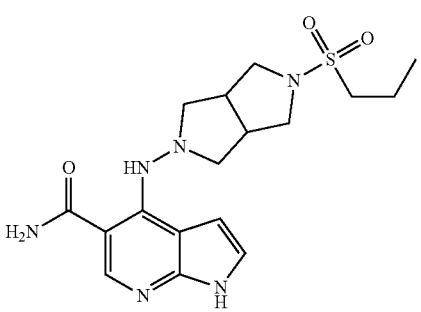
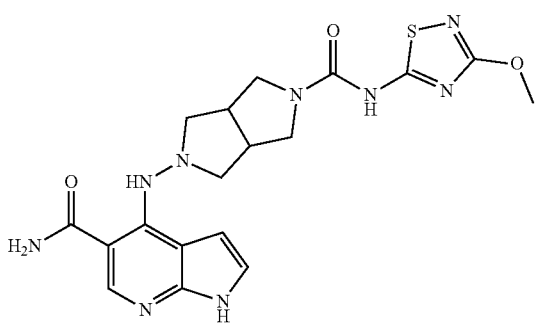
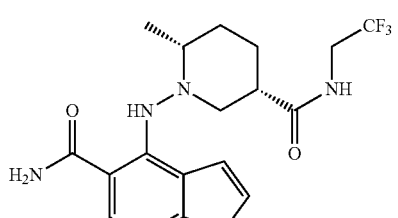
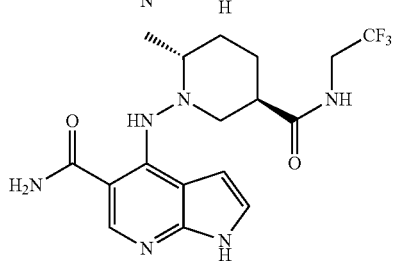

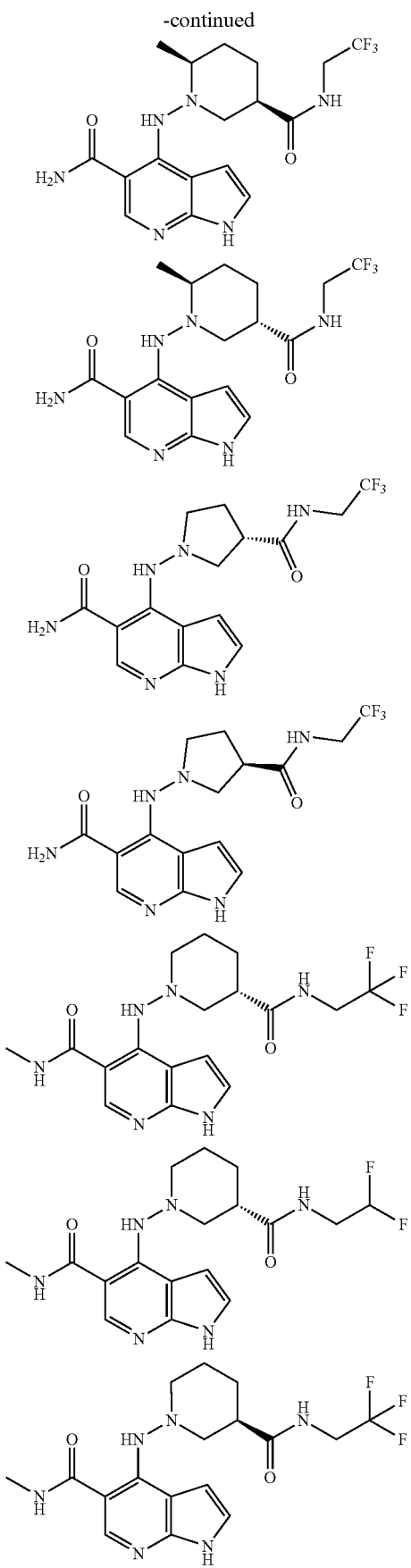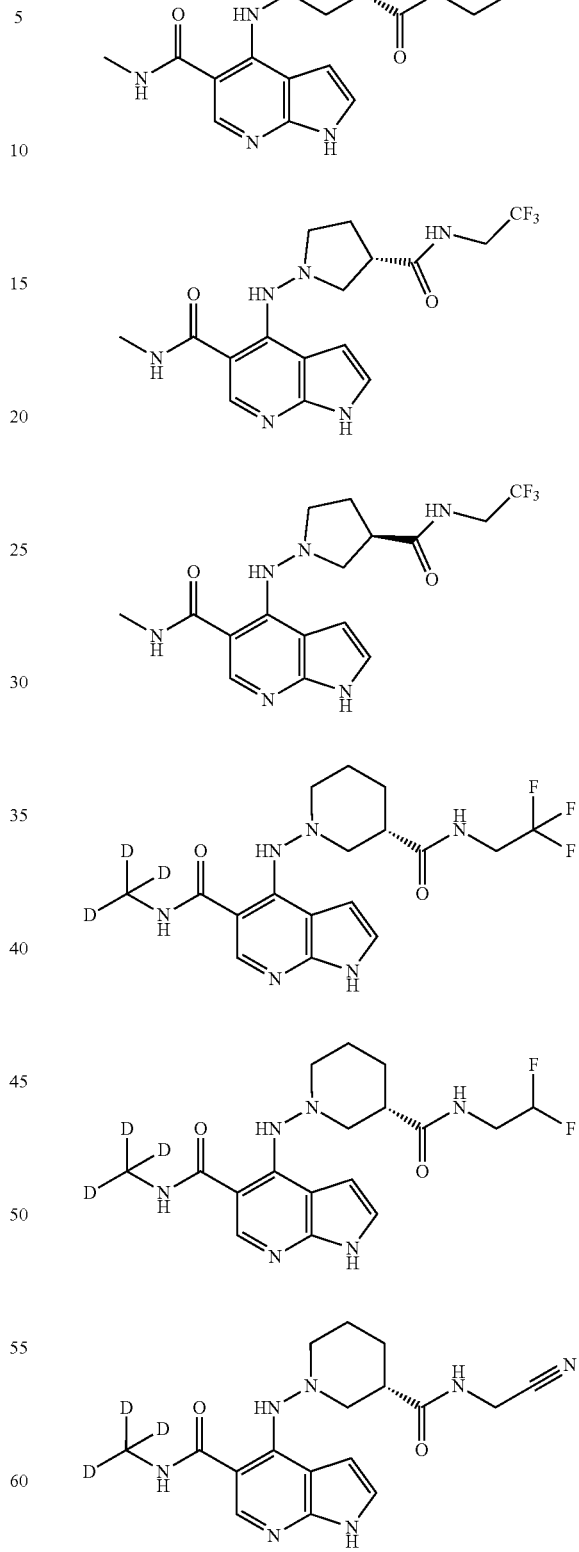
Preferably, the compound of the present invention is a compound shown below or a pharmaceutically acceptable salt thereof:

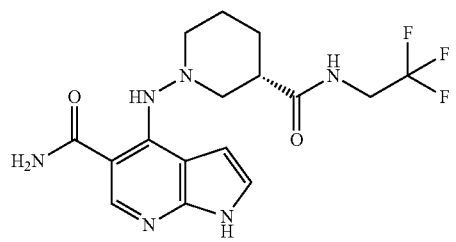
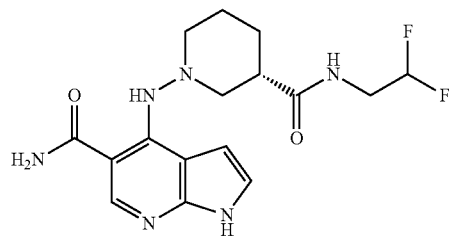
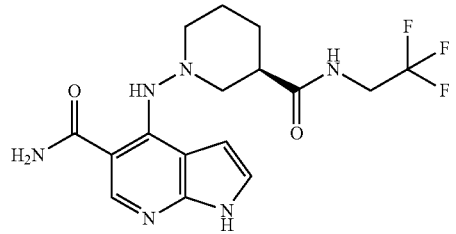
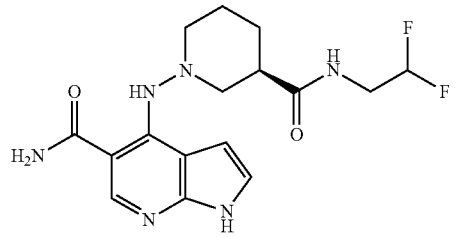
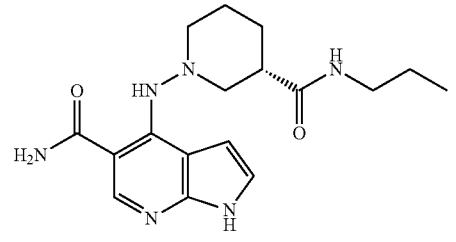
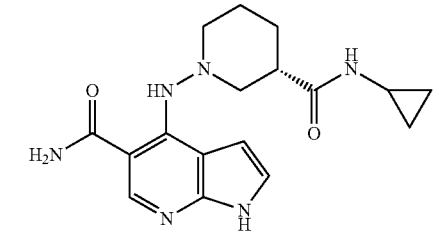
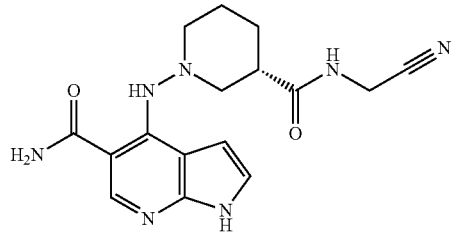
-continued
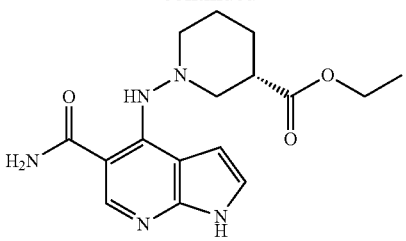
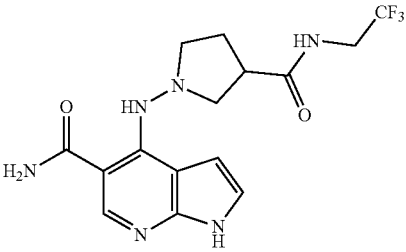
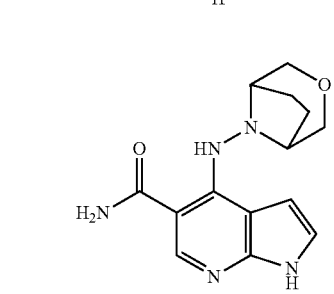
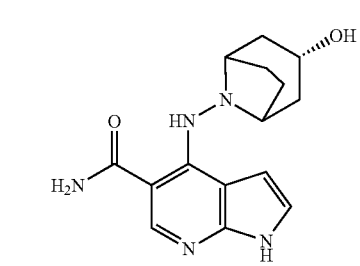
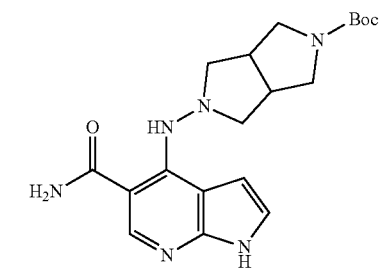
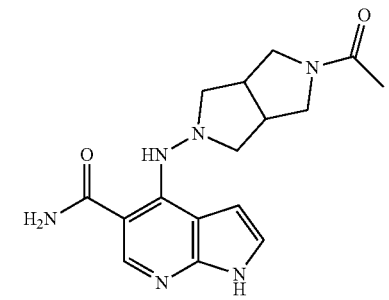

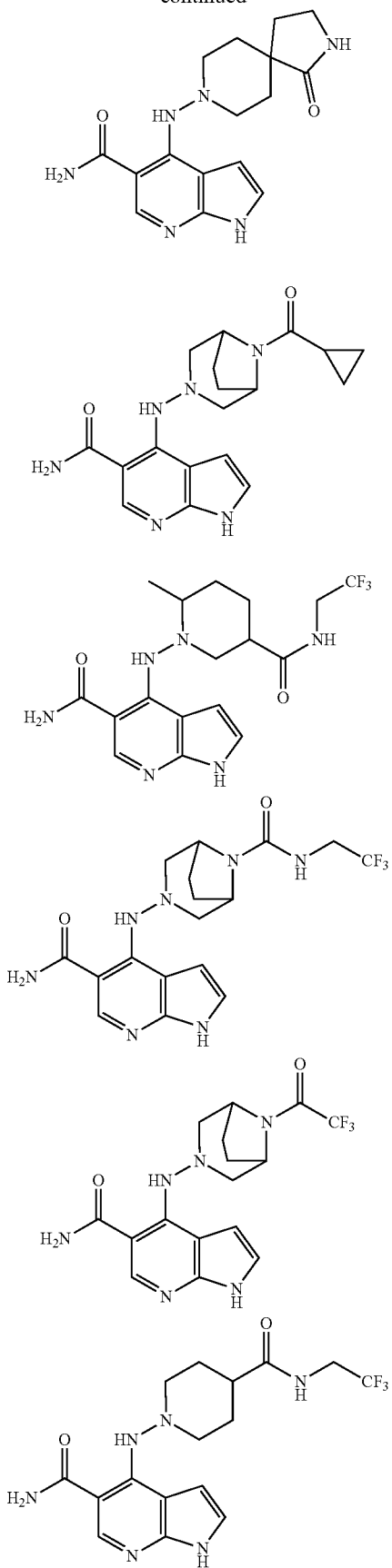

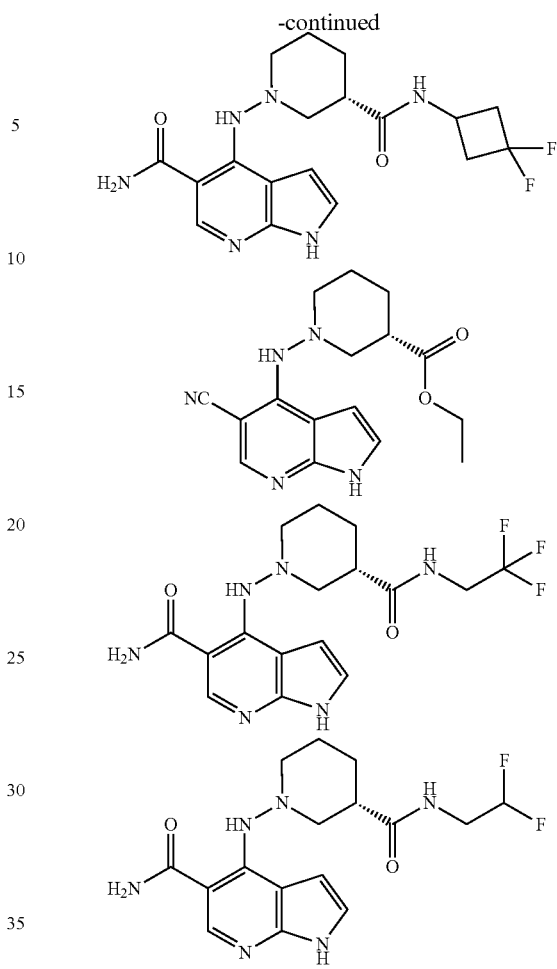

Another aspect of the present invention provides a method of preparing the compound of formula (I), a stereoisomer thereof or a pharmaceutically acceptable salt thereof, including the following steps:

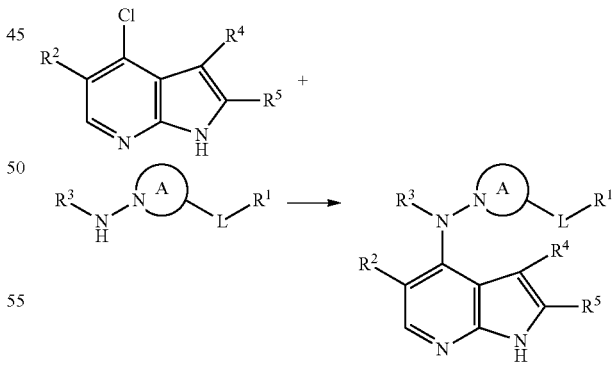

where A, L, $R^1$, $R^2$, $R^3$, $R^4$ and $R^5$ are as defined in the above-mentioned compound of formula (I).

The present invention also provides a pharmaceutical composition, which includes the compound of formula (I), a stereoisomer thereof or a pharmaceutically acceptable salt thereof, and a pharmaceutically acceptable carrier.

Preferably, the pharmaceutical composition is selected from capsule, powder, tablet, granule, pill, injection, syrup, oral liquid, inhalant, ointment, suppository, or patch.

Another aspect of the present invention provides uses of the compound of formula (I) or a tautomer, mesomer, racemate, enantiomer, diastereoisomer thereof, and a mixture thereof, and a pharmaceutically acceptable salt or a pharmaceutical composition including the same in preparing a medicament for preventing or treating JAK family-mediated diseases. The diseases include an immune system disease, an autoimmune disease, a skin disease, an allergic disease, a viral disease, diabetes mellitus type I and diabetic complications, Alzheimer's disease, xerophthalmia, myelofibrosis, thrombocythemia, polycythemia, leukemia and cancer. The immune system disease is organ transplant rejection such as allograft rejection or graft-verse-host disease; the autoimmune disease is selected from systemic lupus erythematosus, multiple sclerosis, rheumatoid arthritis, juvenile arthritis, psoriasis, ulcerative colitis, Crohn's disease and autoimmune thyroid disease; the skin disease is selected from psoriasis, rash, alopecia areata and atopic dermatitis; the allergic disease is selected from asthma and rhinitis; the viral disease is selected from hepatitis B, hepatitis C, chickenpox and herpes zoster virus; the cancer is selected from solid tumor, blood cancer and skin cancer, where the solid tumor is selected from prostatic cancer, renal cancer, liver cancer, pancreatic cancer, gastric cancer, breast cancer, lung cancer, head-and-neck cancer, thyroid cancer, glioblastoma and melanoma, the blood cancer is selected from lymphoma and leukemia, and the skin cancer is selected from skin T-cell lymphoma and skin B-cell lymphoma.

Unless stated on the contrary, the terms used in the specification and claims have the following meanings.

"Aryl" in the present invention refers to a full-carbon monocyclic or bicyclic group; and "6-10-membered aryl" refers to full-carbon aryl containing 6-10 carbon atoms, such as phenyl and naphthyl. The aryl ring may be fused to heteroaryl, heterocyclyl or cycloalkyl ring, where the ring attached to the parent structure is the aryl ring.

"Heteroaryl" in the present invention refers to a heteroaromatic system containing 1-4 heteroatoms including the heteroatoms of nitrogen, oxygen and sulfur, including, but not limited to, furanyl, thiophenyl, pyridinyl, pyrrolyl, pyrazolyl, N-alkylpyrrolyl, pyrimidinyl, pyrazinyl, imidazolyl, tetrazolyl, oxazolyl,

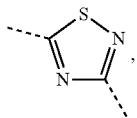

etc.

"$C_1$-$C_8$ alkyl" in the present invention refers to linear alkyl and branched alkyl containing 1-8 carbon atoms. Alkyl refers to a saturated aliphatic hydrocarbon group, such as meth yl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, or various branched isomers thereof, etc.

"Cycloalkyl" in the present invention refers to a saturated monocyclic hydrocarbon substituent group; and "$C_3$-$C_8$ cycloalkyl" refers to monocyclic cycloalkyl containing 3-8 carbon atoms, for example, non-limiting examples of monocyclic cycloalkyl include cyclopropyl, cyclobutyl, cyclopentyl, cyclohexyl, cycloheptyl, cyclooctyl, etc.

"Alkenyl" in the present invention refers to the alkyl as defined above and consisting of at least two carbon atoms and at least one carbon-carbon double bond; and "$C_2$-$C_8$ alkenyl" refers to linear or branched alkenyl containing 2-8 carbon atoms, such as vinyl, 1-propenyl, 2-propenyl, 1-, 2- or 3-butenyl, etc.

"Alkynyl" in the present invention refers to the alkyl as defined above and consisting of at least two carbon atoms and at least one carbon-carbon triple bond; and "$C_2$-$C_8$ alkynyl" refers to linear or branched alkynyl containing 2-8 carbon atoms, such as ethynyl, 1-propynyl, 2-propynyl, 1-, 2- or 3-butynyl, etc.

When the bond " --- " of a substituent group is attached to a definite position, substitution of the substituent group occurs at this position.

When the bond " --- " of a substituent group is cross-attached between two atoms on a ring, such substituent group may be bonded to any atom on the ring, indicating that substitution of the substituent group may occur at any position on the ring. For example, a structural unit

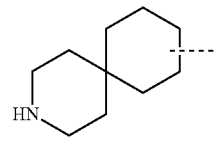

indicates that substitution may take place at any position on cyclohexyl.

"Heterocyclyl" in the present invention refers to a saturated or partially unsaturated monocyclic or polycyclic cyclic hydrocarbon substituent group, where one or more ring atoms are selected from the heteroatoms of nitrogen, oxygen or S(O)$_m$, but not including the ring parts of —O—O—, —O—S— or —S—S—, and the rest ring atoms are carbon. "4-12-membered heterocyclyl" refers to cyclyl containing 4-12 ring atoms. Non-limiting examples of monocyclic heterocyclyl include pyrrolidinyl, piperidyl, piperazinyl, morpholinyl, thiomorpholinyl, homopiperazinyl, etc., and polycyclic heterocyclyl includes the heterocyclyl of a spiral ring, a fused ring and a bridged ring, including, but not limited to, the following structures:

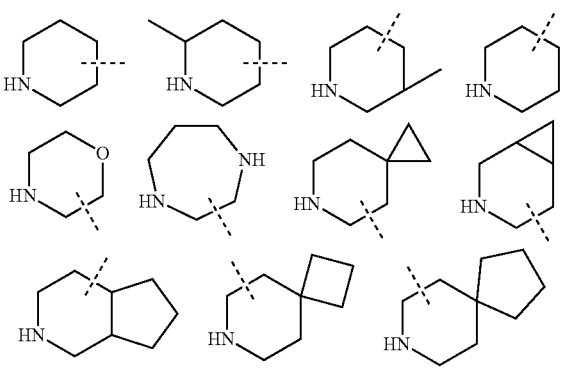

-continued

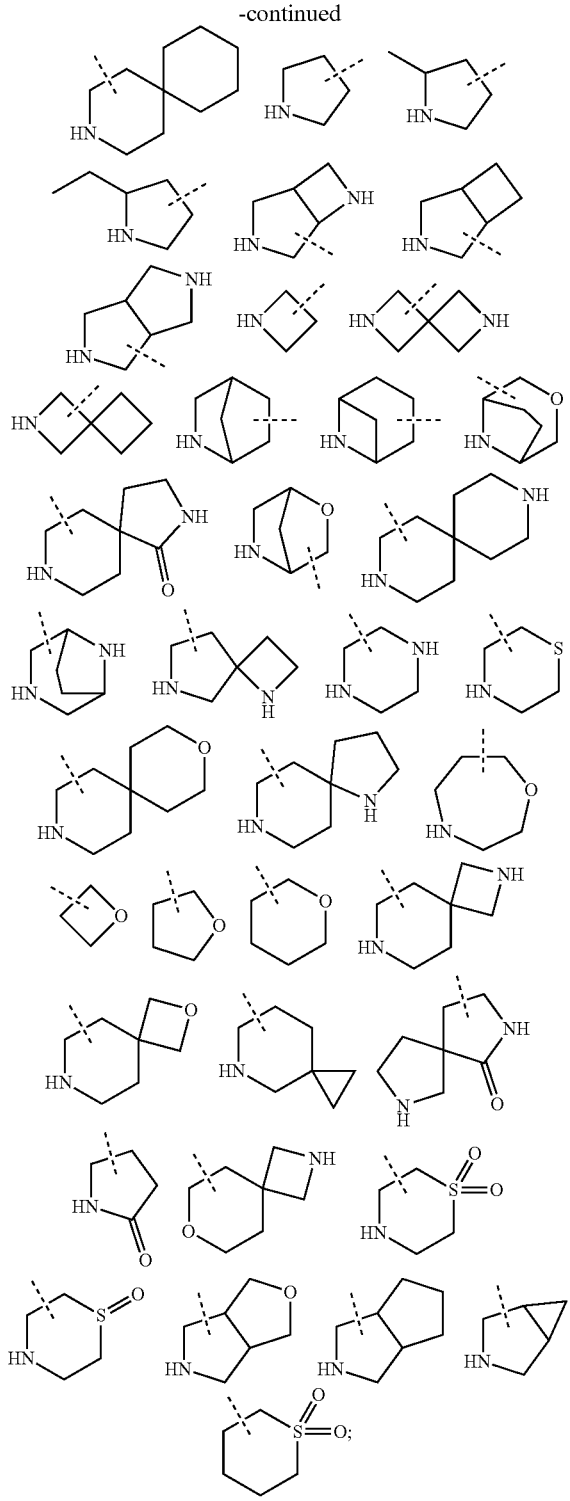

"Alkoxy" in the present invention refers to —O— (alkyl), where the alkyl is as defined above. "$C_1$-$C_8$ alkoxy" refers to alkyloxy containing 1-8 carbon atoms, non-limiting examples of which include methoxy, ethoxy, propoxy, butoxy, etc.

"Halogen" refers to fluorine, chlorine, bromine or iodine.

"Pharmaceutical composition" represents a mixture including one or more compounds described herein or a physiologically and pharmaceutically acceptable salt or prodrug thereof and other chemical components, as well as other components such as a physiologically and pharmaceutically acceptable carrier and excipient. The pharmaceutical composition aims to promote administration to organisms, and facilitate the absorption of active ingredients to exert the biological activity.

"Carrier" refers to a material which does not cause obvious irritation to the organism or eliminate the biological activity and properties of the given compound.

In the preparation steps of the present invention, the abbreviations of the reagents used respectively represent.

DMF N,N-Dimethylformamide
THF Tetrahydrofuran
PE Petroleum ether
EA Ethyl acetate
CDI 1,1-Carbonyldiimidazole
TBTU O-(Benzotriazol-1-yl)-N,N,N',N'-tetramethyluronium tetrafluoroborate
DCM Dichloromethane
Boc tert-butoxycarbonyl
TIPSCl Triisopropylchlorosilane
MeCN Acetonitrile
TFA Trifluoroacetic acid

DETAILED DESCRIPTION OF EMBODIMENTS

Figure 1:
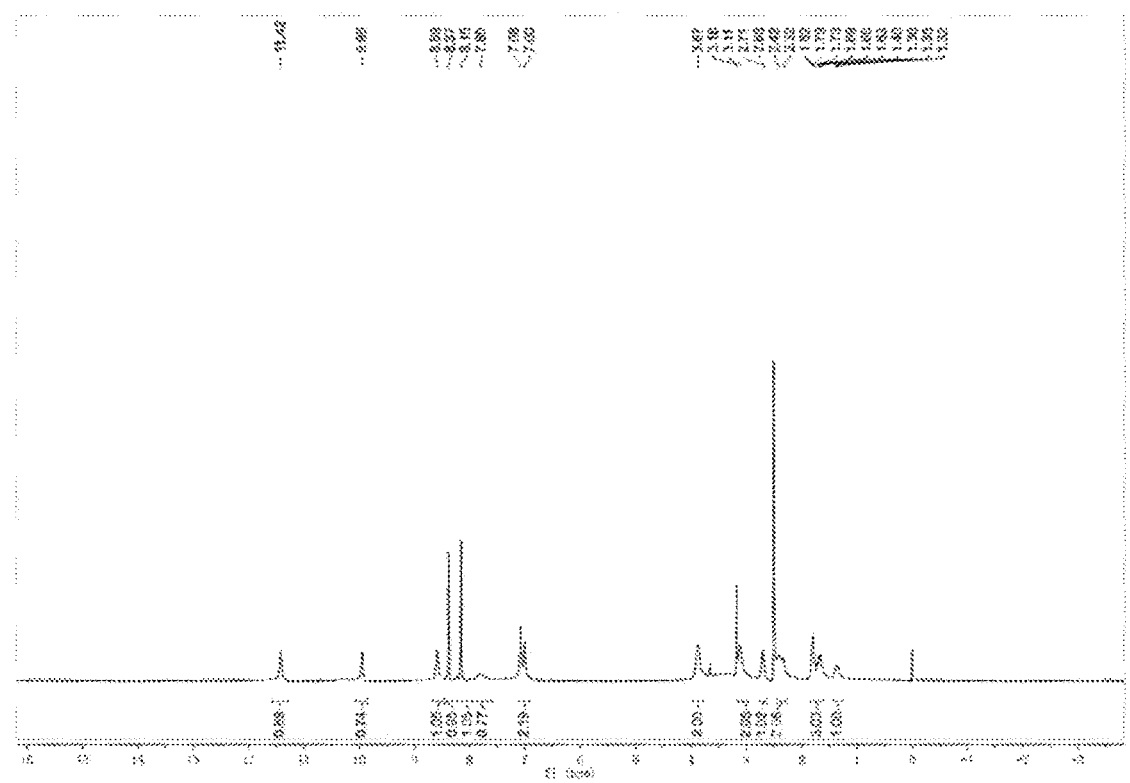
FIG. 1 Hydrogen nuclear magnetic resonance of a compound of Example 1.
Figure 2:
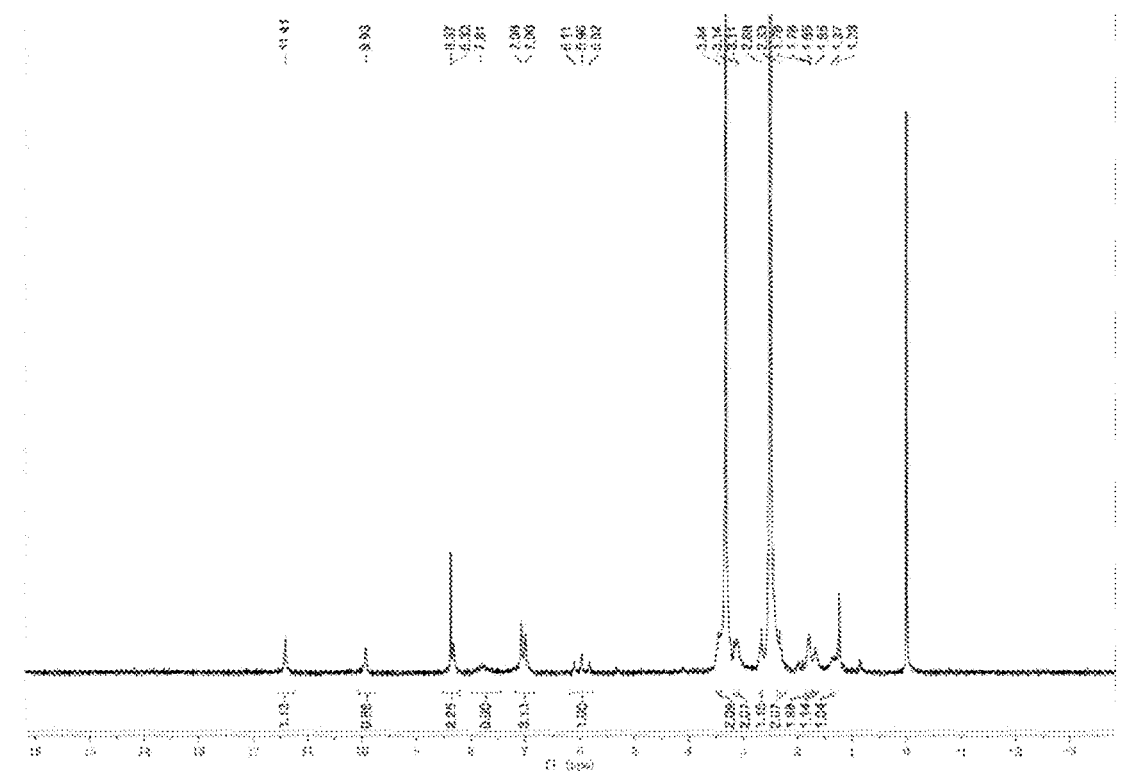
FIG. 2 Hydrogen nuclear magnetic resonance of a compound of Example 2.
Figures 3, 4:
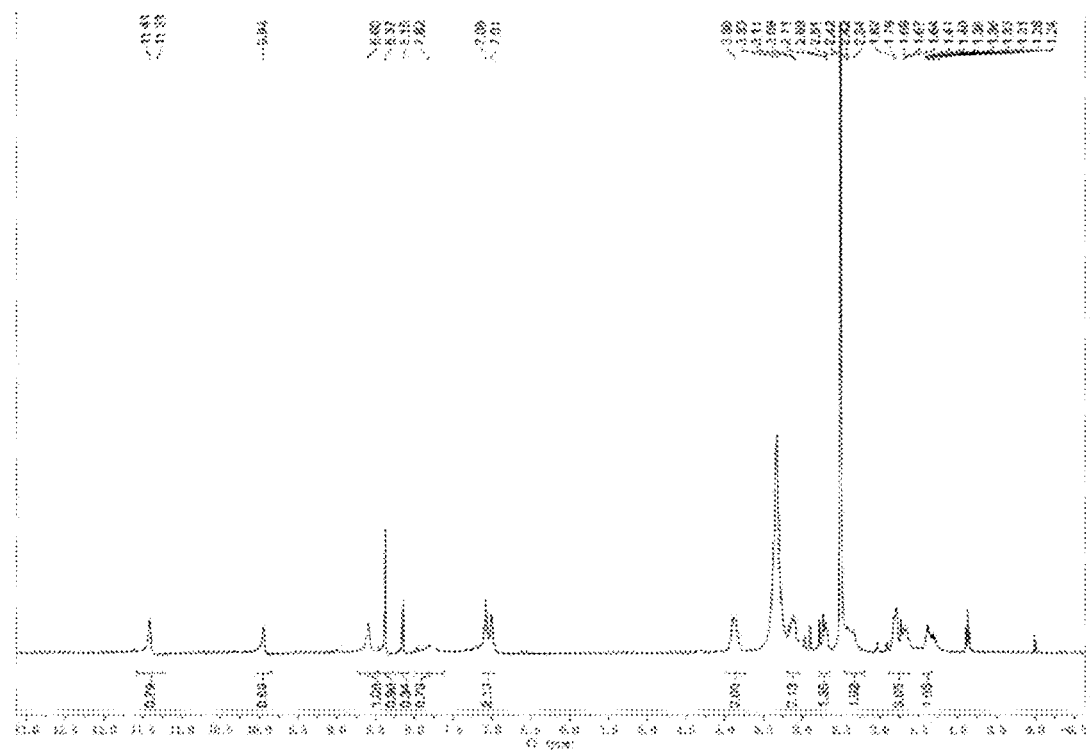
FIG. 3 Hydrogen nuclear magnetic resonance of a compound of Example 3.
FIG. 4 Hydrogen nuclear magnetic resonance of a compound of Example 4.
Figure 5:
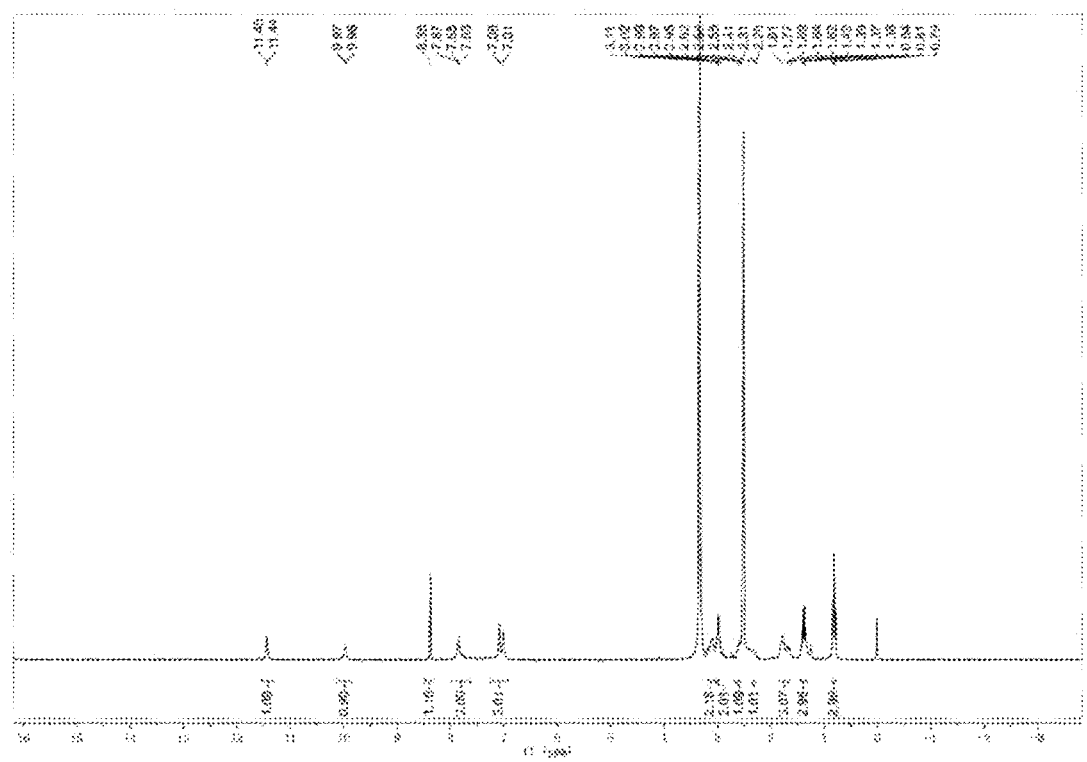
FIG. 5 Hydrogen nuclear magnetic resonance of a compound of Example 5.
Figure 6:
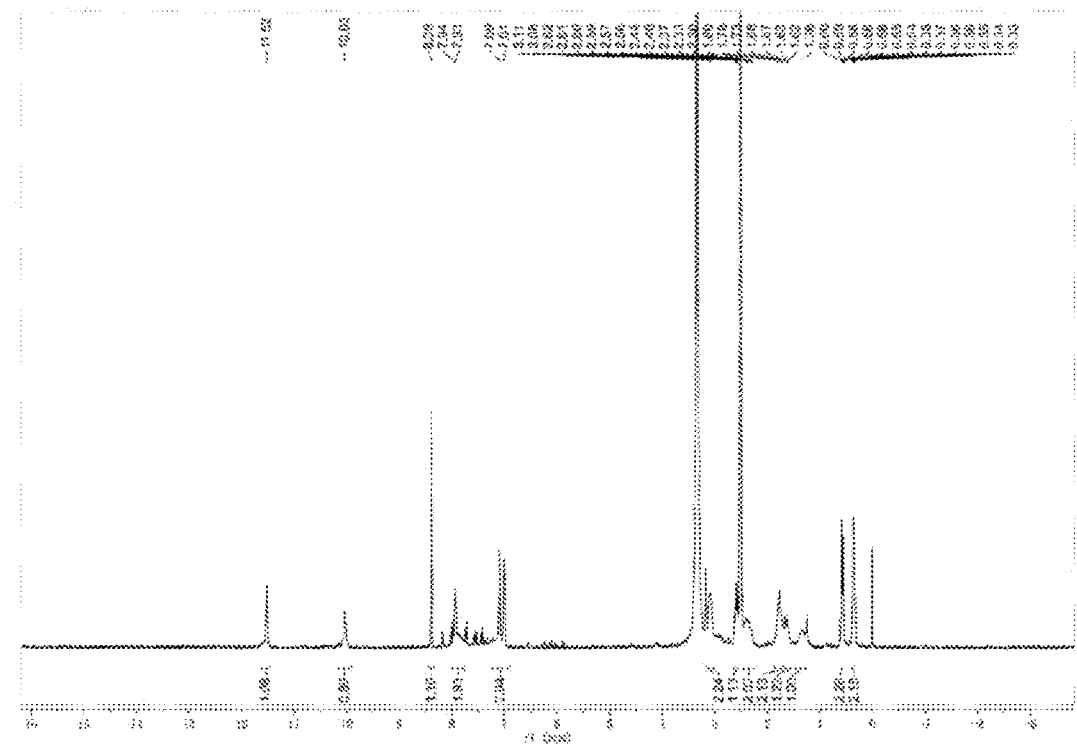
FIG. 6 Hydrogen nuclear magnetic resonance of a compound of Example 6.
Figure 7:
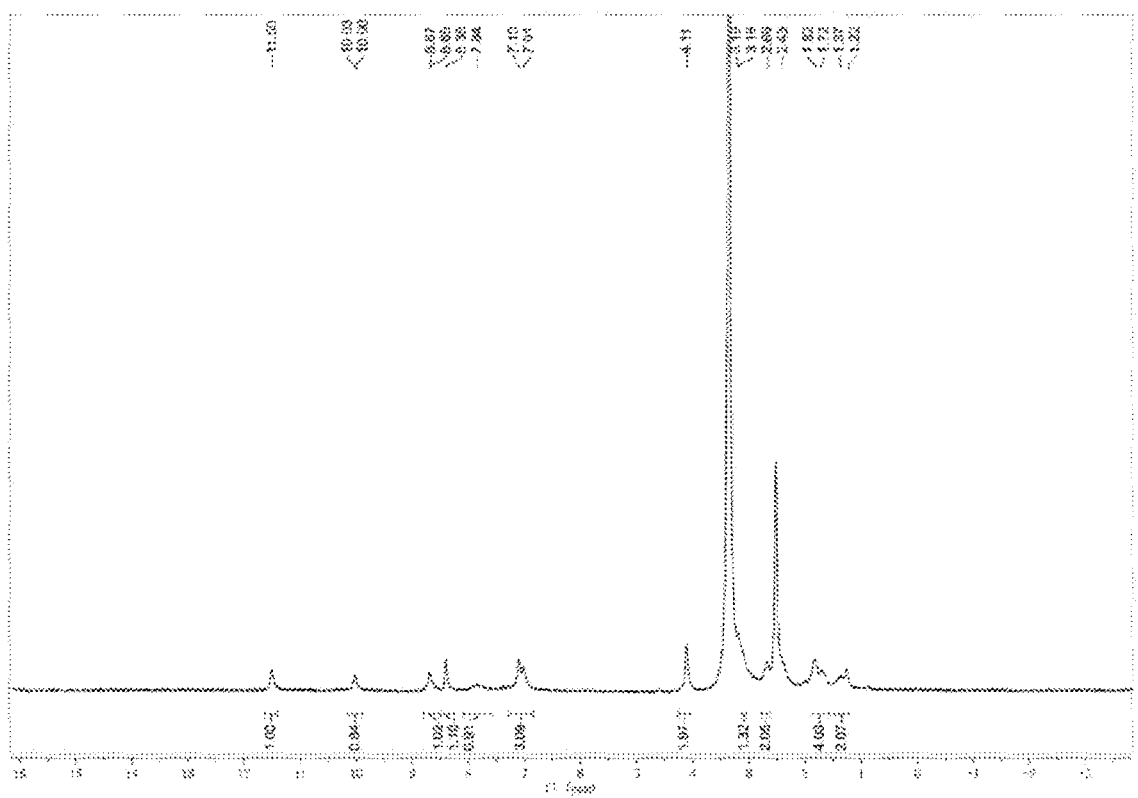
FIG. 7 Hydrogen nuclear magnetic resonance of a compound of Example 7.
Figure 8:
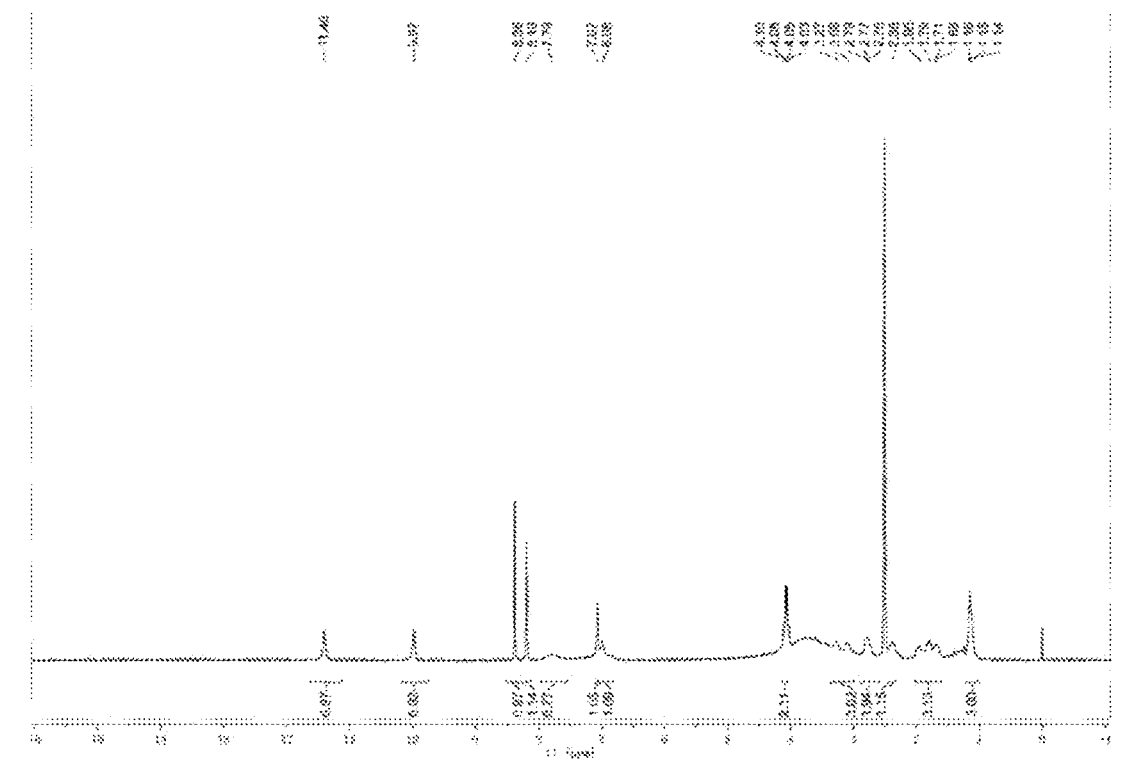
FIG. 8 Hydrogen nuclear magnetic resonance of a compound of Example 8.
Figures 9, 10:
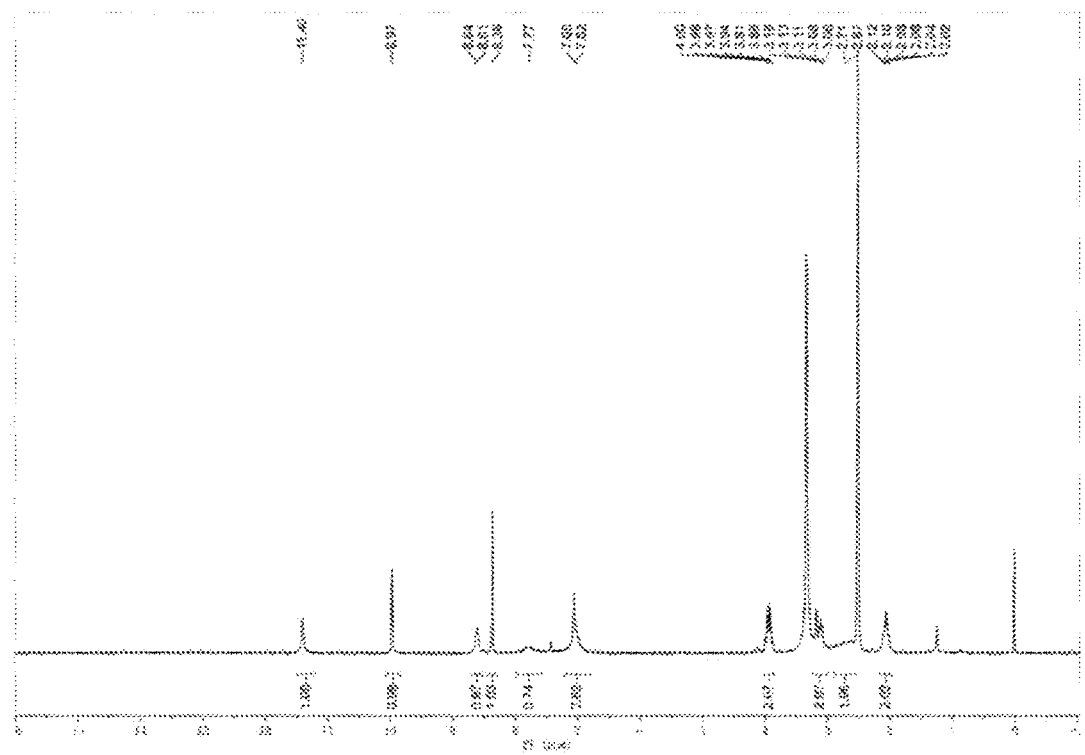
FIG. 9 Hydrogen nuclear magnetic resonance of a compound of Example 9.
FIG. 10 Hydrogen nuclear magnetic resonance of a compound of Example 10.
Figure 11:
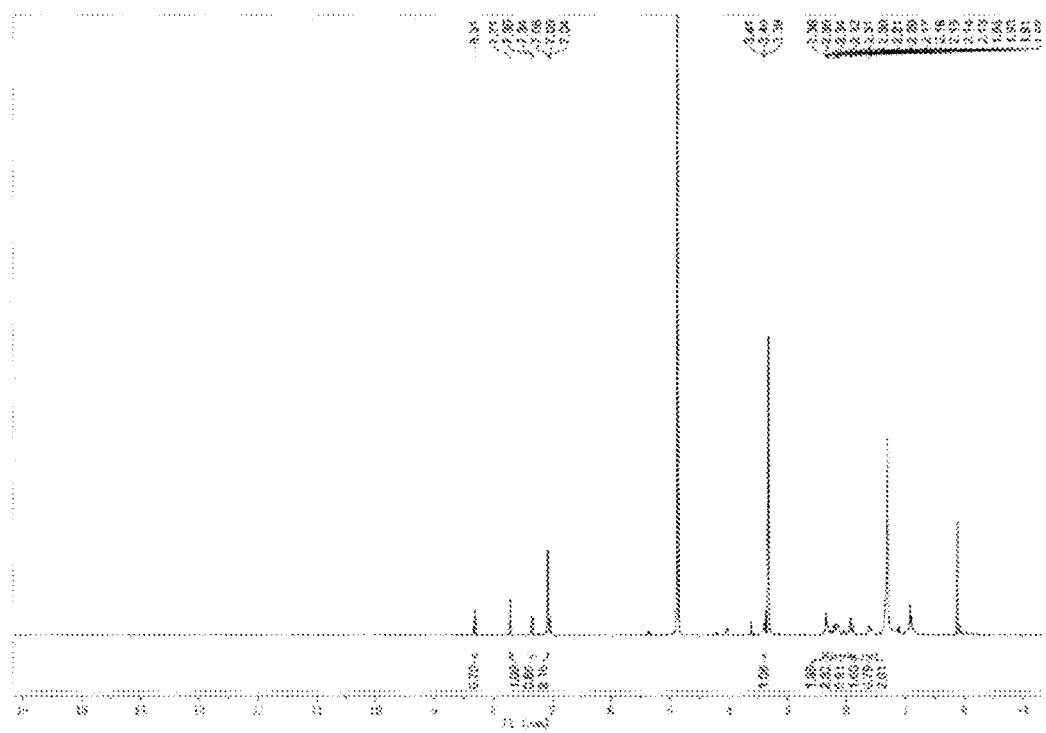
FIG. 11 Hydrogen nuclear magnetic resonance of a compound of Example 11.
Figure 12:
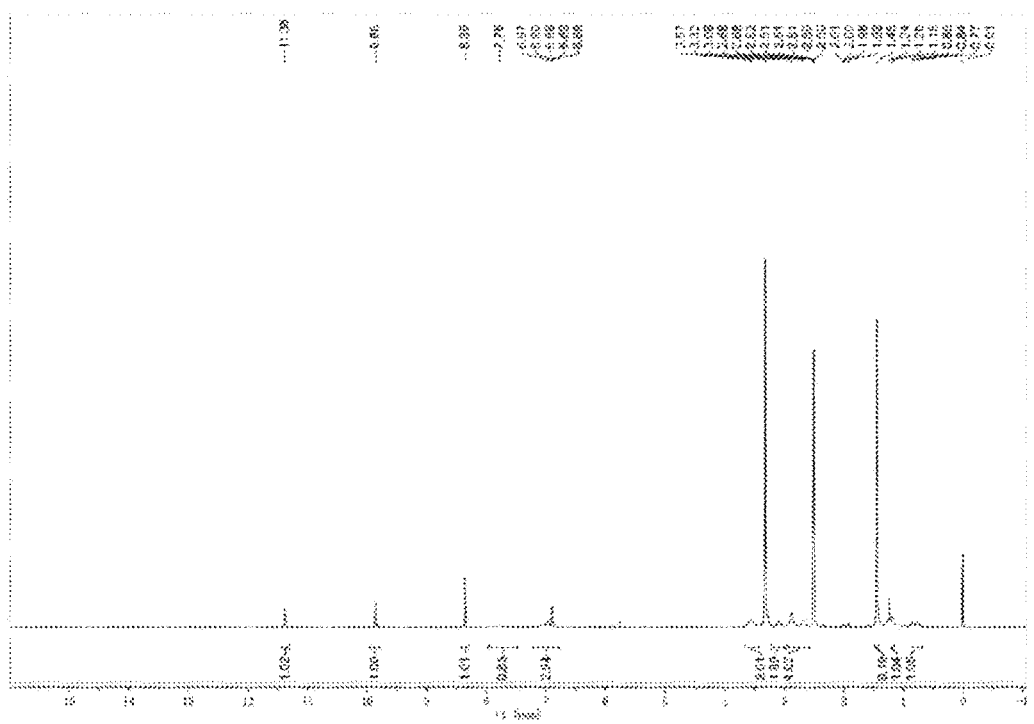
FIG. 12 Hydrogen nuclear magnetic resonance of a compound of Example 12.
Figure 13:
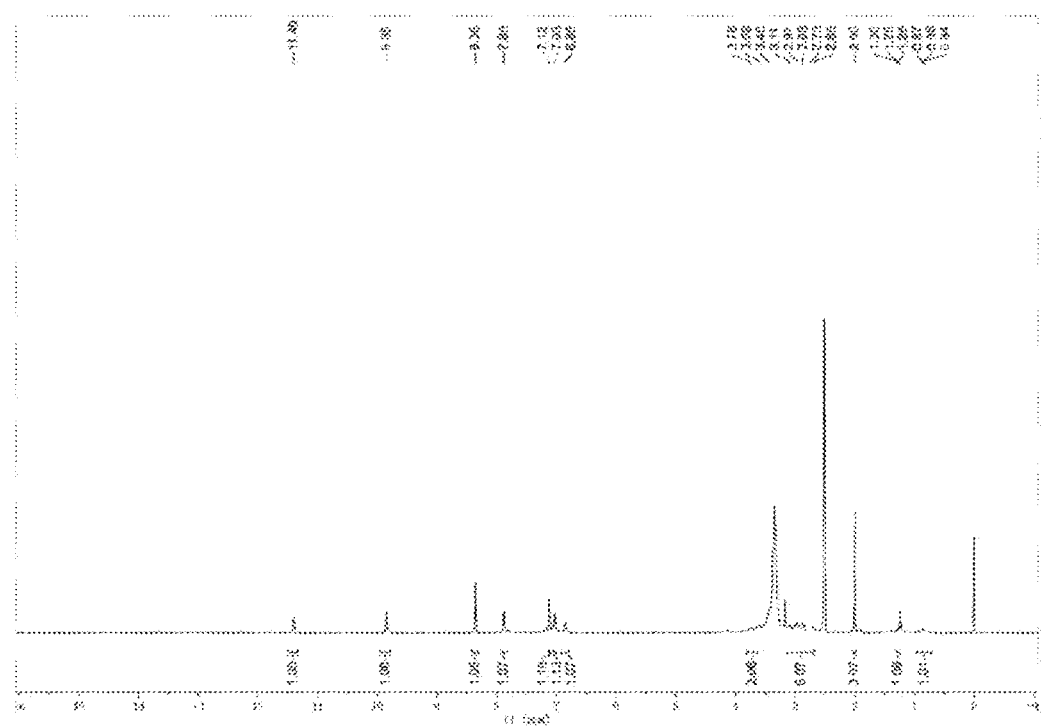
FIG. 13 Hydrogen nuclear magnetic resonance of a compound of Example 13.
Figure 14:
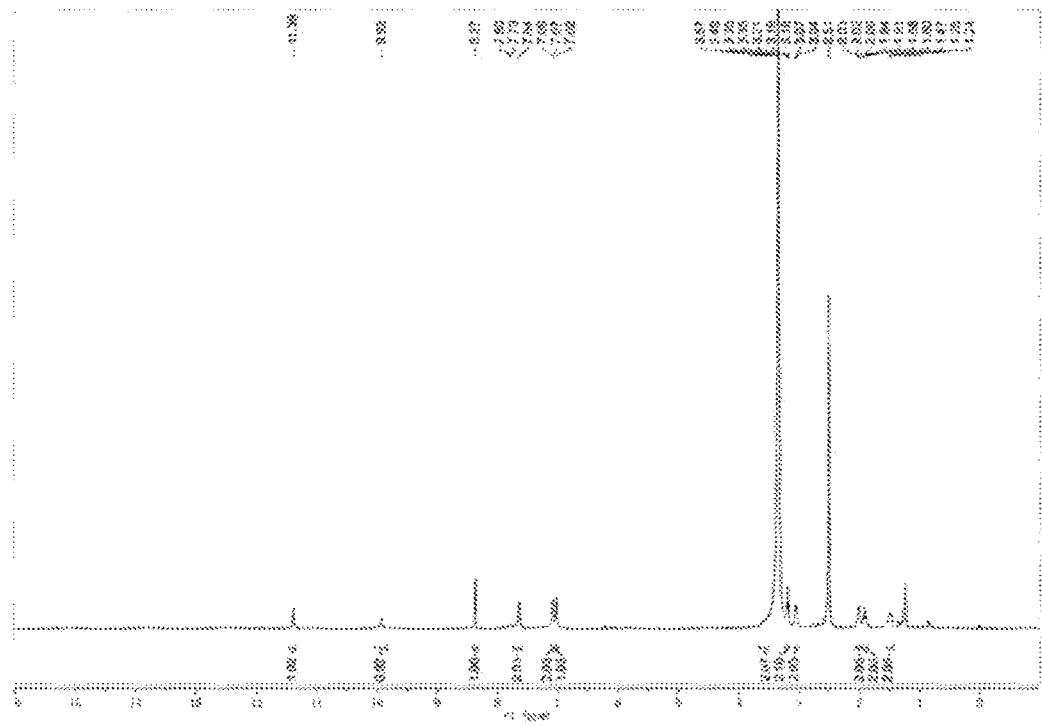
FIG. 14 Hydrogen nuclear magnetic resonance of a compound of Example 14.
Figure 15:
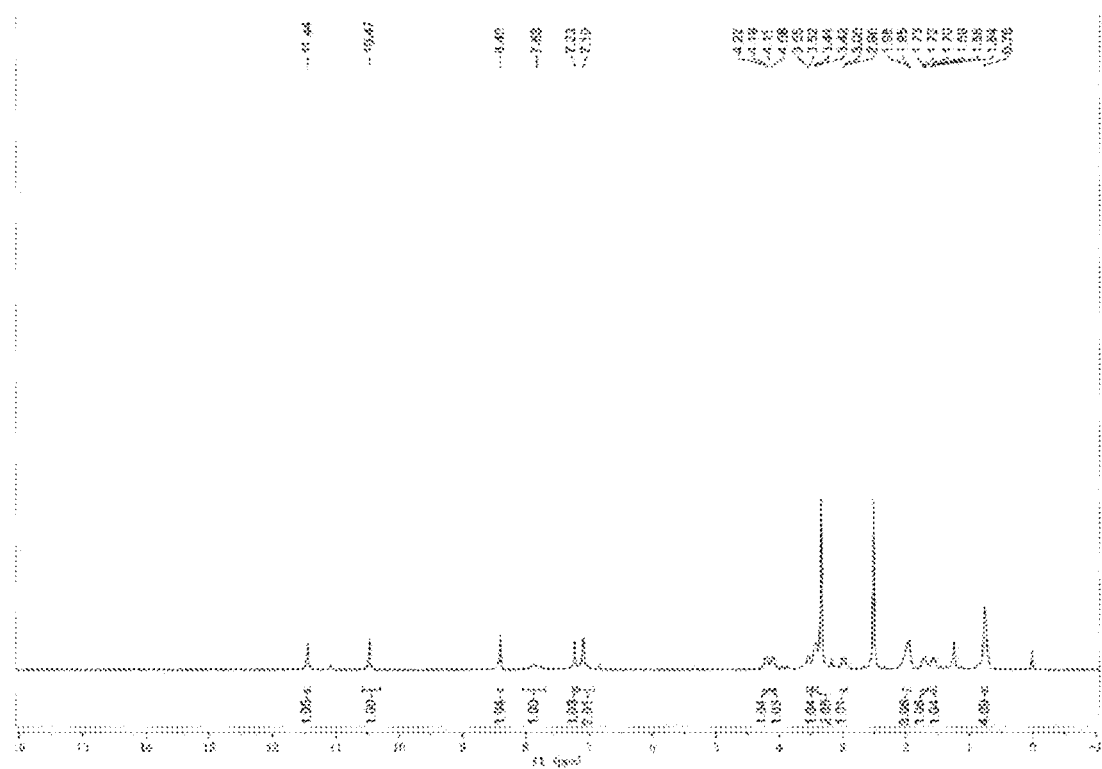
FIG. 15 Hydrogen nuclear magnetic resonance of a compound of Example 15.
Figure 16:
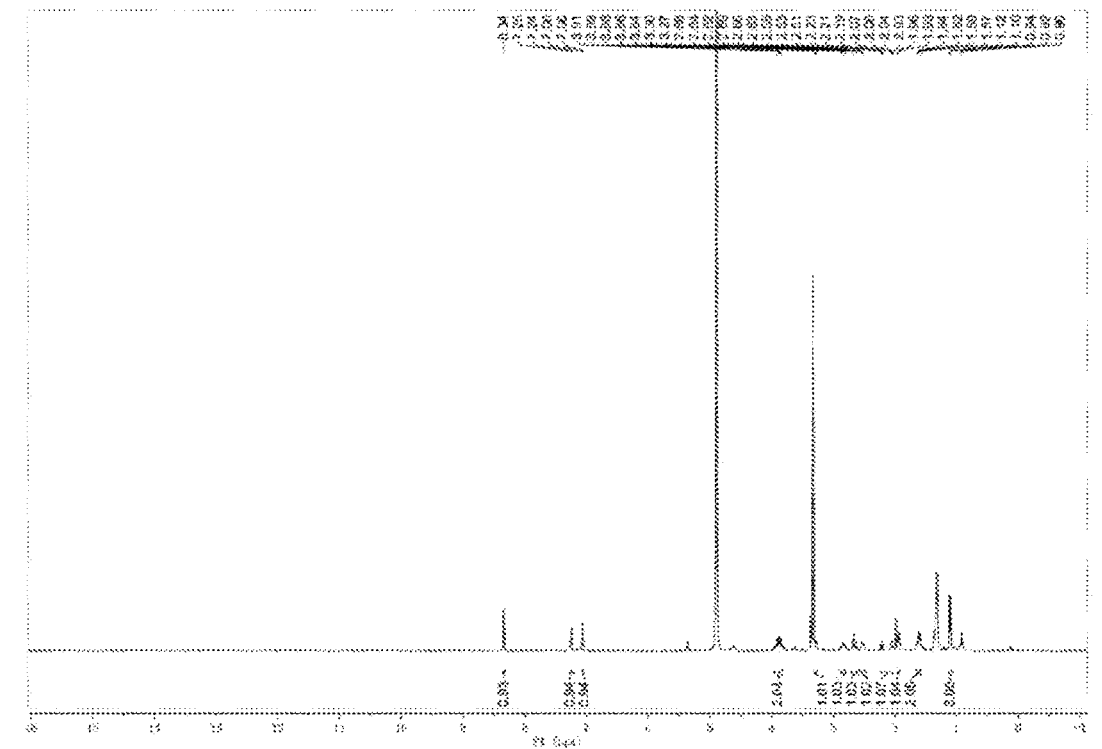
FIG. 16 Hydrogen nuclear magnetic resonance of a compound of Example 16.
Figure 17:
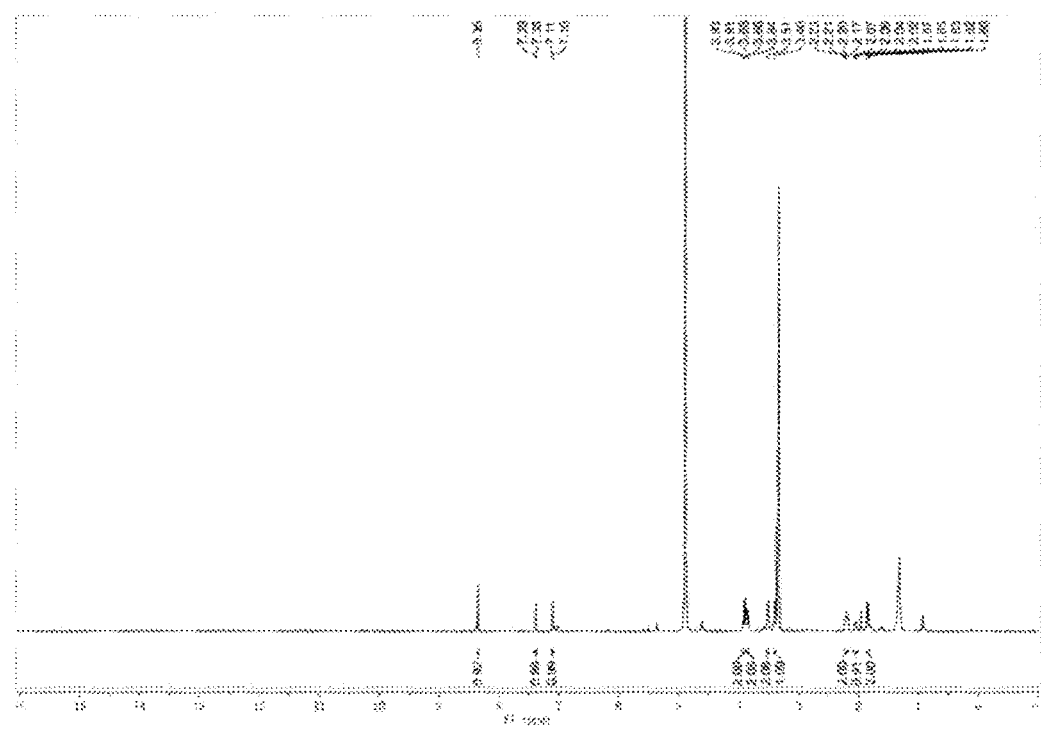
FIG. 17 Hydrogen nuclear magnetic resonance of a compound of Example 17.
Figure 18:
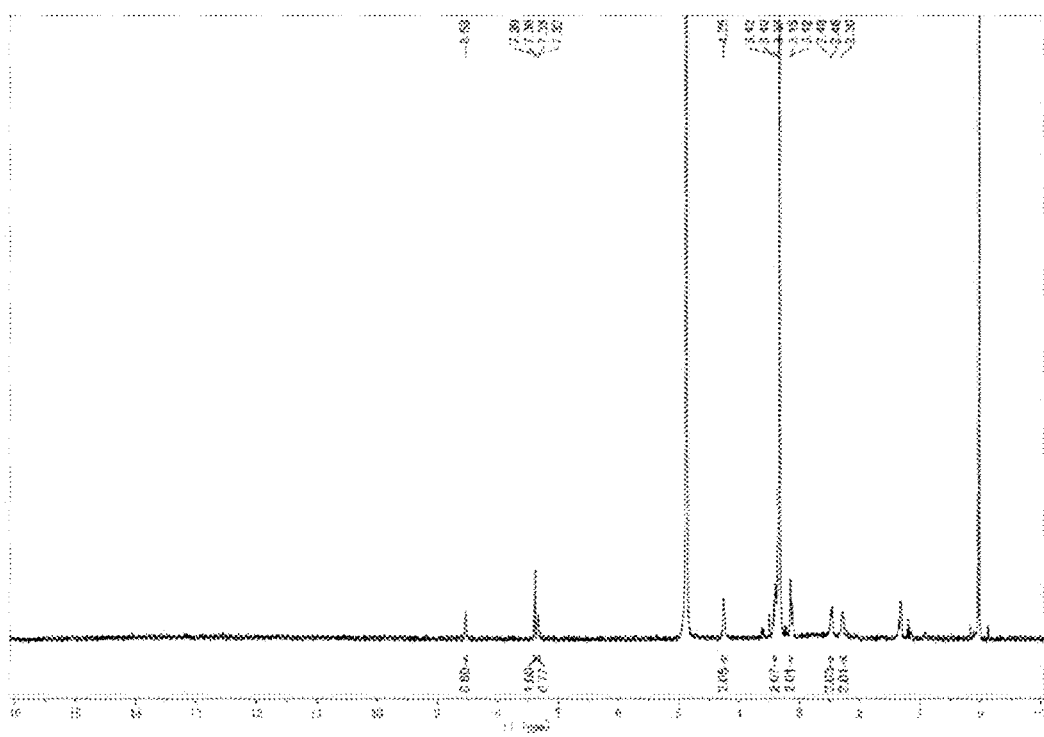
FIG. 18 Hydrogen nuclear magnetic resonance of a compound of Example 18.
Figure 19:
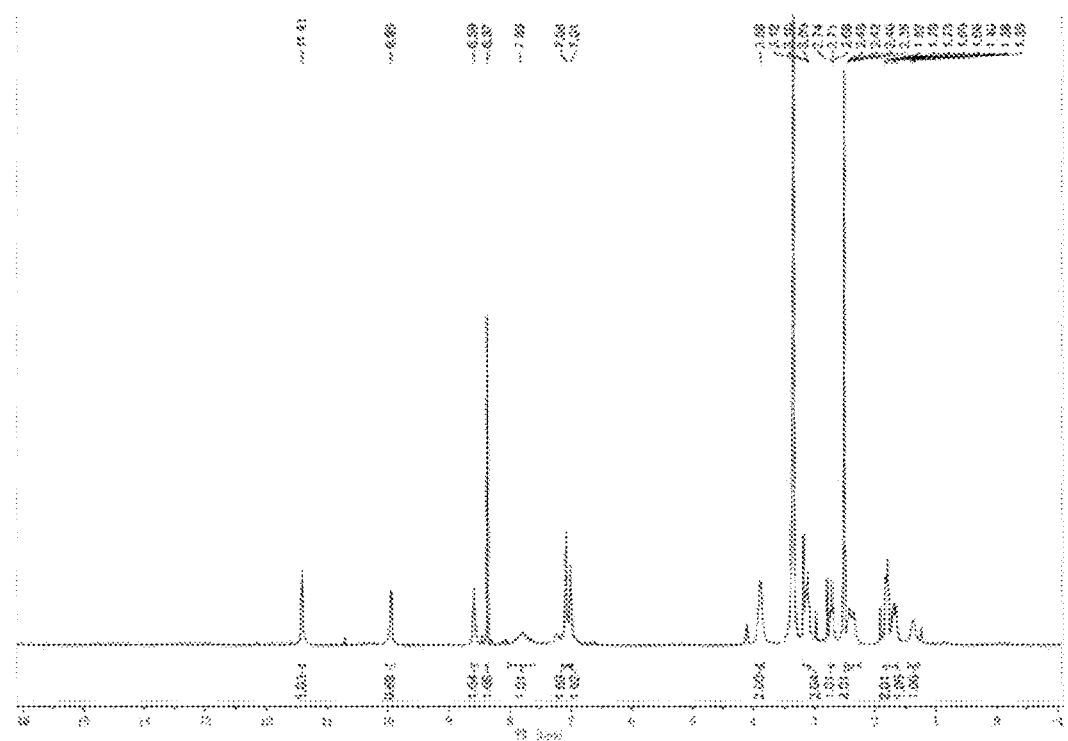
FIG. 19 Hydrogen nuclear magnetic resonance of a compound of Example 19.
Figure 20:
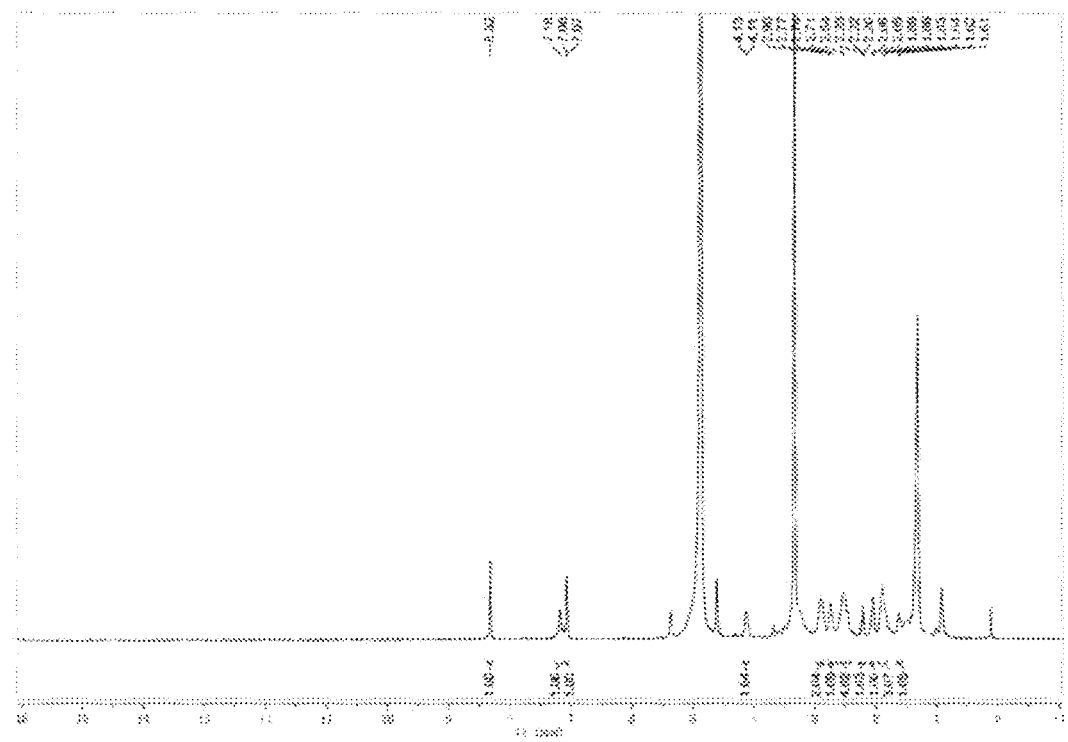
FIG. 20 Hydrogen nuclear magnetic resonance of a compound of Example 20.
Figure 21:
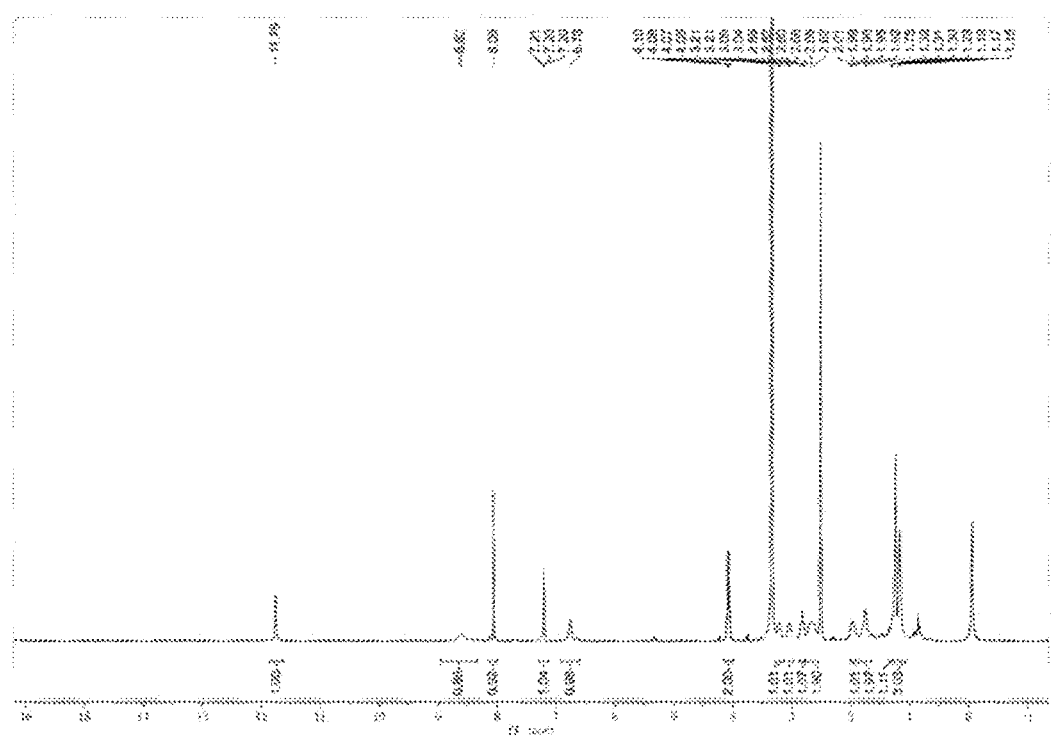
FIG. 21 Hydrogen nuclear magnetic resonance of a compound of Example 21.
Figure 22:
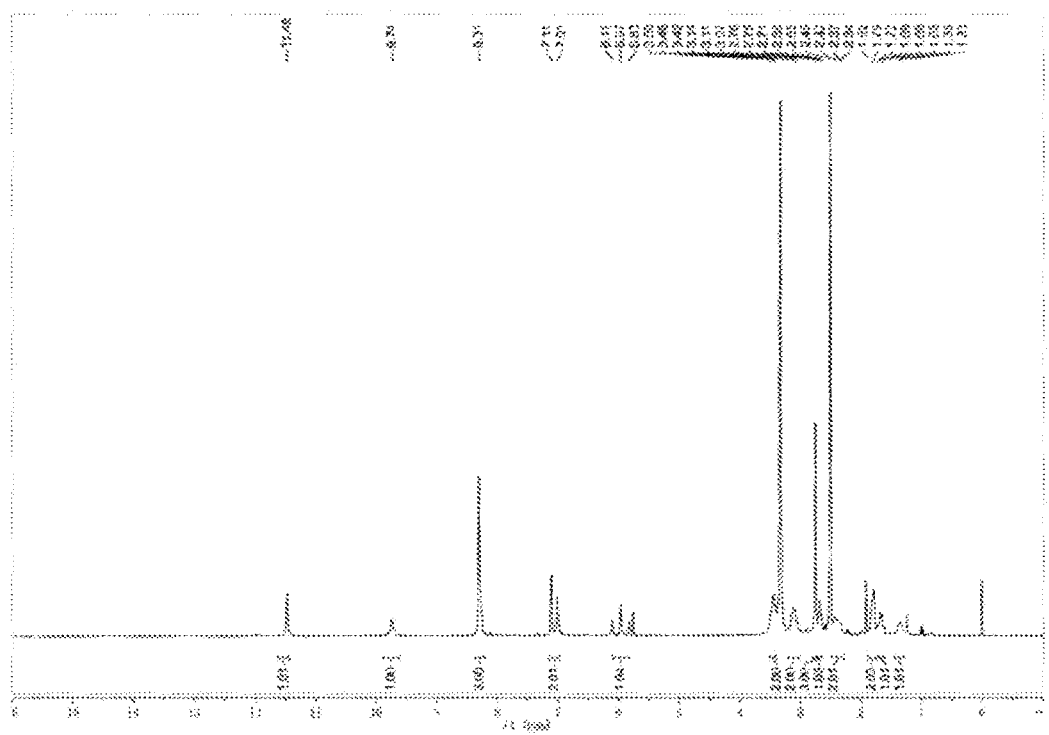
FIG. 22 Hydrogen nuclear magnetic resonance of a compound of Example 22.
Figure 23:
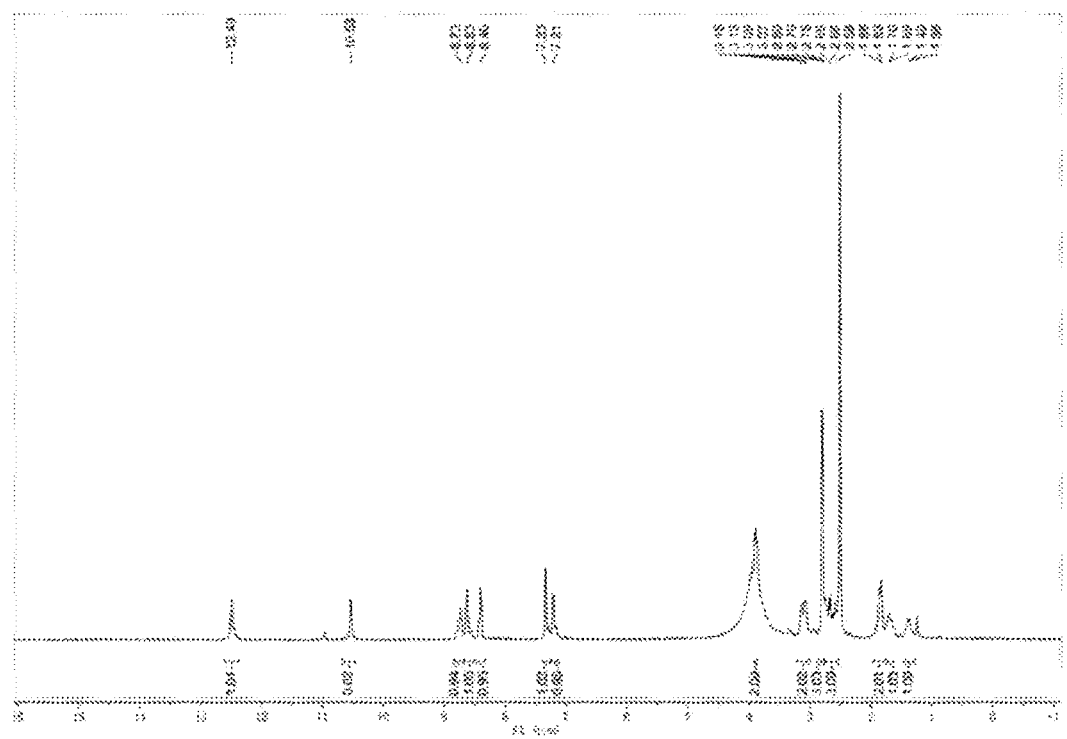
FIG. 23 Hydrogen nuclear magnetic resonance of a compound of Example 23.
Figure 24:
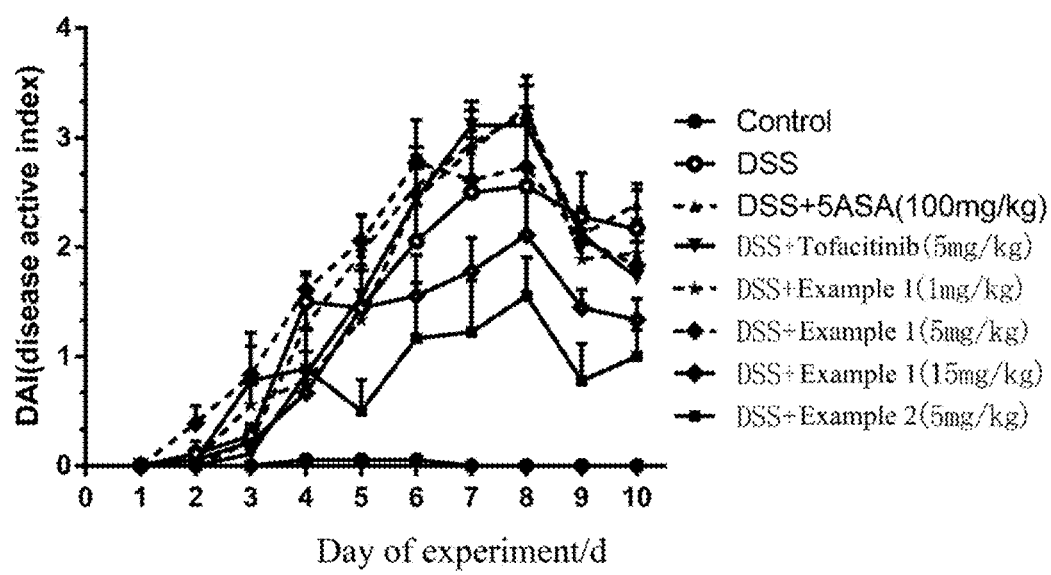
FIG. 24 Scoring results of the disease activity index (DAI) in a mouse DSS enteritis model.

The present invention is described below with reference to specific examples. Those skilled in the art will understand that these examples are only used to describe the present invention, and not limit the scope of the present invention in any manner.

All experimental methods in the following examples, unless otherwise specified, are conventional methods. Unless specifically stated, medicinal raw materials and reagent materials used in the examples below are commercially available products.

Example 1

Synthesis of (S)-4-(3-(2,2,2-trifluoroethylcarbamoyl)piperidine-1-amino)-1H-7-azaindole-5-carboxamide

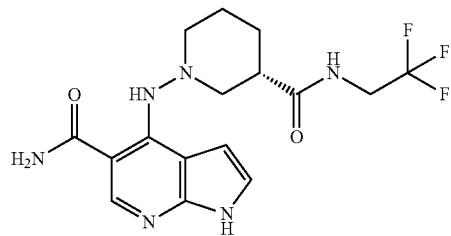 [SMILES: NC(=O)c1cnc2[nH]ccc2c1NN1CCC[C@H](C(=O)NCC(F)(F)F)C1]

Step 1: Synthesis of 4-chloro-1-(triisopropylsilyl)-7-azaindole

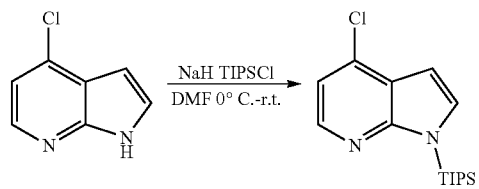

4-chloro-7-azaindole (100.00 g, 655.39 mmol) was dissolved in DMF (1.2 L) at room temperature, and cooled to 0° C. in an ice bath. NaH (39.47 g, 983.09 mmol) was added in batches and stirred for 1 hour at 0° C. after the addition was complete. Triisopropylchlorosilane (190.80 g, 983.09 mmol, TIPSCl for short) was dropwise added and warmed to room temperature. The reaction continued for 2 hours. The reaction was poured into 2 L of ice water, and extracted with petroleum ether (1 L×2). The organic phases were combined, washed with saturated brine (1 L×3), concentrated under reduced pressure to dryness, and subjected to column chromatography (PE:EA=1:0) to obtain 197.50 g of a colorless transparent liquid, with a yield of 97%.

Step 2: Synthesis of ethyl 4-chloro-1-(triisopropylsilyl)-7-azaindole-5-carboxylate

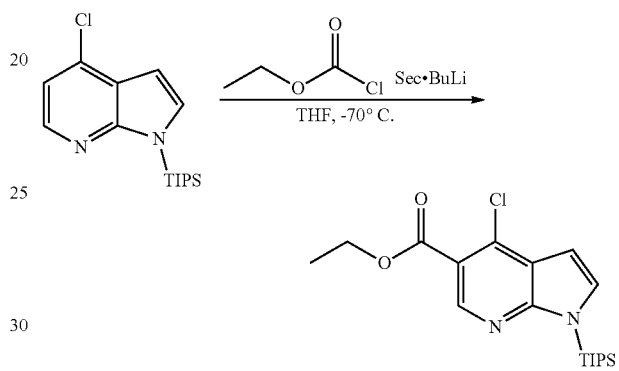

4-chloro-1-(triisopropylsilyl)-7-azaindole (20.00 g, 64.74 mmol) was dissolved in THF (100 ml) in a four-neck flask, and cooled to −75° C. Sec-butyl lithium (100 mL, 129.48 mol, Sec.BuLi) was dropwise added and stirred for 1 hour at −75° C. after the addition was complete. Chloroethyl chloroformate (17.80 g, 129.48 mmol) was added, and the reaction continued for 1 hour at −75° C. after the addition was complete. The reaction was poured into a saturated ammonium chloride solution. The layers were separated. The aqueous phase was extracted by adding ethyl acetate (100 mL). The organic phases were combined, washed with saturated brine, dried with anhydrous sodium sulfate, filtered, concentrated, and subjected to column chromatography (PE:EA=1:0-10:1) to obtain 23.15 g of a light-yellow liquid, with a yield of 94%.

Step 3: Synthesis of 4-chloro-7-azaindole-5-carboxylic acid

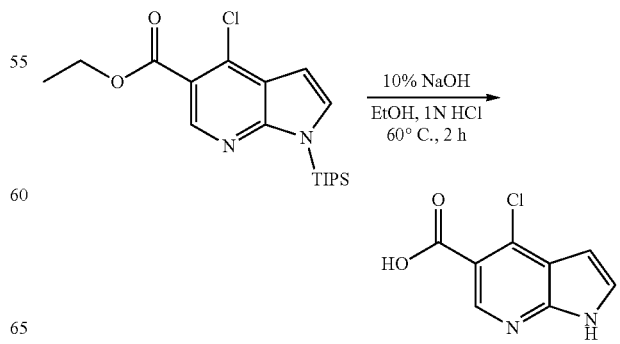

Ethyl 4-chloro-1-(triisopropylsilyl)-7-azaindole-5-carboxylate (12.94 g, 33.96 mmol) was added into a one-neck flask at room temperature. Ethanol (200 mL) and 10% sodium hydroxide (100 mL) were added, and the reaction continued for 2 hours at 60° C. after the addition was complete. Ethanol was evaporated off under reduced pressure. The aqueous phase was adjusted with 1N dilute hydrochloric acid to pH=4 in an ice bath. A large amount of white solid was precipitated and filtered, and the filter cake was dried to obtain 8.60 g of a white solid, with a yield of 77%.

Step 4: Synthesis of 4-chloro-7-azaindole-5-carboxamide

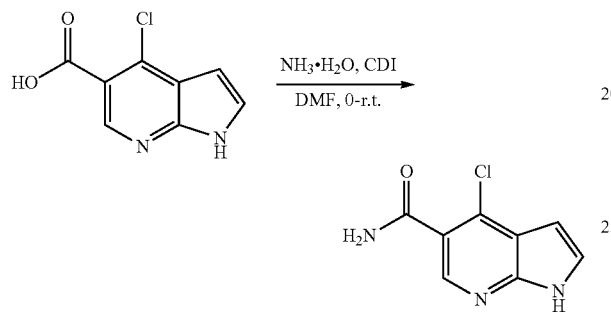

4-chloro-7-azaindole-5-carboxylic acid (7.00 g, 35.60 mmol) was added into a four-neck flask, 100 mL of DMF was added, and carbonyl diimidazole (8.72 g, 53.41 mmol, CDI) was added with stirring. Stirring was carried out for 1.5 hours at room temperature. Ammonia water (9.34 g, 142.40 mmol) was dropwise added at 0° C. It was naturally warmed to room temperature, and reacted with stirring for 2 hours. 100 mL of EA was added into the reaction and a large amount of white solid was precipitated, and filtered after standing. The filter cake was washed with water and dried to obtain 5.34 g of a grey solid, with a yield of 76%.

Step 5: Synthesis of ethyl (S)-1-nitrosopiperidine-3-carboxylate

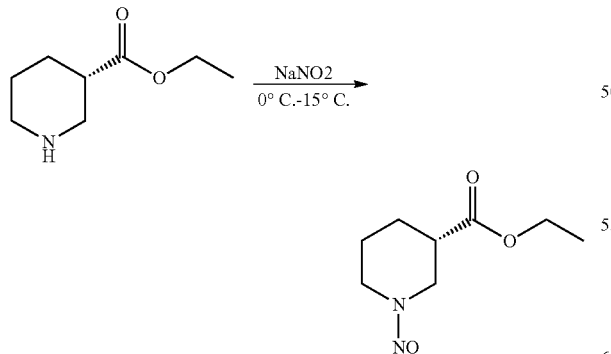

Ethyl (S)-3-piperidine carboxylate (10.00 g, 0.064 mol) was added into a mixed solution of glacial acetic acid (100 mL) and water (40 mL) at room temperature, and cooled to 0° C. Then, 20 mL of an aqueous solution with dissolved sodium nitrite (8.78 g, 0.13 mol) was dropwise added. The reaction continued with stirring for 1 h at 0° C. and for another 2 h at room temperature. 200 mL of water was added into the reaction, and extraction was performed with ethyl acetate (200 mL×3). The organic phases were combined, washed with saturated brine, concentrated under reduced pressure, and directly applied to the next step.

Step 6: Synthesis of ethyl (S)-1-aminopiperidine-3-carboxylate hydrochloride

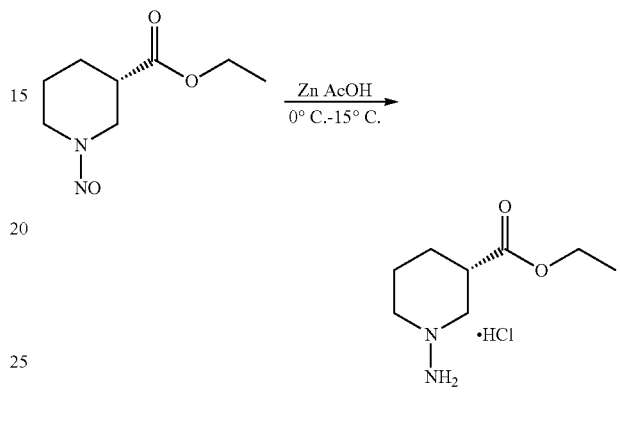

Ethyl (S)-1-nitrosopiperidine-3-carboxylate (11.83 g, 0.064 mol) was dissolved in methanol (100 mL). Zn powder (10.40 g, 0.16 mol) was added and cooled to −5° C. Glacial acetic acid (50 mL) was slowly and dropwise added, and after the addition was complete, the reaction continued with stirring for 0.5 h at 0° C. and for another 2 h at room temperature. The reaction was filtered, the filter cake was rinsed with 100 mL of methanol, and the filtrate was evaporated to dryness. A solution of hydrochloric acid in ethanol was added into the residue and stirred for 0.5 h. The solvent was removed by evaporation to obtain 13.27 g of a yellow oily substance. The yield of crude products of steps 5 and 6 was 100%.

Step 7: Synthesis of ethyl (S)-1-(5-formamido-1H-7-azaindole-4-amino)piperidine-3-carboxylate

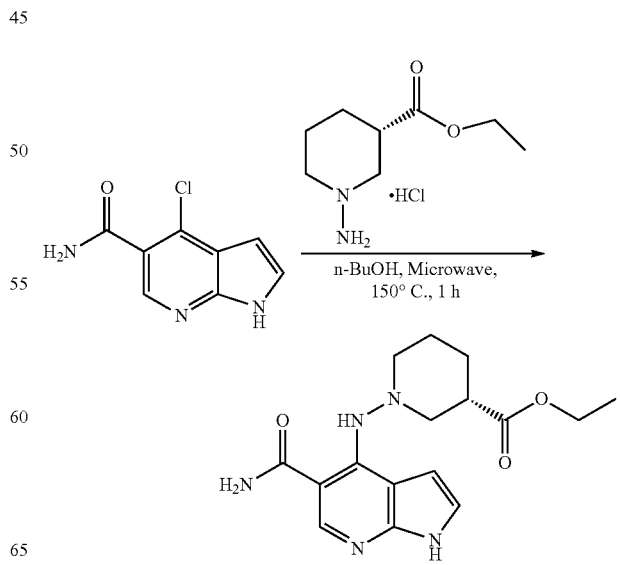

4-chloro-7-azaindole-5-carboxamide (1.00 g, 5.12 mmol) and ethyl (S)-1-aminopiperidine-3-carboxylate hydrochloride (2.14 g, 10.24 mmol) were added into a microwave tube, 20 mL of n-butyl alcohol was added, and the microwave reaction continued for 1 h at 150° C. The reaction was evaporated under reduced pressure to dryness, and subjected to column chromatography (dichloromethane/methanol system) to obtain 0.80 g of a light-yellow gel-like crude product, with a yield of 47.3%. $^1$H NMR (300 MHz, DMSO-$d_6$) δ 11.40 (s, 1H), 9.97 (s, 1H), 8.38 (s, 1H), 8.19 (s, 1H), 7.79 (s, 1H), 7.07 (s, 1H), 6.98 (s, 1H), 4.06 (q, J=7.0 Hz, 2H), 3.17 (d, J=56.4 Hz, 3H), 2.88-2.64 (m, 2H), 2.38 (s, 1H), 2.07-1.59 (m, 3H), 1.22-0.93 (m, 3H). MS (ESI) m/z: 332 [M+H]$^+$.

Step 8: Synthesis of (S)-1-(5-formamido-1H-7-azaindole-4-amino)piperidine-3-carboxylic acid

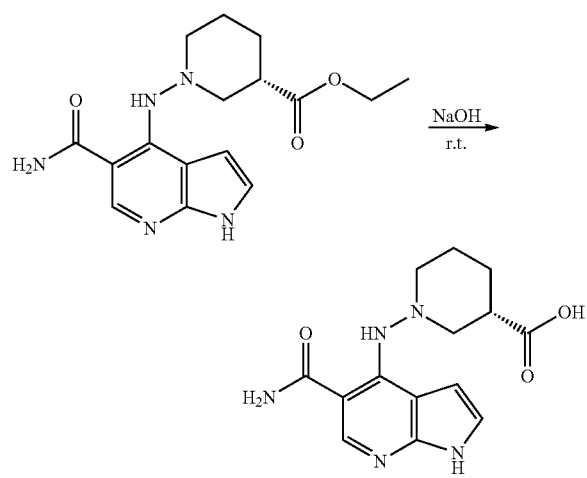

Ethyl (S)-1-(5-formamido-1H-7-azaindole-4-amino)piperidine-3-carboxylate (0.70 g, 2.11 mmol) was dissolved in methanol at room temperature, a 3N NaOH solution was dropwise added, and the reaction continued for 3 h at 23° C. The organic solvent was removed by evaporation, the aqueous phase was adjusted using 1N dilute hydrochloric acid to about pH=4, and evaporated under reduced pressure to dryness. The residual solid was dissolved by adding methanol, the inorganic salt was removed by filtration, and the methanol was removed by evaporation to obtain 0.52 g of a light-yellow solid, with a yield of 81.3%.

Step 9: Synthesis of (S)-4-(3-(2,2,2-trifluoroethylcarbamoyl)piperidine-1-amino)-1H-7-azaindole-5-carboxamide

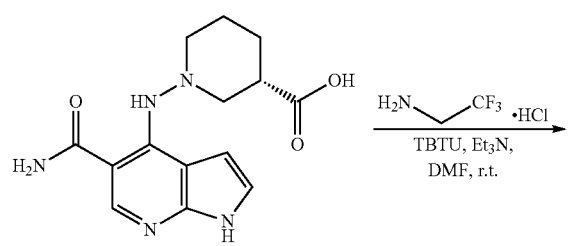

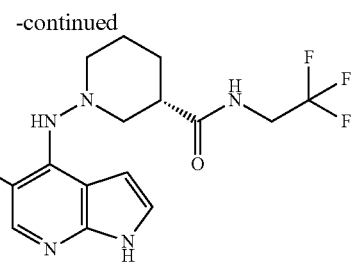

(S)-1-(5-formamido-1H-7-azaindole-4-amino)piperidine-3-carboxylic acid (0.25 g, 0.82 mmol). 2,2,2-Trifluoroethanamine hydrochloride (0.17 g, 1.23 mmol) and O-(Benzotriazol-1-yl)-N,N,N',N'-tetramethyluronium tetrafluoroborate (0.40 g, 1.23 mmol, TBTU) were added into a one-neck flask, 5 mL of DMF was added, and triethylamine (0.48 g, 4.75 mmol) was added after stirring up. After the addition was complete, stirring was carried out overnight at room temperature. 10 mL of water was added into the reaction, and the reaction was extracted with a mixed solvent of DCM:MeOH=5:1 (10 mL×5). The organic phases were combined, washed with saturated brine, evaporated under reduced pressure to dryness, and subjected to column chromatography (dichloromethane/methanol system) to obtain 0.022 g of a light-yellow solid, with a yield of 10%. $^1$H NMR (400 MHz, DMSO-$d_6$) δ 11.42 (br, 1H), 9.95 (br, 1H), 8.59 (br, 1H), 8.37 (s, 1H), 8.15 (s, 1H), 7.78 (br, 1H), 7.04 (m, 2H), 3.87 (br, 2H), 3.11 (m, 2H), 2.71 (m, 1H), 2.37 (m, 2H), 1.82 (m, 2H), 1.67 (m, 1H), 1.34 (m, 1H). MS (ESI) m/z: 385 [M+H]$^+$.

Example 2

Synthesis of (S)-4-(3-(2,2-difluoroethylcarbamoyl)piperidine-1-amino)-1H-7-azaindole-5-carboxamide

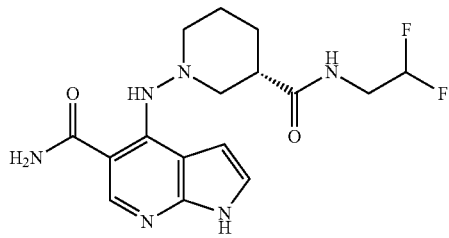 [SMILES: NC(=O)c1cnc2[nH]ccc2c1NN1CCC[C@H](C(=O)NCC(F)F)C1]

Step 1: Synthesis of tert-butyl (S)-3-((2,2-difluoroethyl)carbamoyl)piperidine-1-carboxylate

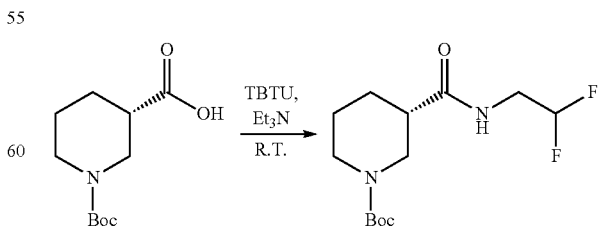

(S)-1-(tert-butoxycarbonyl)piperidine-3-carboxylic acid (15.00 g, 65.40 mmol) was dissolved in DCM (400 mL) at room temperature, triethylamine (16.50 g, 163.50 mmol)

and TBTU (25.20 g, 78.50 mol) were added, and the reaction continued for 1 h. Then, the reaction was transferred in an ice bath, and 2,2-difluoroethylamine hydrochloride (10.00 g, 85.00 mmol) was slowly and dropwise added at 0° C. After the addition was complete, stirring was carried out for 1 h at 0° C., and the reaction continued for 5 hours at room temperature and was stopped. The reaction was concentrated, diluted with water (200 mL), and extracted three times with ethyl acetate (150 mL). The organic phases were combined, washed three times with 100 mL of saturated brine, concentrated, and subjected to column chromatography (PE/EA system) to obtain 16.06 g of a colorless transparent liquid, with a yield of 84%. MS (ESI) m/z: 237.1 [M+H–56]⁺.

Step 2: Synthesis of (S)—N-(2,2-difluoroethyl)piperidine-3-carboxamide hydrochloride

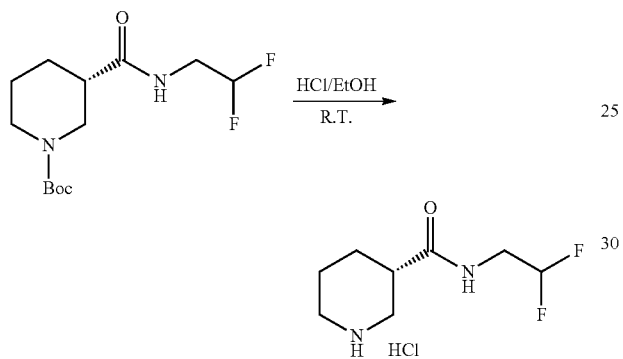

Tert-butyl (S)-3-((2,2-difluoroethyl)carbamoyl)piperidine-1-carboxylate (16.06 g, 54.94 mmol) was dissolved in ethanol (150 mL), 35% HCl/EtOH (30 mL) was slowly and dropwise added at normal temperature, and the reaction continued for 3 hours and was stopped. The solvent was evaporated off under reduced pressure to obtain 11.43 g of a white solid, with a yield of 91%. MS (ESI) m/z: 193.1 [M+H]⁺.

Step 3: Synthesis of (S)—N-(2,2-difluoroethyl)-1-nitrosopiperidine-3-carboxamide

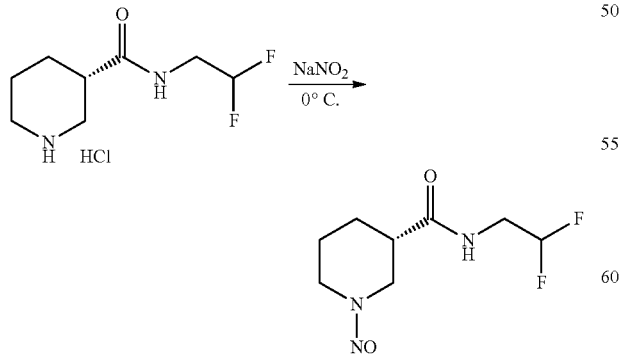

(S)—N-(2,2-difluoroethyl)piperidine-3-carboxamide hydrochloride (11.43 g, 49.98 mmol) was dissolved in acetic acid (100 mL) at room temperature, 50 mL of an aqueous solution with dissolved sodium nitrite (4.49 g, 65.00 mmol) was slowly added at 0° C. After dropwise addition was complete, the reaction continued for 1 hour at 0° C., and then continued overnight at normal temperature. After the reaction was complete, the reaction was added with water (100 mL), and extracted three times with ethyl acetate (80 mL). The organic phases were combined, washed with saturated aqueous solution (80 mL) of sodium carbonate, dried with anhydrous sodium sulfate, and concentrated. The product was subjected to column chromatography (PE/EA) using silica gel to obtain 9.80 g of a white solid, with a yield of 89%. MS (ESI) m/z: 222.1 [M+H]⁺.

Step 4: Synthesis of (S)-1-amino-N-(2,2-difluoroethyl)piperidine-3-carboxamide hydrochloride

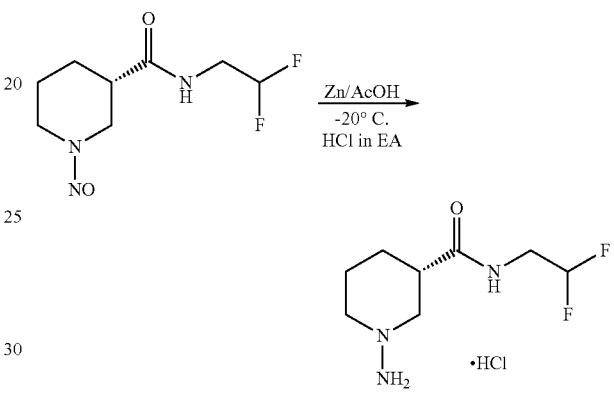

(S)—N-(2,2-difluoroethyl)-1-nitrosopiperidine-3-carboxamide (9.80 g, 44.30 mmol) was dis solved in methanol (40 mL), and zinc powder (8.70 g, 132.90 mmol) was slowly added at room temperature, and cooled to –20° C. and stirred for 10 minutes under nitrogen protection. Acetic acid (50 mL) was slowly and dropwise added at –20° C., and the reaction continued for 2 hours under nitrogen protection and was stopped. A solution of hydrochloric acid in ethyl acetate was added and stirred for 1 hour for salt formation. The reaction was evaporated under reduced pressure to dryness, and stored. The reaction was filtered, and the filtrate was subjected to column chromatography (DCM/MeOH) directly using silica gel to obtain 8.60 g of a white solid. The white solid was added with a solution of hydrochloric acid in ethyl acetate, and stirred for 1 hour for salt formation. It was evaporated under reduced pressure to dryness, and stored. MS (ESI) m/z: 208.1 [M+H]⁺.

Step 5: Synthesis of (S)-4-(3-(2,2-difluoroethylcarbamoyl)piperidine-1-amino)-1H-7-azaindole-5-carboxamide

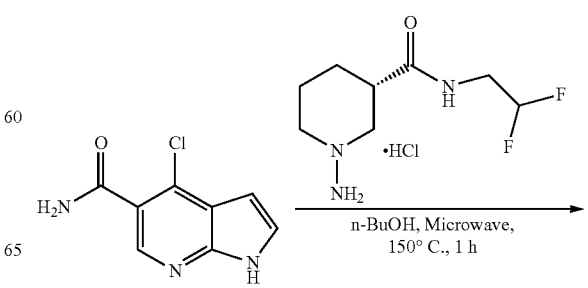

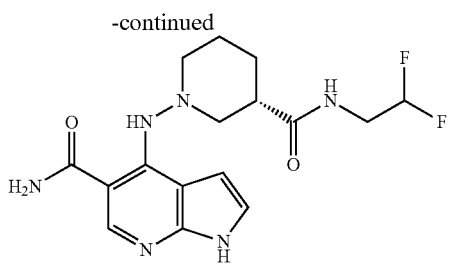

4-chloro-7-azaindole-5-carboxamide (0.10 g, 0.51 mmol) and (S)-1-amino-N-(2,2-difluoro ethyl)piperidine-3-carboxamide hydrochloride (0.25 g, 1.02 mmol) were added into a microwave tube, 2 mL of n-butyl alcohol was added, and the microwave reaction continued for 1 h at 150° C. The reaction was filtered, and the filtrate was rotary evaporated to dryness, and subjected to column chromatography (dichloromethane/methanol system) to obtain 0.014 g of a light-yellow solid, with a yield of 7.5%. $^1$H NMR (400 MHz, DMSO-$d_6$) δ 11.41 (br, 1H), 9.93 (br, 1H), 8.37 (s, 1H), 8.32 (br, 1H), 7.81 (br, 1H), 7.04 (m, 3H), 5.96 (t, J=57.5 Hz, 1H), 3.44 (m, 2H), 3.12 (m, 2H), 2.68 (m, 1H), 2.33 (m, 2H), 1.78 (m, 2H), 1.65 (m, 11H), 1.32 (m, 1H). MS (ESI) m/z: 367 [M+H]$^+$.

Example 3

Synthesis of (R)-4-(3-(2,2,2-trifluoroethylcarbamoyl)piperidine-1-amino)-1H-7-azaindole-5-carboxamide

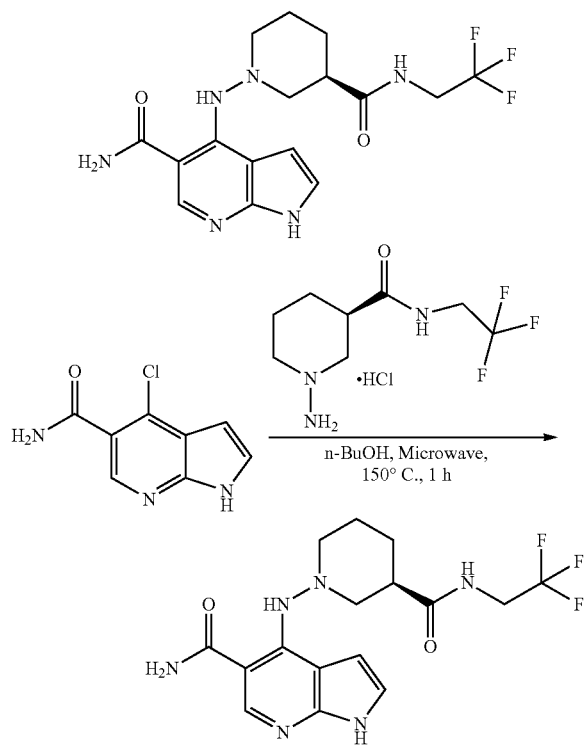

An intermediate (R)-1-amino-N-(2,2,2-trifluoroethyl)piperidine-3-carboxamide hydrochloride was synthesized with reference to the preparation method of the intermediate (S)-1-amino-N-(2,2-difluoroethyl)piperidine-3-carboxamide hydrochloride in Example 2, by replacing (S)-1-(tert-butoxycarbonyl)piperidine-3-carboxylic acid in Step 1 of Example 2 with (R)-1-(tert-butoxycarbonyl)piperidine-3-carboxylic acid, and replacing 2,2-difluoroethylamine hydrochloride with trifluoroethylamine hydrochloride.

4-chloro-7-azaindole-5-carboxamide (0.10 g, 0.51 mmol) and (R)-1-amino-N-(2,2,2-trifluoroethyl)piperidine-3-carboxamide hydrochloride (0.27 g, 1.02 mmol) were added into a micro wave tube, 2 mL of n-butyl alcohol was added, and the microwave reaction continued for 1 h at 150° C. The reaction was filtered, and the filtrate was rotary evaporated to dryness, and subjected to column chromatography (dichloromethane/methanol system) to obtain 0.015 g of a light-yellow solid powder, with a yield of 7.6%. $^1$H NMR (400 MHz, DMSO-$d_6$) δ 11.41 (br, 1H), 9.94 (br, 1H), 8.60 (br, 1H), 8.37 (s, 1H), 8.15 (br, 1H), 7.82 (br, 1H), 7.04 (m, 2H), 3.88 (br, 2H), 3.10 (m, 2H), 2.71 (m, 1H), 2.38 (m, 2H), 1.82 (m, 2H), 1.67 (m, 1H), 1.37 (m, 1H). MS (ESI) m/z: 385 [M+H]$^+$.

Example 4

Synthesis of (R)-4-(3-(2,2-difluoroethylcarbamoyl)piperidine-1-amino)-1H-7-azaindole-5-carboxamide

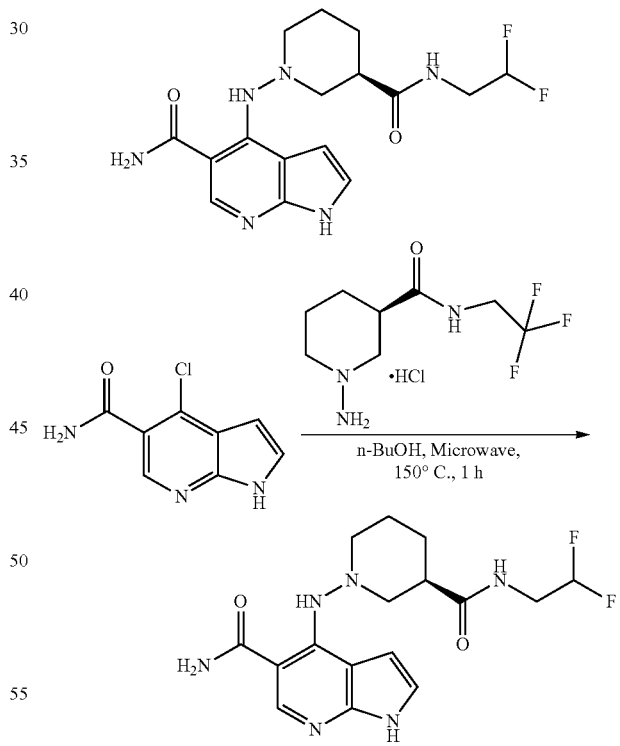

(R)-1-amino-N-(2,2-difluoroethyl)piperidine-3-carboxamide hydrochloride was synthesized with reference to the preparation method of (S)-1-amino-N-(2,2-difluoroethyl)piperidine-3-carb oxamide in Example 2, by replacing (S)-1-(tert-butoxycarbonyl)piperidine-3-carboxylic acid in Step 1 of Example 2 with (R)-1-(tert-butoxycarbonyl)piperidine-3-carboxylic acid.

4-chloro-7-azaindole-5-carboxamide (0.10 g, 0.51 mmol) and (R)-1-amino-N-(2,2-difluoro ethyl)piperidine-3-carboxamide hydrochloride (0.25 g, 1.02 mmol) were added into a microwave tube, 2 mL of n-butyl alcohol was added, and the microwave reaction continued for 1 h at 150° C. The reaction was filtered, and the filtrate was rotary evaporated to dryness, and subjected to column chromatography (dichloromethane/methanol system) to obtain 0.035 g of a light-yellow solid powder, with a yield of 18.7%. $^1$H NMR (400 MHz, DMSO-$d_6$) δ 11.42 (br, 1H), 9.94 (br, 1H), 8.38 (s, 1H), 8.32 (br, 1H), 7.82 (br, 1H), 7.08 (m, 3H), 5.97 (t, J=57.5 Hz, 1H), 3.46 (br, 2H), 3.12 (m, 2H), 2.68 (m, 1H), 2.37 (m, 2H), 1.80 (m, 2H), 1.67 (m, 1H), 1.34 (m, 1H). MS (ESI) m/z: 367 [M+H]$^+$.

Example 5

Synthesis of (S)-4-(3-(n-propylcarbamoyl)piperidine-1-amino)-1H-7-azaindole-5-carboxamide

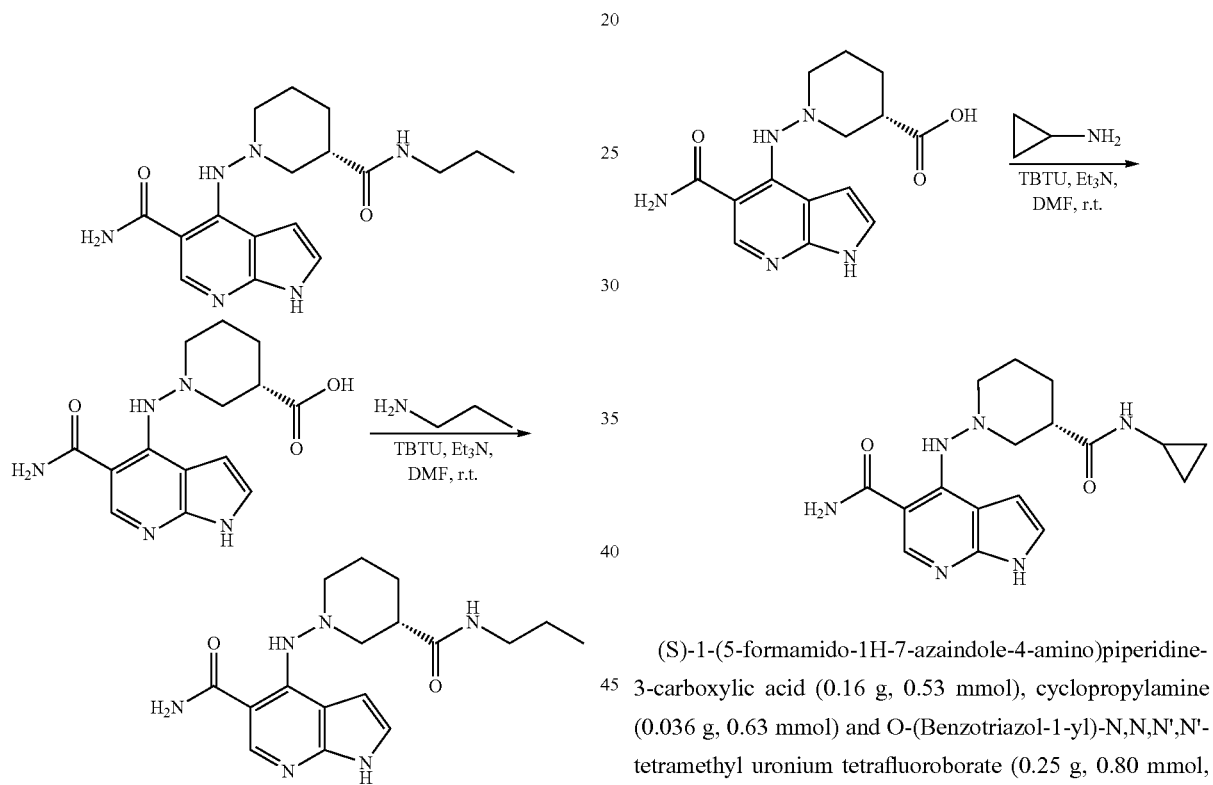

(S)-1-(5-formamido-1H-7-azaindole-4-amino)piperidine-3-carboxylic acid (0.25 g, 0.82 mmol), n-propylamine (0.058 g, 1.00 mmol) and O-(Benzotriazol-1-yl)-N,N,N',N'-tetramethyluronium tetrafluoroborate (0.39 g, 1.23 mmol, TBTU) were added into a one-neck flask, 5 mL of DMF was added, and triethylamine (0.25 g, 2.46 mmol) was added after stirring up. After the addition was complete, the reaction continued with stirring for 16 h at room temperature. The reaction was directly evaporated to dryness under reduced pressure and subjected to column chromatography (dichloromethane/methanol system) to obtain 48 mg of a light-yellow solid, with a yield of 17%. $^1$H NMR (300 MHz, DMSO-$d_6$) δ 11.44 (br, 1H), 9.97 (br, 1H), 8.38 (s, 1H), 7.85 (br, 2H), 7.05 (m, 3H), 3.11 (m, 2H), 2.98 (m, 2H), 2.60 (m, 1H), 2.30 (m, 2H), 1.72 (m, 3H), 1.38 (m, 3H), 0.81 (t, J=7.4 Hz, 3H). MS (ESI) m/z: 345 [M+H]$^+$.

Example 6

Synthesis of (S)-4-(3-(cyclopropylcarbamoyl)piperidine-1-amino)-1H-7-azaindole-5-carboxamide

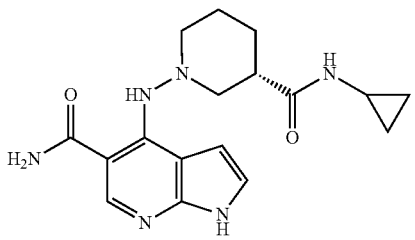

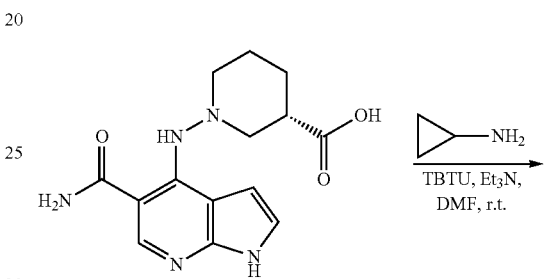

(S)-1-(5-formamido-1H-7-azaindole-4-amino)piperidine-3-carboxylic acid (0.16 g, 0.53 mmol), cyclopropylamine (0.036 g, 0.63 mmol) and O-(Benzotriazol-1-yl)-N,N,N',N'-tetramethyl uronium tetrafluoroborate (0.25 g, 0.80 mmol, TBTU) were added into a one-neck flask, 5 mL of DMF was added, and triethylamine (0.16 g, 1.59 mmol) was added after stirring up. After the addition was complete, the reaction continued with stirring for 16 h at room temperature. The reaction was directly evaporated to dryness under reduced pressure and subjected to column chromatography (dichloromethane/methanol system) to obtain 45 mg of a light-yellow solid, with a yield of 25%. $^1$H NMR (300 MHz, DMSO-$d_6$) δ 11.52 (br, 1H), 10.03 (br, 1H), 8.39 (s, 1H), 7.93 (br, 2H), 7.09 (m, 2H), 7.01 (m, 1H), 3.09 (m, 2H), 2.59 (m, 2H), 2.33 (m, 2H), 1.80 (m, 2H), 1.65 (m, 1H), 1.36 (m, 1H), 0.56 (dt, J=4.6, 2.7 Hz, 2H), 0.36 (dt, J=4.6, 2.7 Hz, 2H). MS (ESI) m/z: 343 [M+H]$^+$.

Example 7

Synthesis of (S)-4-(3-(cyanoethylcarbamoyl)piperidine-1-amino)-1H-7-azaindole-5-carboxamide

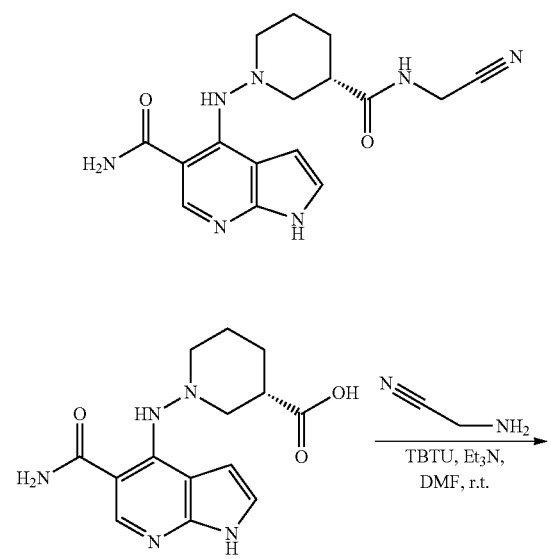

(S)-1-(5-formamido-1H-7-azaindole-4-amino)piperidine-3-carboxylic acid (0.25 g, 0.82 mmol), aminoacetonitrile hydrochloride (0.093 g, 1.00 mmol) and O-(Benzotriazol-1-yl)-N,N,N',N'-tetramethyluronium tetrafluoroborate (0.39 g, 1.23 mmol, TBTU) were added into a one-neck flask, 5 mL of DMF was added, and triethylamine (0.25 g, 2.46 mmol) was added after stirring up. After the addition was complete, the reaction continued with stirring for 16 h at room temperature. The reaction was directly evaporated to dryness under reduced pressure and subjected to column chromatography (dichloromethane/methanol system) to obtain 43 mg of a light-yellow solid, with a yield of 15%. $^1$H NMR (300 MHz, DMSO-d$_6$) δ 11.50 (br, 1H), 10.01 (br, 1H), 8.67 (br, 1H), 8.38 (s, 1H), 7.84 (br, 1H), 7.05 (m, 3H), 4.11 (br, 2H), 3.18 (m, 2H), 2.66 (m, 1H), 2.38 (m, 2H), 1.77 (m, 3H), 1.30 (m, 1H). MS (ESI) m/z: 342 [M+H]$^+$.

Example 8

Ethyl (S)-1-(5-formamido-1H-7-azaindole-4-amino)piperidine-3-carboxylate

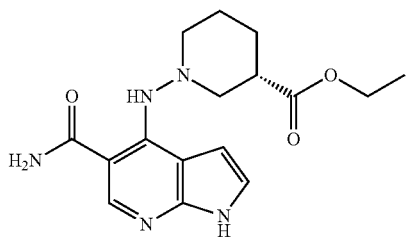 [SMILES: CCOC(=O)[C@H]1CCCN(Nc2c(C(N)=O)cnc3[nH]ccc23)C1]

Ethyl (S)-1-(5-formamido-1H-7-azaindole-4-amino)piperidine-3-carboxylate is an intermediate obtained in Step 7 of Example 1. $^1$H NMR (300 MHz, DMSO-d$_6$) δ 11.40 (br, 1H), 9.97 (br, 1H), 8.38 (s, 1H), 8.19 (br, 1H), 7.79 (br, 1H), 7.07 (br, 1H), 6.98 (br, 1H), 4.06 (q, J=7.0 Hz, 2H), 3.18 (m, 2H), 2.78 (m, 1H), 2.38 (m, 2H), 1.79 (m, 3H), 1.30 (m, 1H), 1.15 (t, J=4.0 Hz, 3H). MS (ESI) m/z: 332 [M+H]$^+$.

Example 9

Synthesis of 4-(3-(2,2,2-trifluoroethylcarbamoyl)pyrrole-1-amino)-1H-7-azaindole-5-carboxamide

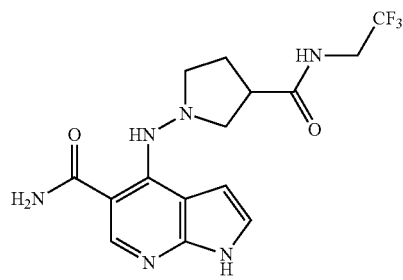 [SMILES: NC(=O)c1cnc2[nH]ccc2c1NN1CCC(C(=O)NCC(F)(F)F)C1]

Step 1: Synthesis of 1-tert-butoxycarbonyl-pyrrole-3-carboxylic acid

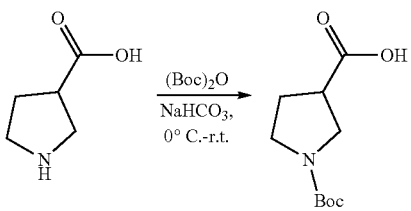 [SMILES: "(Boc)2O" ; O=C(O)C1CCNC1 ; CC(C)(C)OC(=O)N1CCC(C(=O)O)C1]

3-pyrrolecarboxylic acid (1.00 g, 8.68 mmol) was dissolved in a mixed solvent of 10 mL of THF and 5 mL of water at room temperature. Sodium bicarbonate (2.18 g, 0.026 mol) was added and cooled to 0° C. and (Boc)$_2$O (2.08 g, 9.55 mmoL) was dropwise added. The addition was complete, the reaction continued at room temperature for 2 h. 100 mL of EA was added into the reaction for extraction and impurity removal. The aqueous phase was adjusted with a solution of citric acid to pH=4, extracted by adding DCM, dried with anhydrous sodium sulfate, and concentrated to obtain 1.64 g of a white solid, with a yield of 88%.

Step 2: Synthesis of 1-tert-butoxycarbonyl-pyrrole-3-(2,2,2-trifluoroethyl) carboxamide

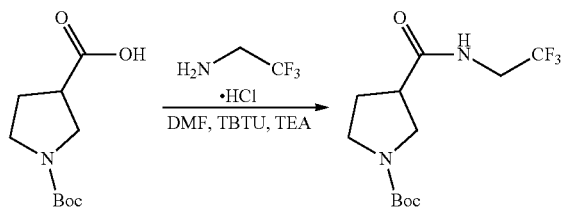 [SMILES: CC(C)(C)OC(=O)N1CCC(C(=O)O)C1 ; NCC(F)(F)F ; Cl ; CC(C)(C)OC(=O)N1CCC(C(=O)NCC(F)(F)F)C1]

1-tert-butoxycarbonyl-pyrrole-3-carboxylic acid (1.64 g, 7.62 mmoL) was added into 20 mL of DMF at room temperature. 0-(Benzotriazol-1-yl)-N,N,N',N'-tetramethyluronium tetrafluoroborate (3.67 g, 11.43 mmoL, TBTU), 2,2,2-Trifluoroethanamine hydrochloride (1.24 g, 9.15 mmoL) and triethylamine (2.31 g, 0.023 moL) were sequentially added, and the reaction continued with stirring for 16 h at room temperature. The reaction was poured into 50 mL of water, and extracted by adding 30 mL of DCM. The aqueous phase was further extracted twice with DCM. The organic phases were combined, washed with saturated brine, dried with anhydrous sodium sulfate, evaporated under reduced pressure to dryness, and subjected to column chromatography on silica gel (PE:EA=1:1) to obtain 1.90 g of a light-yellow oily substance, with a yield of 84%.

Step 3: Synthesis of N-(2,2,2-trifluoroethyl)pyrrole-3-carboxamide hydrochloride

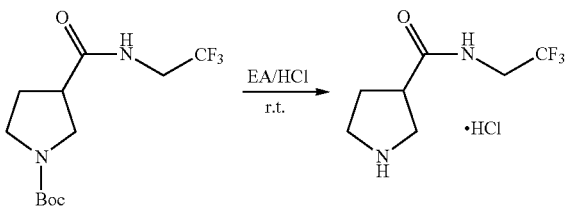 [SMILES: CC(C)(C)OC(=O)N1CCC(C(=O)NCC(F)(F)F)C1 ; O=C(NCC(F)(F)F)C1CCNC1 ; Cl]

1-tert-butoxycarbonyl-pyrrole-3-(2,2,2-trifluoroethyl) carboxamide (1.90 g, 6.42 mmoL) was dissolved in a solution of hydrochloric acid in ethyl acetate (20 mL), and the reaction continued with stirring for 16 h at room temperature. The reaction was directly evaporated under reduced pressure to remove the solvent, to obtain 1.45 g of a viscous and thick oily substance, with a crude product yield of 100%.

Step 4: Synthesis of 1-nitroso-N-(2,2,2-trifluoroethyl)pyrrole-3-carboxamide

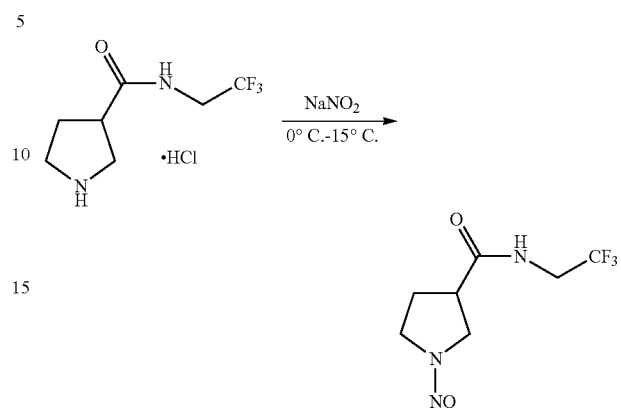

N-(2,2,2-trifluoroethyl)piperidine-3-carboxamide hydrochloride (1.45 g, 6.23 mmoL) was added into a mixed solvent of 20 mL of glacial acetic acid and 5 mL of water and cooled to 0° C., and 5 mL of an aqueous solution prepared from sodium nitrite (0.65 g, 9.35 mmoL) was dropwise added. The reaction continued with stirring for 1 h at 0° C. and then for 2 h at room temperature. The reaction was added with water, extracted three times with ethyl acetate. The organic phases were combined, washed with saturated brine, and evaporated under reduced pressure to dryness, to obtain 1.25 g of a light-yellow liquid which was directly applied to the next-step reaction, with a crude product yield of 95%.

Step 5: Synthesis of 1-amino-N-(2,2,2-trifluoroethyl)pyrrole-3-carboxamide hydrochloride

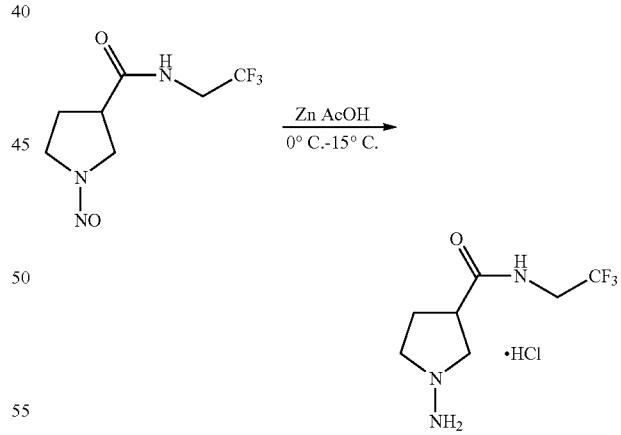

1-nitroso-N-(2,2,2-trifluoroethyl)pyrrole-3-carboxamide (1.25 g, 5.90 mmoL) was dissolved in 20 mL of methanol, Zn (1.15 g, 0.018 moL) was added and cooled to −5° C., and glacial acetic acid (10 mL) was slowly and dropwise added. After the addition was complete, stirring was carried out for 0.5 h at 0° C. It was naturally wormed to room temperature, and reacted for 2 h. The reaction was filtered, the filter cake was rinsed with methanol, and the filtrate was evaporated to dryness under reduced pressure. 50 mL of water was added into the residue, and the solution was adjusted with sodium carbonate to pH 9, and extracted five times with a mixed solvent of DCM/MeOH (5:1). The organic phases were combined, washed once with saturated brine, and then dried with anhydrous sodium sulfate, filtered, and concentrated to obtain a light-yellow liquid. A solution of hydrochloric acid in ethyl acetate was added and stirred for 1 h for salt formation, and the solvent was rotary evaporated to dryness, to obtain 1.50 g of a light-yellow oily substance, with a yield of 100%.

Step 6: Synthesis of 4-(3-(2,2,2-trifluoroethylcarbamoyl)pyrrole-1-amino)-1H-7-azaindole-5-carboxamide 4-(3-(2,2,2-trifluoroethylcarbamoyl)pyrrole-1-amino)-1H-7-azaindole-5-carboxamide was prepared with reference to the method in Step 5 of Example 2, by replacing (S)-1-amino-N-(2,2-difluoroethyl)piperidine-3-carboxamide hydrochloride with 1-amino-N-(2,2,2-trifluoroethyl) piperidine-3-carboxamide hydrochloride. $^1$H NMR (300 MHz, DMSO-$d_6$) δ 11.40 (br, 1H), 9.97 (br, 1H), 8.62 (br, 1H), 8.36 (s, 1H), 7.77 (br, 1H), 7.04 (m, 3H), 3.95 (m, 2H), 3.23-3.02 (m, 3H), 2.69 (m, 2H), 2.07 (m, 2H). MS (ESI) m/z: 371 [M+H]$^+$.

Example 10

Synthesis of 4-((3-oxa-8-azabicyclo[3.2.1]octan-8-yl)amino)-1H-7-azaindole-5-carboxamide

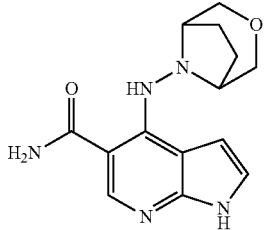 [SMILES: NC(=O)c1cnc2[nH]ccc2c1NN1C2CCC1COC2]

Step 1: Synthesis of 8-nitroso-3-oxa-8-azabicyclo[3.2.1]octane

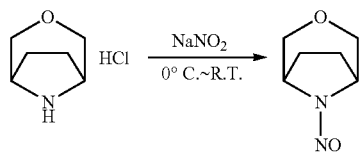

3-oxa-8-azabicyclo[3.2.1]octane hydrochloride (0.30 g, 2.00 mmol) was dissolved in 6 mL of acetic acid at room temperature, and 3 mL of an aqueous solution with dissolved sodium nitrite (0.21 g, 0.30 mmol) was slowly added at 0° C. After dropwise addition was complete, the reaction continued for 1 hour at 0° C. and then continued overnight at normal temperature. After the reaction was complete, the reaction was added with 15 mL of water, and extracted three times with 15 mL of ethyl acetate. The organic phases were combined, washed with a saturated aqueous solution of sodium carbonate, dried with anhydrous sodium sulfate, concentrated, and subjected to column chromatography on silica gel (PE/EA) to obtain 0.24 g of a yellow solid, with a yield of 85%. MS (ESI) m/z: 143 [M+H]$^+$.

Step 2: Synthesis of 3-oxa-8-azabicyclo[3.2.1]octan-8-amine

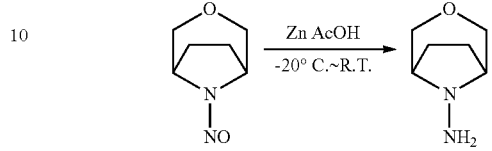

8-nitroso-3-oxa-8-azabicyclo[3.2.1]octane (0.24 g, 1.69 mmol) was dissolved in 4 mL of methanol, and zinc powder (0.33 g, 5.06 mmol) was slowly added at room temperature, and cooled to −20° C. and stirred for 10 minutes under nitrogen protection. 4 mL of acetic acid was slowly and dropwise added at −20° C., and the reaction continued with stirring for 2 h. The reaction was filtered, and the filtrate was directly evaporated to dryness, and subjected to column chromatography on silica gel (DCM/MeOH) to obtain 0.20 g of a white solid-oil mixture, with a yield of 93%. MS (ESI) m/z: 129 M+H*.

Step 3: Synthesis of 4-((3-oxa-8-azabicyclo[3.2.1]octan-8-yl)amino)-1H-7-azaindole-5-carb oxamide 4-((3-oxa-8-azabicyclo[3.2.1]octan-8-yl)amino)-1H-7-azaindole-5-carboxamide was prepared with reference to the method in Step 5 of Example 2, by replacing (S)-1-amino-N-(2,2-difluoroethyl)piperidine-3-carboxamide hydrochloride with 3-oxa-8-azabicyclo[3.2.1]octan-8-amine.

$^1$H NMR (300 MHz, DMSO-$d_6$) δ 11.41 (br, 1H), 10.44 (br, 1H), 8.38 (s, 1H), 8.33 (br, 1H), 7.23 (br, 1H), 7.06 (m, 2H), 3.77 (d, J=10.7 Hz, 2H), 3.57 (d, J=10.6 Hz, 2H), 3.27 (m, 2H), 1.94 (q, J=10.5, 9.2 Hz, 4H). MS (ESI) m/z: 288 [M+H]$^+$.

Example 11

Synthesis of 4-((3-hydroxyl-8-azabicyclo[3.2.1]octan-8-yl)amino)-1H-7-azaindole-5-carboxamide

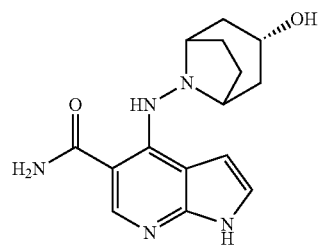

Step 1: Synthesis of (1R,3R,5S)-8-nitroso-8-azabicyclo[3.2.1]octan-3-ol

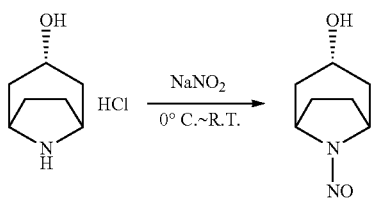

(1R,3R,5S)-8-azabicyclo[3.2.1]octan-3-ol hydrochloride (0.50 g, 3.94 mmol) was dissolved in acetic acid (10 mL) at room temperature, 5 mL of an aqueous solution with dissolved sodium nitrite (0.54 g, 7.88 mmol) was slowly added at 0° C. After dropwise addition was complete, the reaction continued for 1 hour at 0° C. and then continued overnight at nor mal temperature. After the reaction was complete, the reaction was added with water (15 m L), and extracted three times with ethyl acetate (15 mL). The organic phases were combined, washed with a saturated aqueous solution (20 mL) of sodium carbonate, dried with anhydrous sodium sulfate, concentrated, and subjected to column chromatography on silica gel (PE/EA) to obtain 0.59 g of a yellow solid, with a yield of 96%. MS (ESI) m/z: 157.1 [M+H]$^+$.

Step 2: Synthesis of (1R,3R,5S)-8-amino-8-azabicyclo[3.2.1]octan-3-ol

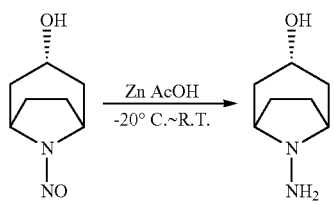

(1R,3R,5S)-8-nitroso-8-azabicyclo[3.2.1]octan-3-ol (0.51 g, 3.27 mmol) was dissolved in methanol (6 mL), and zinc powder (0.64 g, 9.81 mmol) was slowly added at room temperature, and cooled to −20° C. and stirred for 10 minutes under nitrogen protection. Acetic acid (8 mL) was slowly and dropwise added at −20° C. and the reaction continued for 2 hours at 0° C. under nitrogen protection and was terminated. The reaction was filtered, and the filtrate was adjusted with sodium carbonate to pH 8, concentrated, and subjected to column chromatography on silica gel (DCM/MeOH) to obtain 0.57 g of a white solid-oil mixture, with a yield of greater than 100%. MS (ESI) m/z: 143.1 [M+H]$^+$.

Step 3: Synthesis of ((3-hydroxyl-8-azabicyclo[3.2.1]octan-8-yl)amino)-1H-7-azaindole-5-carboxamide ((3-hydroxyl-8-azabicyclo[3.2.1]octan-8-yl)amino)-1H-7-azaindole-5-carboxamide was prepared with reference to the method in Step 5 of Example 2, by replacing (S)-1-amino-N-(2,2-difluoroethyl)piperidine-3-carboxamide hydrochloride with (1R,3r,5S)-8-amino-8-azabicyclo[3.2.1]octan-3-ol.

$^1$H NMR (400 MHz, Methanol-d$_4$) δ 8.31 (s, 1H), 7.71 (br, 1H), 7.34 (d, J=3.5 Hz, 1H), 7.08 (br, 2H), 3.40 (t, J=3.6 Hz, 1H), 2.37-2.31 (m, 2H), 2.25-2.10 (m, 3H), 2.05 (dd, J=12.3, 6.4 Hz, 1H), 1.94 (d, J=3.5 Hz, 1H), 1.91 (m, 1H), 1.61 (t, J=13.1 Hz, 2H). MS (ESI) m/z: 302 [M+H]$^+$.

Example 12

Synthesis of 4-(N-Boc-5-amino-hexahydropyrrolo[3,4-c]pyrrole-2(1H))-1H-7-azaindole-5-carboxamide

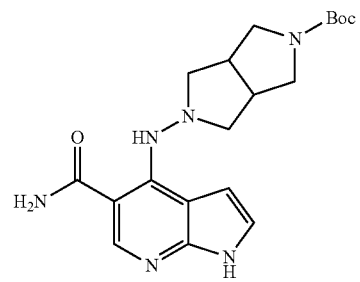 [SMILES: CC(C)(C)OC(=O)N1CC2CN(Nc3c(C(N)=O)cnc4[nH]ccc34)CC2C1]

Step 1: Synthesis of N-Boc-5-nitroso-hexahydropyrrolo[3,4-c]pyrrole-2(1H)

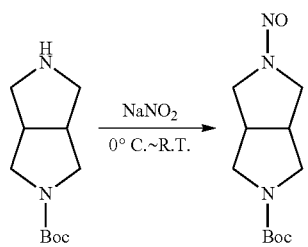

N-Boc-hexahydropyrrolo[3,4-c]pyrrole-2(1H) (2.12 g, 10 mmoL) was added into a mixed solvent of 20 mL of glacial acetic acid and 5 ml of water, and cooled to 0° C., and 5 ml of an aqueous solution with dissolved sodium nitrite (1.03 g, 15 mmoL) was dropwise added. The stirring was carried out for 1 h at 0° C., and then the reaction was naturally w armed to room temperature, and reacted for 2 h. The reaction was added with water, and extracted three times with ethyl acetate. The organic layers were combined, and washed with saturated brine to obtain 2.41 g of a white solid, which is evaporated under reduced pressure to dryness and directly applied to the next step.

Step 2: Synthesis of N-Boc-5-amino-hexahydropyrrolo[3,4-c]pyrrole-2(1H)

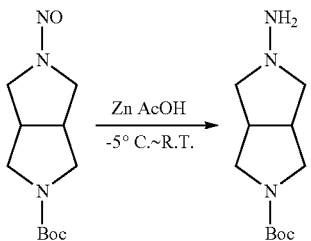

N-Boc-5-nitroso-hexahydropyrrolo[3,4-c]pyrrole-2(1H) (2.41 g, 10 mmoL) was dissolved in 20 mL of methanol, Zn (1.95 g, 0.03 moL) was added and cooled to −5° C. and 10 mL of glacial acetic acid was slowly and dropwise added. After the addition was complete, stirring was carried out for 0.5 h at 0° C., and the reaction was naturally warmed to room temperature and reacted for 2 h. The reaction was filtered, the filter cake was rinsed with methanol, and the filtrate was evaporated to dryness under reduced pressure. 50 mL of water was added for dissolution. Then, the solution was adjusted with sodium carbonate to pH 9, and extracted five times with a mixed solvent of DCM/MeOH (5:1). The organic phases were combined, washed with saturated brine, dried with anhydrous sodium sulfate, and evaporated to remove the solvent, to obtain 1.76 g of a white solid, with a yield of 81.8%.

Step 3: Synthesis of 4-(N-Boc-5-amino-hexahydro-pyrrolo[3,4-c]pyrrole-2(1H))-1H-7-azaindole-5-carboxamide 4-(N-Boc-5-amino-hexahydropyrrolo[3,4-c]pyrrole-2(1H))-1H-7-azaindole-5-carboxamide was prepared with reference to the method in Step 5 of Example 2, by replacing (S)-1-amino-N-(2,2-difluoroethyl)piperidine-3-carboxamide hydrochloride with N-Boc-5-amino-hexahydropyrrolo[3,4-c]pyrrole-2(1H).

$^1$H NMR (400 MHz, DMSO-d$_6$) δ 11.38 (br, 1H), 9.86 (br, 1H), 8.36 (s, 1H), 7.78 (br, 1H), 7.15-6.58 (m, 3H), 3.57 (m, 2H), 3.09 (m, 2H), 2.88-2.51 (m, 4H), 1.45 (s, 9H), 1.18 (m, 1H), 0.77 (m, 1H). MS (ESI) m/z: 387 [M+H]$^+$.

Example 13

Synthesis of 4-(5-acetylhexahydropyrrolo[3,4-c]pyrrole-2(1H))-1H-7-azaindole-5-carboxamide

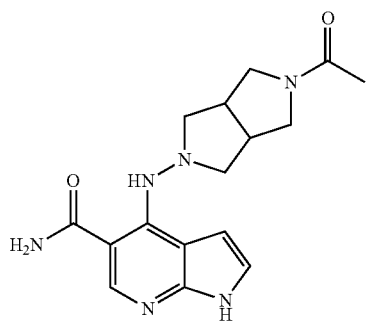 [SMILES: CC(=O)N1CC2CN(Nc3c(C(N)=O)cnc4[nH]ccc34)CC2C1]

Step 1: Synthesis of 1-(5-nitrosohexahydropyrrolo[3,4-c]pyrrol-2(1H)-yl)ethan-1-one

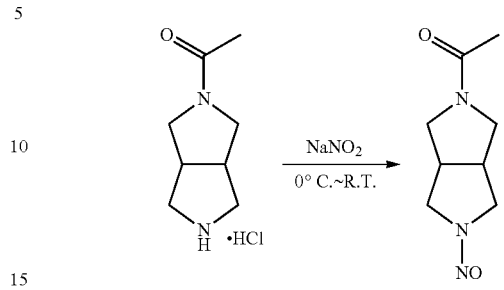

1-(hexahydropyrrolo[3,4-c]pyrrol-2(1H)-yl)ethan-1-one hydrochloride (1.50 g, 7.87 mmoL) was added into a mixed solvent of 20 mL of glacial acetic acid and 5 ml of water, and cooled to 0° C., and 5 ml of an aqueous solution with dissolved sodium nitrite (0.81 g, 11.80 mmoL) was dropwise added. The stirring was carried out for 1 h at 0° C. and the reaction was naturally warmed to room temperature and reacted for 2 h. The reaction was added with water, and extracted three times with ethyl acetate. The organic phases were combined, washed with saturated brine and evaporated under reduced pressure to remove the solvent, to obtain 1.44 g of a light-yellow liquid which was directly applied to the next step, with a yield of 100%.

Step 2: Synthesis of 1-(5-aminohexahydropyrrolo[3,4-c]pyrrol-2(1H)-yl)ethan-1-one hydrochloride

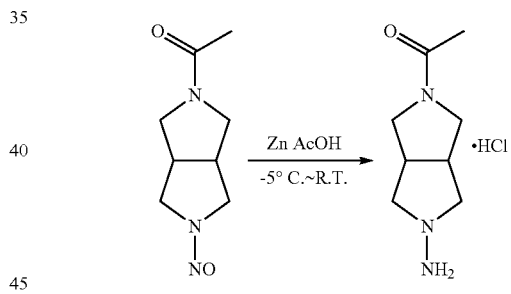

1-(5-nitrosohexahydropyrrolo[3,4-c]pyrrol-2(1H)-yl)ethan-1-one (1.44 g, 7.87 mmoL) was dissolved in 20 mL of methanol, Zn powder (1.53 g, 0.023 moL) was added and cooled to −5° C., and glacial acetic acid (10 mL) was slowly and dropwise added. After the addition was complete, the stirring was carried out for 0.5 h at 0° C., and the reaction was naturally warmed to room temperature, and reacted for 2 h. The reaction was filtered, the filter cake was rinsed with methanol and the filtrate was evaporated to dryness under reduced pressure. The residue was dissolved by adding 50 mL of water, and the solution was adjusted with sodium carbonate to pH 9, and extracted five times with a mixed solvent of DCM/MeOH (5:1). The organic phases were combined, washed with saturated brine, dried with anhydrous sodium sulfate and evaporated under reduced pressure to remove the solvent, to obtain a light-yellow liquid, to which a solution of hydrochloric acid in ethyl acetate was added, and stirred for 0.5 h for salt formation. Evaporation was performed to remove the solvent, to obtain 2.00 g of a light-yellow oily substance, with a crude product yield of 100%.

Step 3: Synthesis of 4-(5-acetylhexahydropyrrolo[3,4-c]pyrrole-2(1H))-1H-7-azaindole-5-carboxamide 4-(5-acetylhexahydropyrrolo[3,4-c]pyrrole-2(1H))-1H-7-azaindole-5-carboxamide was prepared with reference to the method in Step 5 of Example 2, by replacing (S)-1-amino-N-(2,2-difluoroethyl)piperidine-3-carboxamide hydrochloride with 1-(5-aminohexahydropyrrolo[3,4-c]pyrrol-2(1H)-yl)ethan-1-one hydrochloride.

$^1$H NMR (400 MHz, DMSO-d$_6$) δ 11.40 (br, 1H), 9.85 (br, 1H), 8.36 (s, 1H), 7.88 (br, 1H), 7.12 (br, 1H), 7.03 (br, 1H), 6.85 (br, 1H), 3.67 (m, 2H), 3.14-2.62 (m, 6H), 2.00 (s, 3H), 1.28 (m, 1H), 0.86 (m, 1H). MS (ESI) m/z: 329 [M+H]$^+$.

Example 14

Synthesis of 4-(1-keto-2,8-diazaspiro[4.5]decane-8-amino)-1H-7-azaindole-5-carboxamide

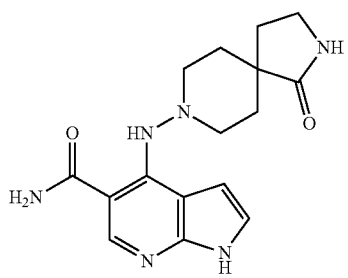 [SMILES: NC(=O)c1cnc2[nH]ccc2c1NN1CCC2(CCNC2=O)CC1]

Step 1: Synthesis of 8-nitroso-2,8-diazaspiro[4.5]decan-1-one

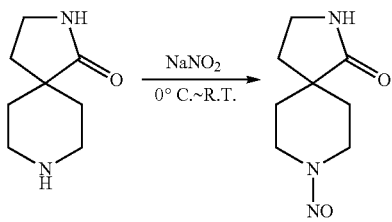

2,8-diazaspiro[4.5]decan-1-one (2.08 g, 20 mmoL) was added into a mixed solvent of 20 mL of glacial acetic acid and 5 ml of water and cooled to 0° C., and 10 ml of an aqueous solution with dissolved sodium nitrite (2.07 g, 30 mmoL) was dropwise added. The stir ring was carried out for 1 h at 0° C., and the reaction was naturally warmed to room temperature, and reacted for 2 h. The reaction was added with water, and extracted three times with ethyl acetate. The organic phases were combined, washed with saturated brine, and evaporated under reduced pressure to dryness, to obtain 2.47 g of a crude product, which was directly applied to the next-step reaction.

Step 2: Synthesis of 8-amino-2,8-diazaspiro[4.5]decan-1-one hydrochloride

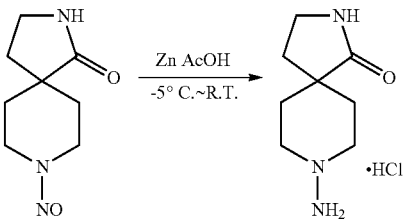

8-nitroso-2,8-diazaspiro[4.5]decan-1-one (2.47 g, 20 mmoL) dissolved in 20 mL of methanol, Zn (3.90 g, 0.06 moL) was added and cooled to −5° C., and 10 mL of glacial acetic acid was slowly and dropwise added. The addition was complete, stirring was carried out for 0.5 h at 0° C. and the reaction was naturally warmed to room temperature and reacted for 2 h. The reaction was filtered, the filter cake was rinsed with methanol, and the filtrate was evaporated to dryness under reduced pressure. A solution of hydrochloric acid in ethanol was added and stirred for 0.5 h, and the solvent was evaporated off under reduced pressure. Then, a slurry was formed with ethyl acetate, and filtered, and the filter cake was dried to obtain 2.12 g of a light-yellow solid, with a yield of 93%.

Step 3: Synthesis of 4-(1-keto-2,8-diazaspiro[4.5]decane-8-amino)-1H-7-azaindole-5-carboxamide 4-(1-keto-2,8-diazaspiro[4.5]decane-8-amino)-1H-7-azaindole-5-carboxamide was prepared with reference to the method in Step 5 of Example 2, by replacing (S)-1-amino-N-(2,2-difluoroethyl)piperidine-3-carboxamide hydrochloride with 8-amino-2,8-diazaspiro[4.5]decan-1-one hydrochloride.

$^1$H NMR (400 MHz, DMSO-d) S 11.39 (br, 1H), 9.92 (br, 1H), 8.37 (s, 1H), 7.64 (br, 2H), 7.05 (m, 3H), 3.53 (m, 2H), 3.19 (m, 2H), 3.05 (m, 2H), 1.97 (m, 2H), 1.91 (m, 2H), 1.49 (m, 2H). MS (ESI) m/z: 329 [M+H]$^+$.

Example 15

Synthesis of 4-(8-(cyclopropylcarbonyl)-3,8-diazabicyclo[3.2.1]octane-3-amino)-1H-7-azaindole-5-carboxamide

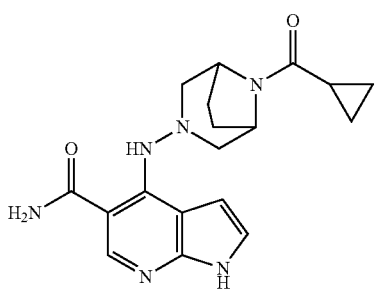 [SMILES: NC(=O)c1cnc2[nH]ccc2c1NN1CC2CCC(C1)N2C(=O)C1CC1]

Step 1: Synthesis of 8-cyclopropylcarbonyl-3-nitroso-3,8-diazabicyclo[3.2.1]octane

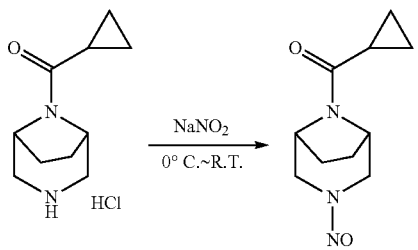

8-cyclopropylcarbonyl-3,8-diazabicyclo[3.2.1]octane hydrochloride (1.11 g, 5.00 mmoL) was added into a mixed solvent of 20 mL of glacial acetic acid and 5 ml of water and cooled to 0° C., and 5 ml of an aqueous solution with dissolved sodium nitrite (0.53 g, 7.68 mmoL) was dropwise added. The stirring was carried out for 1 h at 0° C., and the reaction was naturally warmed to room temperature, and reacted for 2 h. The reaction was added with water, and extracted three times with ethyl acetate. The organic phases were combined, washed with saturated brine and evaporated under reduced pressure to remove the solvent, to obtain 1.04 g of a light-yellow liquid, which was directly applied to the next-step reaction.

Step 2: Synthesis of 8-cyclopropylcarbonyl-3-amino-3,8-diazabicyclo[3.2.1]octane

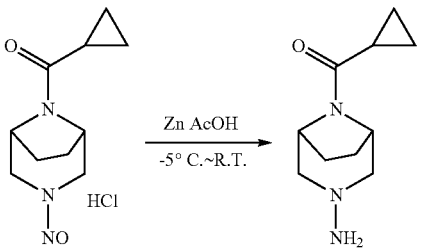

8-cyclopropylcarbonyl-3-nitroso-3,8-diazabicyclo[3.2.1]octane (1.04 g, 5.00 mmoL) was dissolved in 20 mL of methanol at room temperature, zinc powder (1.00 g, 15.00 mmoL) was added and cooled to −5° C., and 10 mL of glacial acetic acid was slowly and dropwise added. After the addition was complete, the stirring was carried out for 0.5 h at 0° C., and the reaction was naturally warmed to room temperature, and reacted for 2 h. The reaction was filtered, the filter cake was rinsed with methanol, and the filtrate was collected, and evaporated under reduced pressure to dryness. 50 mL of water was added for dissolution. The solution was adjusted to pH 9 with an aqueous solution of sodium carbonate, and extracted five times with a mixed solvent of DCM/MeOH (5:1). The organic phases were combined, washed with saturated brine, dried with anhydrous sodium sulfate, and evaporated under reduced pressure to remove the solvent, to obtain 0.98 g of a light-yellow oily substance.

Step 3: Synthesis of 4-(8-(cyclopropylcarbonyl)-3,8-diazabicyclo[3.2.1]octane-3-amino)-1H-7-azaindole-5-carboxamide 4-(8-(cyclopropylcarbonyl)-3,8-diazabicyclo[3.2.1]octane-3-amino)-1H-7-azaindole-5-carboxamide was prepared with reference to the method in Step 5 of Example 2, by replacing (S)-1-amino-N-(2,2-difluoroethyl)piperidine-3-carboxamide hydrochloride with 8-cyclopropylcarbonyl-3-amino-3,8-diazabicyclo[3.2.1]octane.

$^1$H NMR (400 MHz, DMSO-d$_6$) δ 11.44 (br, 1H), 10.47 (br, 1H), 8.40 (s, 1H), 7.83 (br, 1H), 7.23 (br, 1H), 7.10 (m, 2H), 4.20 (d, J=12.6 Hz, 1H), 4.10 (d, J=13.9 Hz, 1H), 3.54 (d, J=13.3 Hz, 1H), 3.43 (m, 2H), 2.98 (d, J=13.7 Hz, 1H), 1.96 (m, 3H), 1.72 (m, 1H), 1.58 (m, 1H), 0.76 (m, 4H). MS (ESI) m/z: 355 [M+H]$^+$.

Example 16

Synthesis of 4-(2-methyl-5-(2,2,2-trifluoroethylcarbamoyl)piperidine-1-amino)-1H-7-azaindole-5-carboxamide

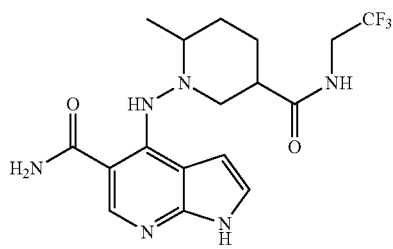 [SMILES: CC1CCC(C(=O)NCC(F)(F)F)CN1Nc1c(C(N)=O)cnc2[nH]ccc12]

Step 1: Synthesis of 6-methyl-1-nitroso-N-(2,2,2-trifluoroethyl)piperidine-3-carboxamide

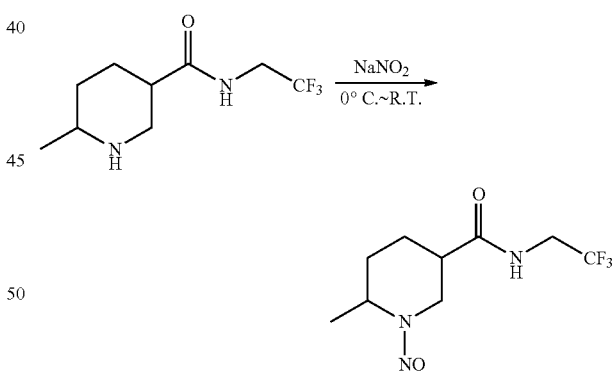

6-methyl-N-(2,2,2-trifluoroethyl)piperidine-3-carboxamide (2.24 g, 10.00 mmoL) was added into a mixed solvent of 20 mL of glacial acetic acid and 10 ml of water and cooled to 0° C. and 10 ml of an aqueous solution with dissolved sodium nitrite (1.03 g, 15.00 mmoL) was dropwise added. The stirring was carried out for 1 h at 0° C., and the reaction was naturally warmed to room temperature, and reacted for 1 h. The reaction was added with water, and extracted three times with DCM. The organic phases were combined, washed with saturated brine, and evaporated to dryness under reduced pressure, to obtain 2.53 g of a light-yellow solid, which was directly applied to the next-step reaction.

Step 2: Synthesis of 6-methyl-1-amino-N-(2,2,2-trifluoroethyl)piperidine-3-carboxamide

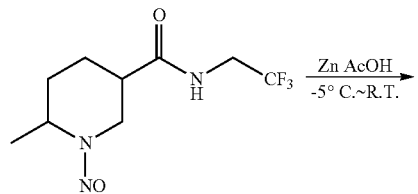

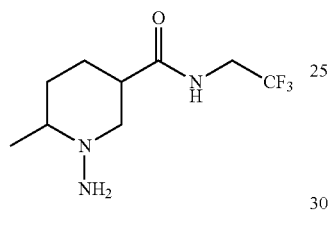

6-methyl-1-nitroso-N-(2,2,2-trifluoroethyl)piperidine-3-carboxamide (2.53 g, 10.00 mmoL) was dissolved in 20 mL of methanol at room temperature, zinc powder (2.40 g, 40.00 m moL) was added and cooled to −5° C., and 10 mL of glacial acetic acid was slowly and dropwise added. After the addition was complete, the stirring was carried out for 0.5 h at 0° C., and the reaction was naturally warmed to room temperature, and reacted for 2 h. The reaction was filtered, the filter cake was rinsed with methanol and the filtrate was evaporated to dryness under reduced pressure. 50 mL of water was added for dissolution. The solution was adjusted with sodium carbonate to pH 9, and extracted five times with a mixed solvent of DCM/MeOH (5:1). The organic phases were combined, washed with saturated brine, dried with anhydrous sodium sulfate, and evaporated to dryness under reduced pressure, to obtain 2.11 g of a light-yellow oily substance, with a yield of 88%.

Step 3: Synthesis of 4-(2-methyl-5-(2,2,2-trifluoroethylcarbamoyl)piperidine-1-amino)-1H-7-azaindole-5-carboxamide 4-(2-methyl-5-(2,2,2-trifluoroethylcarbamoyl)piperidine-1-amino)-1H-7-azaindole-5-carboxamide was prepared with reference to the method in Step 5 of Example 2, by replacing (S)-1-amino-N-(2,2-difluoroethyl)piperidine-3-carboxamide hydrochloride with 6-methyl-1-amino-N-(2,2,2-trifluoroethyl)piperidine-3-carboxamide.

$^1$H NMR (400 MHz, Methanol-$d_4$) δ 8.34 (s, 1H), 7.24 (d, J=3.4 Hz, 1H), 7.06 (d, J=3.4 Hz, 1H), 3.89 (m, 2H), 3.28 (m, 1H), 2.83 (m, 1H), 2.66 (m, 1H), 2.52 (m, 1H), 2.29-2.00 (m, 1H), 1.94 (m, 1H), 1.60 (m, 2H), 1.11 (d, J=6.1 Hz, 3H). MS (ESI) m/z: 399 [M+H]$^+$.

Example 17

Synthesis of 4-(8-(2,2,2-trifluoroethylcarbamoyl)-3,8-diazabicyclo[3.2.1]octane-3-amino)-1H-7-azaindole-5-carboxamide

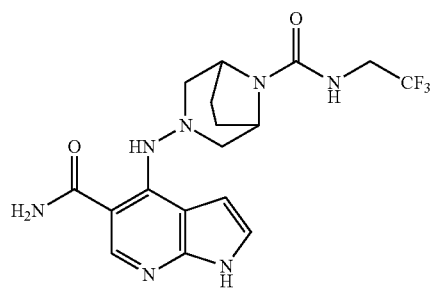 [SMILES: NC(=O)c1cnc2[nH]ccc2c1NN1CC2CCC(C1)N2C(=O)NCC(F)(F)F]

Step 1: Synthesis of 3-nitroso-N-(2,2,2-trifluoroethyl)-3,8-diazabicyclo[3.2.1]octane-8-carboxamide

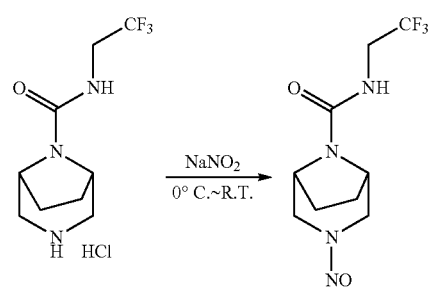

N-(2,2,2-trifluoroethyl)-3,8-diazabicyclo[3.2.1]octane-8-carboxamide hydrochloride (3.51 g, 10.00 mmoL) was added into a mixed solvent of 40 mL of glacial acetic acid and 10 ml of water and cooled to 0° C., and 10 ml of an aqueous solution with dissolved sodium nit rite (1.04 g, 15.00 mmoL) was dropwise added. The stirring was carried out for 1 h at 0° C., and the reaction was naturally warmed to room temperature, and reacted for 1 h. The re action was added with water, and extracted three times with DCM. The organic phases were combined, washed with saturated brine, and evaporated to dryness under reduced pressure, to obtain 2.66 g of a light-yellow solid, which was directly applied to the next-step reaction.

Step 2: Synthesis of 3-amino-N-(2,2,2-trifluoroethyl)-3,8-diazabicyclo[3.2.1]octane-8-carboxamide

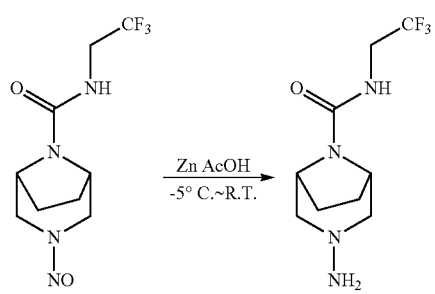

3-nitroso-N-(2,2,2-trifluoroethyl)-3,8-diazabicyclo[3.2.1]octane-8-carboxamide (2.66 g, 10.00 mmoL) was dissolved in 20 mL of methanol at room temperature, Zn (2.64 g, 40.00 moL) was added and cooled to −5° C., and glacial acetic acid (10 mL) was slowly and dropwise added. After the addition was complete, stirring was carried out for 0.5 h at 0° C. and the reaction was naturally warmed to room temperature, and reacted for 16 h. The reaction was filtered, the filter cake was rinsed with methanol, and the filtrate was evaporated to dryness under reduced pressure. 50 mL of water was added for dissolution. The solution was adjusted with sodium carbonate to pH 9, and extracted five times with a mixed solvent of DCM/MeOH (5:1). The organic phases were combined, washed with saturated brine, dried with anhydrous sodium sulfate, and evaporated to dryness under reduced pressure, to obtain 2.41 g of a light-yellow oily substance, with a yield of 95%.

Step 3: Synthesis of 4-(8-(2,2,2-trifluoroethylcarbamoyl)-3,8-diazabicyclo[3.2.1]octane-3-amino)-1H-7-azaindole-5-carboxamide 4-(8-(2,2,2-trifluoroethylcarbamoyl)-3,8-diazabicyclo[3.2.1]octane-3-amino)-1H-7-azaindole-5-carboxamide was prepared with reference to the method in Step 5 of Example 2, by replacing (S)-1-amino-N-(2,2-difluoroethyl)piperidine-3-carboxamide hydrochloride with 3-amino-N-(2,2,2-trifluoroethyl)-3,8-diazabicyclo[3.2.1]octane-8-carboxamide.

$^{1}$H NMR (400 MHz, Methanol-d$_{4}$) δ 8.35 (s, 1H), 7.38 (d, J=3.5 Hz, 1H), 7.10 (d, 0.1=3.5 Hz, 1H), 3.92 (m, 2H), 3.89-3.81 (m, 2H), 3.51 (m, 2H), 3.40 (m, 2H), 2.21 (m, 2H), 1.83 (m, 2H). MS (ESI) m/z: 412 [M+H]$^{+}$.

Example 18

Synthesis of 4-(8-(2,2,2-trifluoroacetyl)-3,8-diazabicyclo[3.2.1]octane-3-amino)-1H-7-azaindole-5-carboxamide

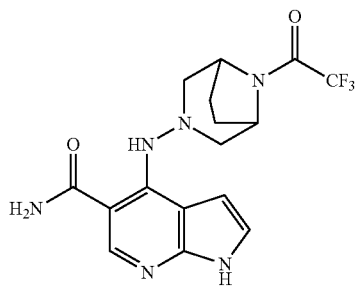 [SMILES: NC(=O)c1cnc2[nH]ccc2c1NN1CC2CCC(C1)N2C(=O)C(F)(F)F]

Step 1: Synthesis of tert-butyl 8-nitroso-3,8-diazabicyclo[3.2.1]octane-3-carboxylate

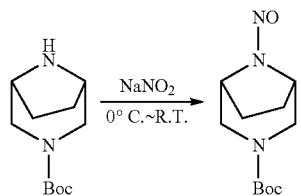

8-Boc-3,8-diazabicyclo[3.2.]octane (1.06 g, 5.00 mmoL) was added into a mixed solvent of 20 mL of glacial acetic acid and 5 ml of water and cooled to 0° C., and then 10 ml of an aqueous solution with dissolved sodium nitrite (0.52 g, 15.00 mmoL) was dropwise added. The stirring was carried out for 1 h at 0° C., and the reaction was naturally warmed to room temperature, and reacted for 2 h. The reaction was added with water, and extracted three times with ethyl acetate. The organic phases were combined, washed with saturated brine, evaporated to dryness under reduced pressure, to obtain 1.21 g of a crude product, which was directly applied to the next step.

Step 2: Synthesis of tert-butyl 8-amino-3,8-diazabicyclo[3.2.1]octane-3-carboxylate

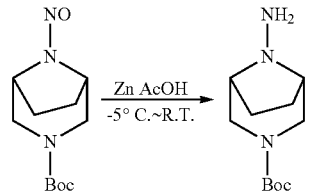

Tert-butyl 8-nitroso-3,8-diazabicyclo[3.2.1]octane-3-carboxylate (1.21 g, 5.00 mmoL) was dissolved in a four-neck flask containing 20 mL of methanol, Zn powder (1.30 g, 20.00 moL) was added and cooled to −5° C. and 10 mL of glacial acetic acid was slowly and dropwise added. After the addition was complete, stirring was carried out for 0.5 h at 0° C., and the reaction was naturally warmed to room temperature, and reacted for 2 h. The reaction was filtered, the filter cake was rinsed with methanol, and the filtrate was evaporated under reduced pressure to remove the solvent, to obtain 1.14 g of a light-yellow viscous and thick liquid, with a yield of 99%.

Step 3: Synthesis of 4-(8-(2,2,2-trifluoroacetyl)-3,8-diazabicyclo[3.2.1]octane-3-amino)-1H-7-azaindole-5-carboxamide With reference to the method in Step 7 of Example 1, ethyl (S)-1-aminopiperidine-3-carboxylate hydrochloride in Step 7 of Example 1 was replaced with tert-butyl 8-amino-3,8-di azabicyclo[3.2.1]octane-3-carboxylate, and then deprotection and acylation were performed to obtain 4-(8-(2,2,2-trifluoroacetyl)-3,8-diazabicyclo[3.2.1]octane-3-amino)-1H-7-azaindole-5-carb oxamide.

$^{1}$H NMR (400 MHz, Methanol-d$_{4}$) δ 8.53 (s, 1H), 7.38 (d, J=3.5 Hz, 1H), 7.32 (d, J=1.8 Hz, 1H), 4.25 (m, 2H), 3.42 (m, 2H), 3.14 (m, 2H), 2.47 (m, 2H), 2.30 (m, 2H). MS (ESI) m/z: 383 [M+H]$^{+}$.

Example 19

Synthesis of 4-(4-(2,2,2-trifluoroethylcarbamoyl)piperidine-1-amino)-1H-7-azaindole-5-carboxamide

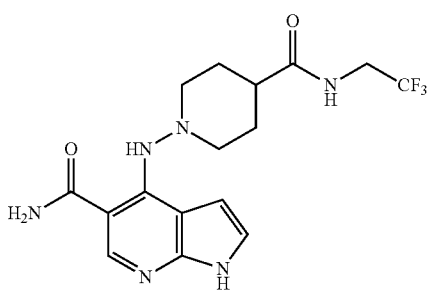 [SMILES: NC(=O)c1cnc2[nH]ccc2c1NN1CCC(C(=O)NCC(F)(F)F)CC1]

Step 1: Synthesis of 1-nitroso-N-(2,2,2-trifluoroethyl)piperidine-4-carboxamide

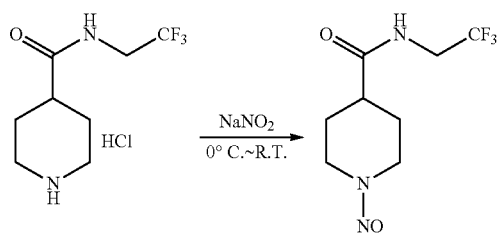

N-(2,2,2-trifluoroethyl)piperidine-4-carboxamide hydrochloride (2.10 g, 10.00 mmoL) was added into a mixed solvent of 20 mL of glacial acetic acid and 5 ml of water and cooled to 0° C. and then 5 ml of an aqueous solution with dissolved sodium nitrite (1.04 g, 15.00 mmoL) was dropwise added. The stirring was carried out for 1 h at 0° C., and the reaction was naturally warmed to room temperature, and reacted for 2 h. The reaction was added with water, and extracted three times with ethyl acetate. The organic phases were combined, washed with saturated brine, and evaporated to dryness under reduced pressure, to obtain 2.39 g of a light-yellow solid, which was directly applied to the next-step reaction.

Step 2: Synthesis of 1-amino-N-(2,2,2-trifluoroethyl)piperidine-4-carboxamide hydrochloride

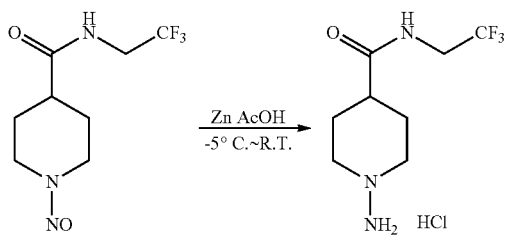

1-nitroso-N-(2,2,2-trifluoroethyl)piperidine-4-carboxamide (2.39 g, 10.00 mmoL) was dissolved in 20 mL of methanol, Zn powder (2.64 g, 40.00 moL) was added and cooled to −5° C. and 10 mL of glacial acetic acid was slowly and dropwise added. After the addition was complete, stirring was carried out for 0.5 h at 0° C., and the reaction was naturally warmed to room temperature, and reacted for 2 h. The reaction was filtered, the filter cake was rinsed with methanol and the filtrate was evaporated to dryness under reduced pressure. 10 mL of a solution of hydrochloric acid in ethanol was added into the residue, and stirred for 10 min. It was evaporated to dryness under reduced pressure, to obtain 2.61 g of a light-yellow viscous and thick liquid, with a yield of 100%.

Step 3: Synthesis of 4-(4-(2,2,2-trifluoroethylcarbamoyl)piperidine-1-amino)-1H-7-azaindole-5-carboxamide 4-(4-(2,2,2-trifluoroethylcarbamoyl)piperidine-1-amino)-1H-7-azaindole-5-carboxamide was prepared with reference to the method in Step 5 of Example 2, by replacing (S)-1-amino-N-(2,2-difluoroethyl)piperidine-3-carboxamide hydrochloride with 1-amino-N-(2,2,2-trifluoroethyl) piperidine-4-carboxamide hydrochloride.

$^1$H NMR (400 MHz, DMSO-$d_6$) δ 11.41 (br, 1H), 9.95 (br, 1H), 8.59 (br, 1H), 8.37 (s, 1H), 7.83 (br, 1H), 7.08-7.03 (m, 3H), 3.88 (br, 2H), 3.10 (m, 2H), 2.71 (m, 1H), 2.42 (m, 2H), 1.80 (m, 2H), 1.69 (m, 1H), 1.36 (m, 1H). MS (ESI) m/z: 385 [M+H]$^+$.

Example 20

Synthesis of (S)-4-(3-(3,3-difluorocyclobutylcarbamoyl)piperidine-1-amino)-1H-7-azaindole-5-carboxamide

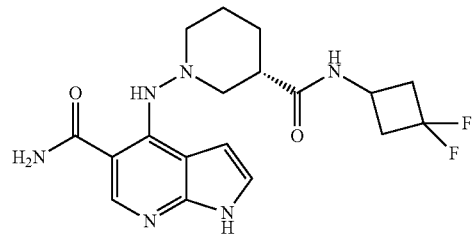 [SMILES: NC(=O)c1cnc2[nH]ccc2c1NN1CCC[C@H](C(=O)NC2CC(F)(F)C2)C1]

Step 1: Synthesis of (S)—N-(3,3-difluorocyclobutyl)-1-nitrosopiperidine-3-carboxamide

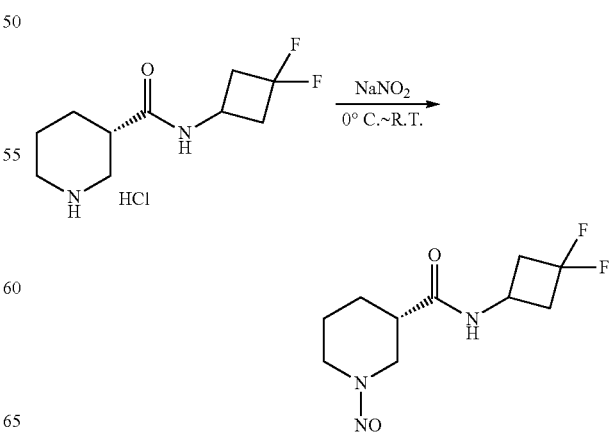

(S)—N-(3,3-difluorocyclobutyl)piperidine-3-carboxamide hydrochloride (2.18 g, 10.00 mmoL) was added into a mixed solvent of 20 mL of glacial acetic acid and 5 ml of water and cooled to 0° C., and then 5 ml of an aqueous solution with dissolved sodium nitrite (1.04 g, 15.00 mmoL) was dropwise added. The stirring was carried out for 1 h at 0° C. and the reaction was naturally warmed to room temperature, and reacted for 2 h. The reaction was added with water, and extracted three times with ethyl acetate. The organic phases were combined, washed with saturated brine, and evaporated to dryness under reduced pressure, to obtain 2.47 g of a light-yellow solid which was directly applied to the next-step reaction, with a yield of 100%.

Step 2: Synthesis of (S)—N-(3,3-difluorocyclobutyl)-1-nitrosopiperidine-3-carboxamide hydrochloride

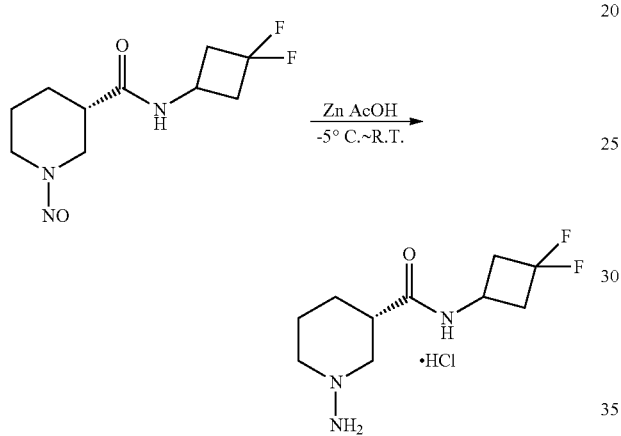

1-nitroso-N-(2,2,2-trifluoroethyl)piperidine-4-carboxamide (2.47 g, 10.00 mmoL) was dissolved in 20 mL of methanol, Zn powder (2.64 g, 40.00 moL) was added and cooled to −5° C., and 10 mL of glacial acetic acid was slowly and dropwise added. After the addition was complete, stirring was carried out for 0.5 h at 0° C., and the reaction was naturally warmed to room temperature, and reacted for 2 h. The reaction was filtered, the filter cake was rinsed with methanol and the filtrate was evaporated to dryness under reduced pressure. 10 mL of a solution of hydrochloric acid in ethanol was added into the residue, and stirred for 10 min. It was evaporated to dryness under reduced pressure, to obtain 2.69 g of a light-yellow viscous and thick liquid, with a yield of 100%.

Step 3: Synthesis of (S)-4-(3-(3,3-difluorocyclobutylcarbamoyl)piperidine-1-amino)-1H-7-azaindole-5-carboxamide (S)-4-(3-(3,3-difluorocyclobutylcarbamoyl)piperidine-1-amino)-1H-7-azaindole-5-carboxamide was prepared with reference to the method in Step 5 of Example 2, by replacing (S)-1-amino-N-(2,2-difluoroethyl)piperidine-3-carboxamide hydrochloride with (S)—N-(3,3-difluorocyclobutyl)-1-nitrosopiperidine-3-carboxamide hydrochloride.

$^1$H NMR (400 MHz, Methanol-$d_4$) δ 8.32 (s, 1H), 7.18 (br, 1H), 7.07 (d, J=2.4 Hz, 1H), 4.12 (m, 1H), 2.90 (m, 2H), 2.74 (m, 1H), 2.54 (m, 4H), 2.22 (t, J=7.3 Hz, 1H), 2.06 (m, 1H), 1.86 (m, 3H), 1.62 (m, 1H). MS (ESI) m/z: 393 [M+H]$^+$.

Example 21

Synthesis of ethyl (S)-1-(5-cyano-1H-7-azaindole-4-amino)piperidine-3-carboxylate

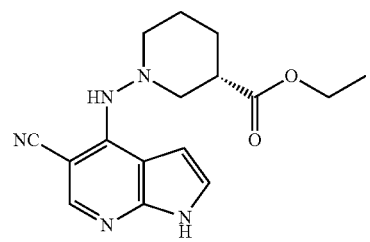 [SMILES: CCOC(=O)[C@H]1CCCN(Nc2c(C#N)cnc3[nH]ccc23)C1]

Step 1: Synthesis of 4-chloro-1-(triisopropylsilyl)-1H-pyrrolo[2,3-b]pyridine-5-carbonitrile

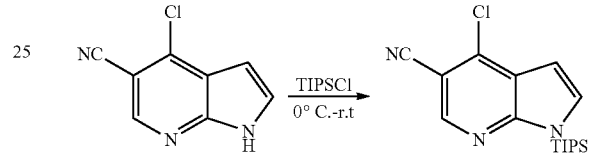

4-chloro-1H-pyrrolo[2,3-b]pyridine-5-carbonitrile (1.00 g, 5.60 mmol) was dissolved in DMF (10 mL) under nitrogen protection, NaH (0.27 g, 11.20 mmol) was added at 0° C. and the reaction continued with stirring for 20 min. Triisopropylchlorosilane (1.60 g, 8.40 mmol, TIPSCl) was dropwise added, and the reaction continued for 16 h at room temperature and was terminated. It was diluted by adding water, extracted with EA, and the organic phases are combined, dried, concentrated, and purified through column chromatography (EA/PE system) to obtain 1.77 g of a white solid, with a yield of 95%.

Step 2: Synthesis of ethyl (S)-1-(5-cyano-H-7-azaindole-4-amino)piperidine-3-carboxylate

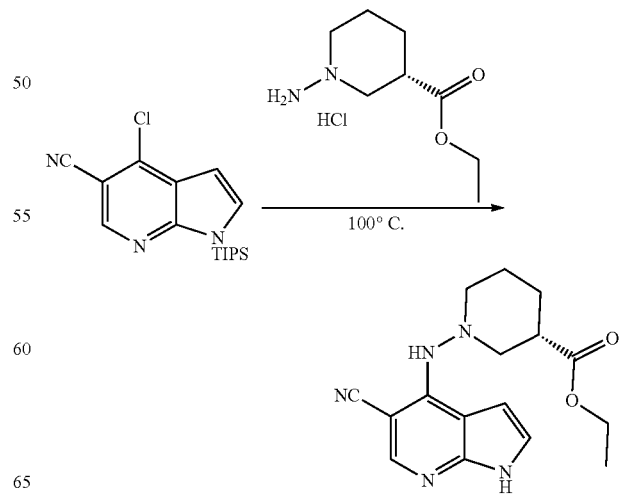

4-chloro-1-(triisopropylsilyl)-1H-pyrrolo[2,3-b]pyridine-5-carbonitrile (0.90 g, 2.69 mmol) was dissolved in 1,4-dioxane (15 mL), triethylamine (0.68 g, 6.72 mmol) and ethyl (S)-1-aminopiperidine-3-carboxylate hydrochloride (0.73 g, 3.50 mmol) were slowly added at room temperature, the temperature was raised to 100° C. under nitrogen protection, and the reaction continued for 24 h. The reaction was concentrated, and purified through column chromatography (EA/PE system on forward column: $H_2O$ (0.1% TFA)/MeCN system on reverse column), to obtain 0.03 g of a light-yellow solid.

$^1$H NMR (300 MHz, DMSO-$d_h$) δ 11.75 (br, 1H), 8.62 (br, 1H), 8.06 (s, 1H), 7.20 (br, 1H), 6.76 (br, 1H), 4.08 (q, J=6.0 Hz, 2H), 3.21 (m, 1H), 3.05 (m, 1H), 2.81 (m, 1H), 2.66 (m, 2H), 1.99 (m, 1H), 1.75 (m, 2H), 1.32 (m, 1H), 1.17 (t, J=7.0 Hz, 3H). MS (ESI) m/z: 314 [M+H]$^+$.

Example 22

Synthesis of (S)-4-((3-((2,2-difluoroethyl)carbamoyl)piperidin-1-yl)amino)-N-methyl-1H-7-pyrrolo[2,3-b]pyridine-5-carboxamide

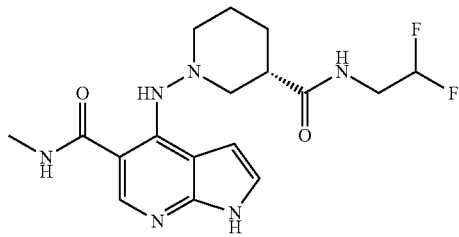 [SMILES: CNC(=O)c1cnc2[nH]ccc2c1NN1CCC[C@H](C(=O)NCC(F)F)C1]

(S)-4-((3-((2,2-difluoroethyl)carbamoyl)piperidin-1-yl)amino)-N-methyl-1H-7-pyrrolo[2,3-b]pyridine-5-carboxamide was synthesized with reference to the preparation method of the compound of Example 1 and the preparation method of the compound of Example 2, by replacing the aqueous solution of ammonia in Step 4 of Example 1 with a solution of methylami ne, and replacing 4-chloro-7-azaindole-5-carboxamide in Step 5 of Example 2 with 4-chloro-N-methyl-1H-pyrrolo[2,3-b]pyridine-5-carboxamide.

$^1$H NMR (400 MHz, DMSO-$d_6$) δ 11.48 (br, 1H), 9.74 (br, 1H), 8.31 (br, 3H), 7.06 (d, J=38.4 Hz, 2H), 5.97 (t, J=56.0 Hz, 1H), 3.56-3.40 (m, 2H), 3.18-3.06 (m, 2H), 2.75 (d, J=4.2 Hz, 3H), 2.68 (t, J=10.9 Hz, 1H), 2.48-2.30 (m, 2H), 1.80 (d, J=12.4 Hz, 2H), 1.73-1.61 (m, 1H), 1.35 (m, 1H): MS (ESI) m/z: 381 [M+H]$^+$.

Example 23

Synthesis of ethyl (S)-4-((3-((2,2,2-trifluoroethyl)carbamoyl)piperidin-1-yl)amino)-1H-pyrrolo[2,3-b]pyridine-5-carboxylate

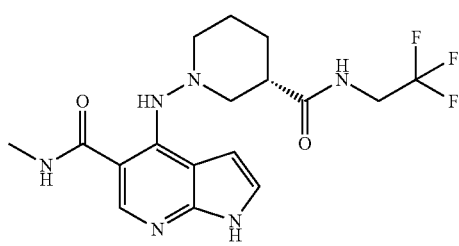 [SMILES: CNC(=O)c1cnc2[nH]ccc2c1NN1CCC[C@H](C(=O)NCC(F)(F)F)C1]

Ethyl (S)-4-((3-((2,2,2-trifluoroethyl)carbamoyl)piperidin-1-yl)amino)-1H-pyrrolo[2,3-b]pyri dine-5-carboxylate was synthesized with reference to the preparation methods of the compounds of Example 1 and Example 22, by replacing the aqueous solution of ammonia in Step 4 of Example 1 with a solution of methylamine.

1H NMR (400 MHz, DMSO-d6) δ 12.49 (br, 1H), 10.53 (br, 1H), 8.73 (br, 1H), 8.63 (br, 1H), 8.40 (br, 1H), 7.33 (br, 1H), 7.21 (br, 1H), 3.89 (dd, J=10.0, 6.7 Hz, 2H), 3.11 (dd, J=24.0, 9.1 Hz, 2H), 2.80 (s, 3H), 2.67 (m, 3H), 1.85 (m, 2H), 1.69 (m, 1H), 1.38 (m, 1H): MS (ESI) m/z: 399 [M+H]$^+$.

Example 24

Kinase Activity Test

This experiment adopted a $\gamma^{33}$p-ATP isotopic test method to test the inhibitory effect of a compound on kinases JAK1, JAK2, JAK3 and TYK2, and obtained a half inhibitory concentration $IC_{50}$ of the compound for inhibiting activity of the kinase.

Tofacitinib was prepared by Jiangsu Vcare Pharmatech Co., Ltd. (batch No.: 321-1-1688-37C), with reference to the method of the patent WO2014195978A2.

1. Basic Reaction Buffer 20 mM 4-hydroxyethylpiperazine ethanesulfonic acid buffer (Hepes, pH 7.5), 10 mM magnesium chloride ($MgCl_2$), 1 mM ethylene glycol diethyl ether diamine tetraacetic acid (EGTA), 0.02% dodecyl polyethylene glycol ether (Brij35), 0.02 mg/ml bovine serum albumin (BSA), 0.1 mM sodium vanadate ($Na_3VO_4$), 2 mM dithiothreitol (DTT), and 1% dimethylsulfoxide (DMSO).

2. Compound Formulation

A compound is dissolved with 100% DMSO to a specific concentration, and then subjected to gradient dilution by an automatic sampling device to obtain the samples to be tested with different concentrations (DMSO solutions).

3. Reaction Steps 3.1 diluting the reaction substrate with the basic reaction buffer;

3.2 adding the kinase into the substrate solution, and gently mixing well;

3.3 adding, by the automatic sampling system, the 100% DMSO diluted compounds with different concentrations into the kinase solution, and incubating for 20 min at room temperature; and 3.4 adding $^{33}$p-ATP (10 μM, 10 μCi/μl) at room temperature to initiate the kinase reaction for a duration of 2 h.

4. Detection

The unreacted ATP and the reaction-generated ADP plasma in the reaction were removed by an ion exchange filtering system, and then the amount of radioactivity of $^{33}$p isotope in the substrate was detected.

5. Data Processing

According to the amount of radioactivity, the kinase activities in the systems added with the inhibitors of different concentrations were calculated, to obtain the inhibitors' effects of the compounds of different concentrations on the kinase activity; and fitting was performed with graphpad prism to obtain the inhibitory $IC_{50}$ values of the compounds.

The biochemical activities of the compounds of the present invention were measured by the above-mentioned test, and the obtained $IC_{50}$ values are shown in Table 1.

TABLE 1

| Compound | Kinase IC$_{50}$ (nM) | | | |
|---|---|---|---|---|
| | JAK1 | JAK2 | JAK3 | TYK2 |
| Example 1 | 0.29 | 2.26 | 2.70 | 3.28 |
| Example 2 | 0.15 | 3.69 | 3.10 | 1.49 |
| Example 3 | 0.41 | 11.6 | 8.69 | 9.93 |
| Example 4 | 34.3 | 522 | 224 | — |
| Example 5 | 1.19 | 54.8 | 15.9 | 34.7 |
| Example 6 | 1.06 | 44.6 | 21.7 | — |
| Example 7 | 0.39 | 1.32 | 0.71 | 1.98 |
| Example 8 | 2.03 | 46.5 | 8.67 | — |
| Example 9 | 0.66 | 42.5 | 7.85 | — |
| Example 10 | 51.9 | — | — | — |
| Example 11 | 11.7 | 211 | 15.5 | — |
| Example 12 | 1.10 | 16.7 | 5.97 | 19.0 |
| Example 14 | 78.3 | — | — | — |
| Example 16 | 1.15 | 41.2 | 9.0 | — |
| Example 19 | 24.0 | 353 | 21.4 | — |
| Example 22 | 35.9 | 137 | 103 | — |
| Example 23 | 0.64 | 18.8 | 6.54 | — |
| WO2016116025 WX14 | 19.7 | 126 | 68.9 | — |
| WO2016116025 WX15 | 17.3 | 297 | 104 | — |
| Tofacitinib | 1.06 | 2.61 | 0.66 | — |

Note:
"—" represents not tested.

The compounds WX14 and WX15 are prepared with reference to the methods of Example 12 and Example 13 of the patent WO2016116025A1, which have the following structures:

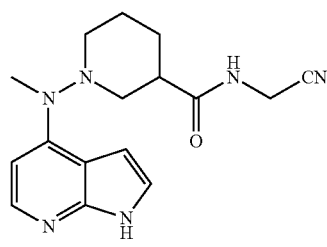

WX14

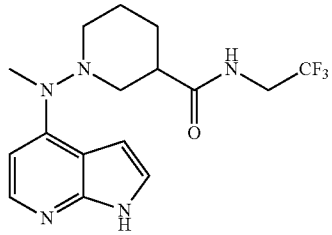

WX15

Conclusion: the compounds of Example 1, Example 2, Example 3, Example 7, Example 9 and Example 23 of the present invention have higher activity in inhibiting the JAK1 kinase than the positive drug control Tofacitinib, and most of the compounds have stronger selectivity in inhibiting the JAK1 kinase than in inhibiting the JAK2 and JAK3 kinases, thereby having a better expectation in safety. The compounds of the present invention also have remarkable inhibitory activity against TYK2, with corresponding anti-inflammatory activity.

Example 25

Liver Microsome Test

In an incubation system with a total volume of 250 μL, an incubation solution of human liver microsomes containing 0.5 mg/mL protein was formulated with a 50 mmol/L PBS buffer (pH=7.4). Before the start of incubation, 2.5 μL of a 100 μmol/L compound to be tested was mixed with 197.5 μL of the above incubation buffer, pre-incubated for 5 min in a 37° C. water bath, and then added with 50 μL of a reducing coenzyme II solution (5 mmol/L) that was likewise pre-incubated for 5 min to start a reaction (in the reaction system, the protein content of liver microsomes from various species was 0.5 g/L, and the final concentration of the compound to be tested was 1 μmol/L), incubated in a 37° C. water bath with shaking, and taken out at 0, 5, 15, 30, and 60 min respectively. 600 μL of a methanol solution of mixed positive and negative internal standards with internal standards Terfenadine (positive ion internal standard, 25 ng/mL) and Tolbutamide (negative ion internal standard, 50 ng/mL) was immediately added to terminate the reaction. The incubation solution after termination was shaken for 2 min and centrifuged (4° C., 16000 r/min) for 10 min, and the supernatant was taken for LC-MS/MS detection to quantitatively analyze the remaining amount of the parent drug. (DMSO=0.1%).

The concentration of the compound at 0 mi incubation was regarded as 100%, and the concentrations at other incubation time points were converted into the remaining percentages. The natural logarithm of the remaining percentage at each time point was linearly regressed against the incubation time, and the slope k was calculated. According to the formula $T_{1/2}=-0.693/k$, the in vitro half-life was calculated. Clearance in liver microsomes (CLint (μL/min/mg protein)=Ln (2)*1000/$T_{1/2}$ (min/Protein Conc (mg/ml)).

TABLE 2

Results of metabolic stability of test substance in human liver microsomes

| Test substance No. | Remaining % (60 min) | $T_{1/2}$ (min) | Clint (μL/min/mg protein) |
|---|---|---|---|
| Example 1 | 59.0 | 81.5 | 17.0 |
| Example 2 | 91.9 | 330.1 | 4.2 |
| Tofacitinib | 80.7 | 198.0 | 7.0 |

Conclusion: the compounds of Example 1 and Example 2 of the present invention have excellent metabolic activity in liver; and in particular, the compound of Example 2 is significantly superior to the positive drug Tofacitinib in terms of the metabolic half-life in liver microsomes, and thus has better in-vivo metabolic stability.

Example 26

Efficacy Test in DSS Induced Mouse Ulcerative Colitis Model

Mice of 6-7 weeks old were randomly grouped, 6 mice per group. Purified water was provided ad libitum to the mice in a negative control group, and a 2% solution of dextran sulfate sodium (DSS) was provided ad libitum to the mice in other groups, for 7 consecutive days. During the modeling, medication was given according to the groups, once a day for 7 days (the treatment groups and the mouse numbers can be adjusted according to the specific situation). Within 8-10 days later, the DSS-containing water was replaced with purified water, provided ad libitum to the mice. The normal administration continued for 3 days.

From the first day of administration, the general conditions such as metal state, eating, drinking and activities of the mice were respectively observed every day, the mice were weighed every day, and the animal stools were collected, evaluated for their traits and subjected to the occult blood test. The disease activity index (DAI) of experimental animals within 1-10 days were comprehensively assessed.

TABLE 3

DAI scoring standards

| Weight loss (%) | Stool trait * | Stool occult blood/gross bloody stool | Score |
|---|---|---|---|
| 0 | normal | normal | 0 |
| 1-5 | | | 1 |
| >5-10 | loose | occult blood positive | 2 |
| >10-15 | | | 3 |
| >15 | thin stool | gross bloody stool | 4 |

* Normal stool: formed stool; loose stool: thick and half-formed stool that is not adhered to the anus; thin stool: watery stool that may be adhered to the anus Scoring was performed according to the above-mentioned standards. The disease activity index (DAI) of each mouse was obtained by summing the scores of weight loss, stool trait and occult blood condition, to evaluate the disease activity. DAI=(score of weight loss+score of stool trait+score of bloody stool)/3, ranging from 0-4.

The experimental data was processed statistically, and the data are all expressed as mean±SD or mean±SME. The SPSS13.0 software was used for statistical analysis, and the differences among the groups were compared with t test (equal variance) or t' test (unequal variance). Assume $\alpha=0.05$, then $P<0.05$ indicates that the difference is statistically significant.

DAI scoring results: the compounds of Example 1 (for the 5 mg/kg group, the DAI sc ore on day 8 is 2.8; for the 15 mg/kg group, the DAI score on day 8 is 2) and Example 2 (for the 5 mg/kg group, the DAI score on day 8 is 1.5) show clear efficacy in the mouse DSS model, and are stronger in efficacy compared to the positive drugs mesalazine (5ASA) (for the 100 mg/kg group, the DAI score on day 8 is 3.5) and Tofacitinib (for the 5 mg/kg group, the DAI score on day 8 is 3.5).

Conclusion: The compounds of Example 1 and Example 2 of the present invention, even at a relatively low dose, show a significant effect in inhibiting the DSS induced enteritis in mice, and have stronger potency than the positive control drug Tofacitinib at the same dose.

Example 27

Test of Evaluating Therapeutic Activity in DNBS (2,4-Dinitrobenzenesulfonic Acid) Induced Rat Crohn's Disease Model Male wistar rats of 4-5 weeks old were adaptively fed for 5 days, and two days before the experiment, randomly divided into 6 groups:

Blank control group: G1 (Normal), 4 normal rats were selected and only given with 30% ethanol, 10 mL/kg.

0.5 mL of 50 mg/mL DNBS (DNBS dissolved in 30% ethanol) was injected into the colon of rats to induce enteritis in rats, for 40 rats in total. Eight of them were selected as model group G2 (Model), and the remaining 32 rats were administrated.

Administration group: the rats with DNBS induced enteritis were administered with ABT494 and the compound of Example 2 respectively and divided into G3-G6 groups, 8 rats/group. G3: ABT494, 10 mg/kg-QD; G4: Example 2, 0.3 mg/kg-BID; G5: Example 2, 1 mg/kg-BID; and G6: Example 2, 3 mg/kg-BID.

The rats were fasted, but fed with water for 48 hours, and a 5% glucose salt solution (10 mL/kg) was used as an energy supplement for experimental animals during the fasting period, once a day. On the day of experimental modeling, the fasting rats were anesthetized with Choutet (25 mg/kg), and then 0.5 mL of 50 mg/mL DNBS was injected from the anus to left colic flexure of the rat (about 8 cm to the anus) to induce rat enteritis. All rats were kept in a heat-down position for 15 min until they were awaken, to prevent the backflow of DNBS. From the day of the experimental modeling, medication was given for 7 days.

The positive drug ABT494 was purchased from Nanjing Xinmeihe Pharmaceutical Technology Co., Ltd. (batch No.; NNES190329), having a structure below:

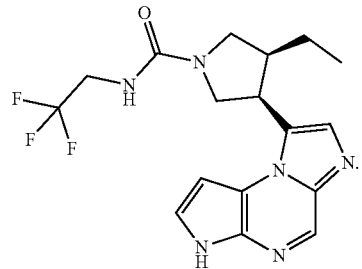 [SMILES: CC[C@@H]1CN(C(=O)NCC(F)(F)F)C[C@@H]1c1cnc2cnc3[nH]ccc3n12]

After the DNBS modeling, the weights of the animals were measured and recorded every day, the daily activities of the animals were observed, and the abnormalities were recorded. During the experiment, the stool state of the rats was scored every day. On day 7, the rats were anesthetized with isoflurane (3-5%), blood was taken from the orbit, and the serum was separated and stored at −80° C. All animals were euthanized by cervical vertebra dis location after suffocation from excessive $CO_2$ inhalation. The abdomen was cut, the colorectum was take out and longitudinally dissected, and the stool trait in the colorectum was scored. The colorectum was thoroughly rinsed with ice-cold PBS and then the ulcer surface was observed. The length and weight and ulcer area of the colon were recorded, the weight-length ratio (colon weight (g)/length (cm) ratio×100) was calculated, and the overall picture was taken. All intestinal tissue was longitudinally divided into two parts, where one part was fixed with 4% neutral PEA and embedded with paraffin, and the rest colon sample was cryopreserved at −80° C.

Excel and Graphapad software were used for statistical analysis, and the results were expressed as mean±SD. Two-tailed T test was used for comparison among groups. *p<0.05 indicates that there is a significant statistical difference between the drug treatment group and the model group, **p<0.01 indicates that there is a very significant statistical difference between the drug treatment group and the model group, *p<0.05 indicates that there is a significant statistical difference between the model group and the normal group, and **p<0.01 indicates that there is a very significant statistical difference between the model group and the normal group.

Figure 25:
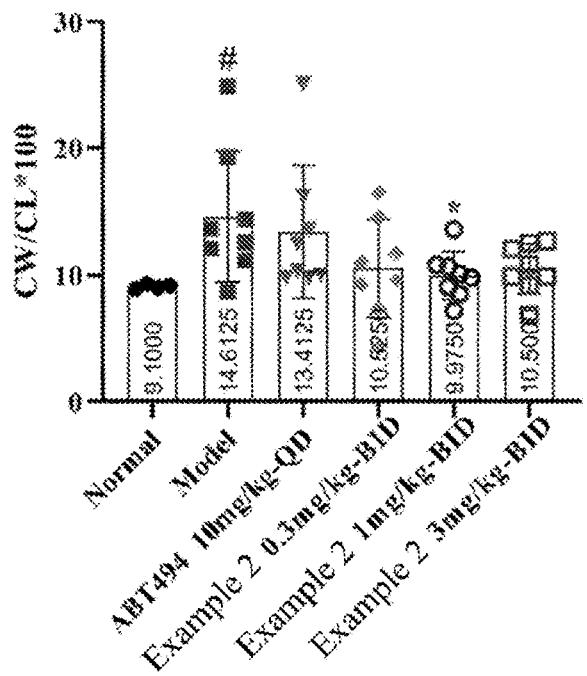
FIG. 25 Results of influence on the colon weight-length ratio in a rat DNBS induced Crohn's disease model.

The results of influence of the compounds on the colon weight-length ratio in the rat DNBS induced Crohn's disease model are shown in FIG. 25, and the colon pictures are shown in FIGS. 27-33, where the colon weight-length ratios of the drug treatment groups G3: ABT494 10 mg/kg-QD, G4: Example 2 0.3 mg/kg-BID, G5: Example 2 1 mg/kg-BID and G6: Example 2 3 mg/kg-BID, are 13.4±5.2, 10.5±3.9, 10.0±1.9 and 10.5±2.0 respectively, which are all lower than the colon weight-length ratio (14.6±5.1) of the model group G2, and the comparison between the G5 Example 2 1 mg/kg-BID group and the model groupG2 shows a significant difference (*p<0.05).

Figure 26:
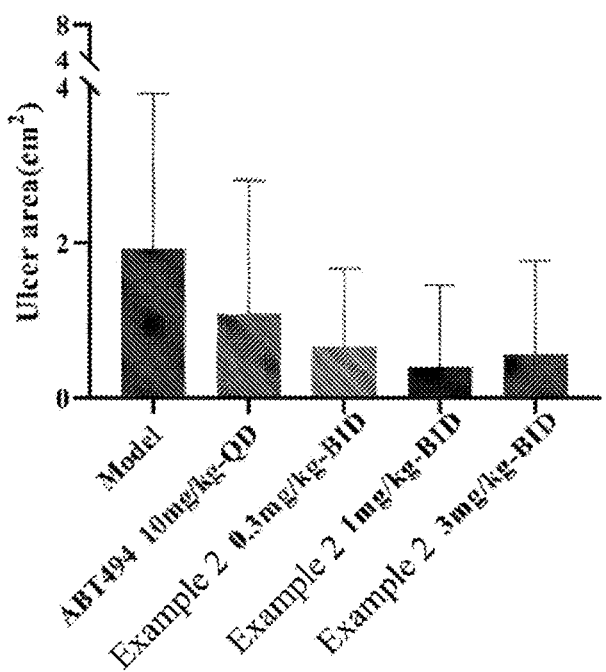
FIG. 26 Rat colon ulcer area in a rat DNBS induced Crohn's disease model.
Figure 27:
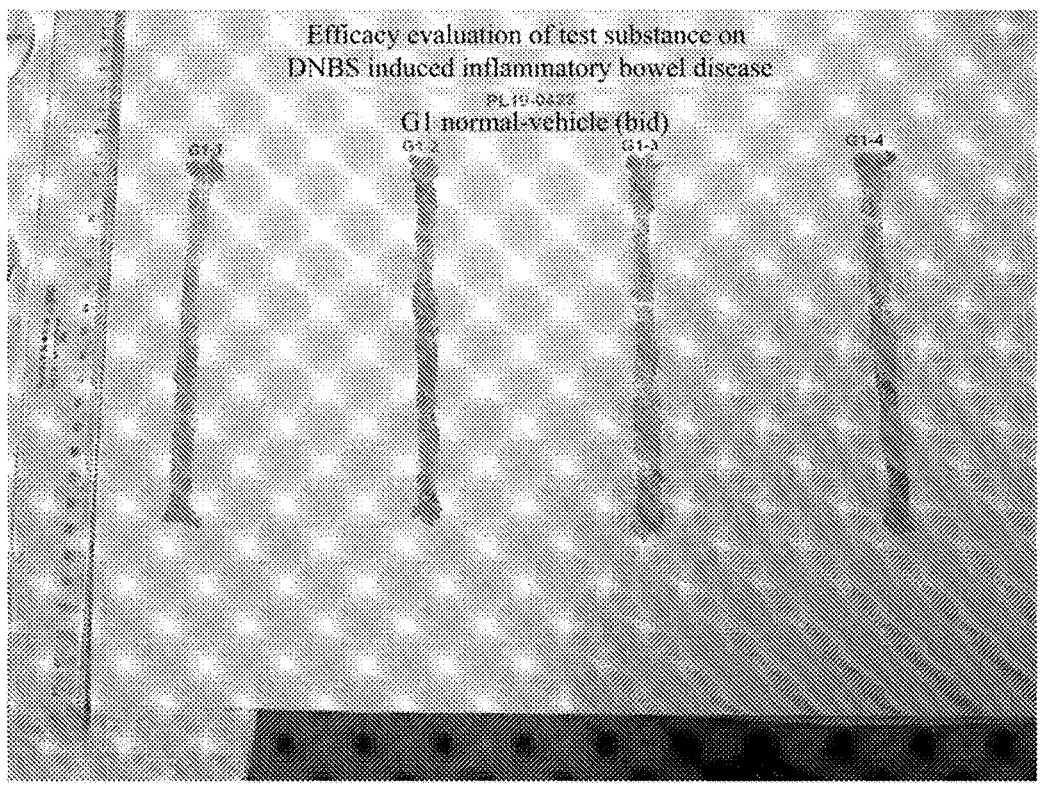
FIG. 27 Colon pictures of rats in group G1.
Figure 28:
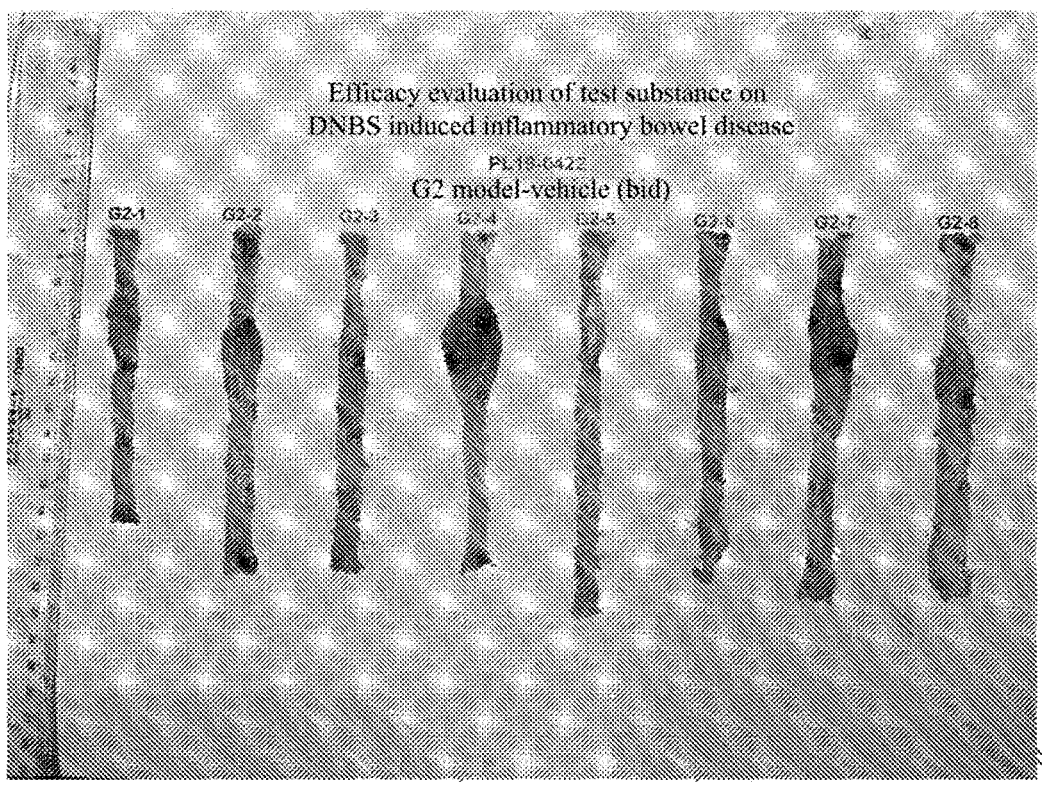
FIG. 28 Colon pictures of rats in group G2.
Figure 29:
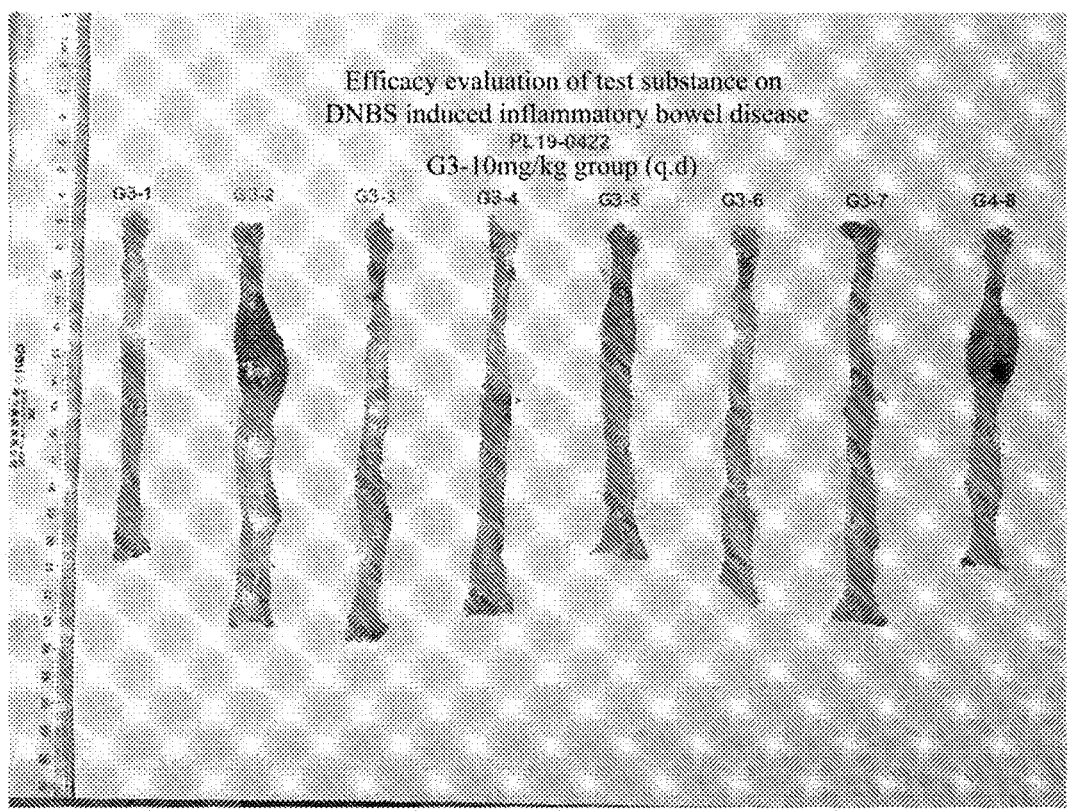
FIG. 29 Colon pictures of rats in group G3.
Figure 30:
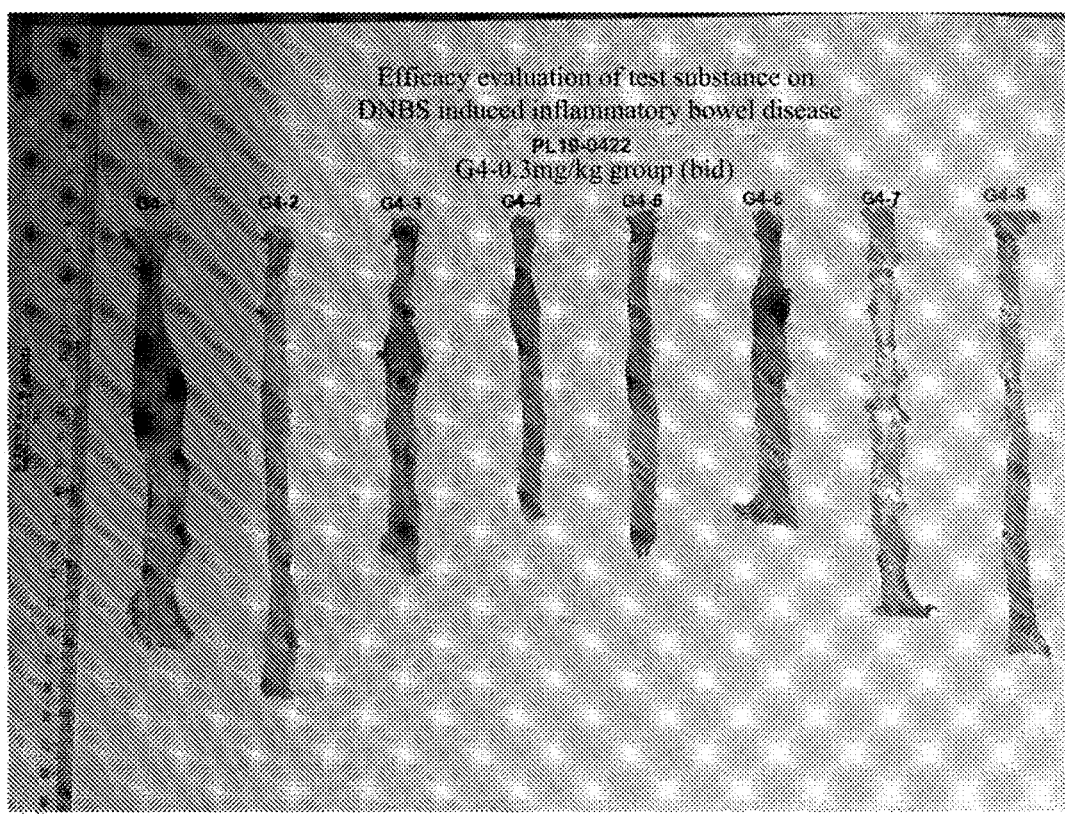
FIG. 30 Colon pictures of rats in group G4.
Figure 31:
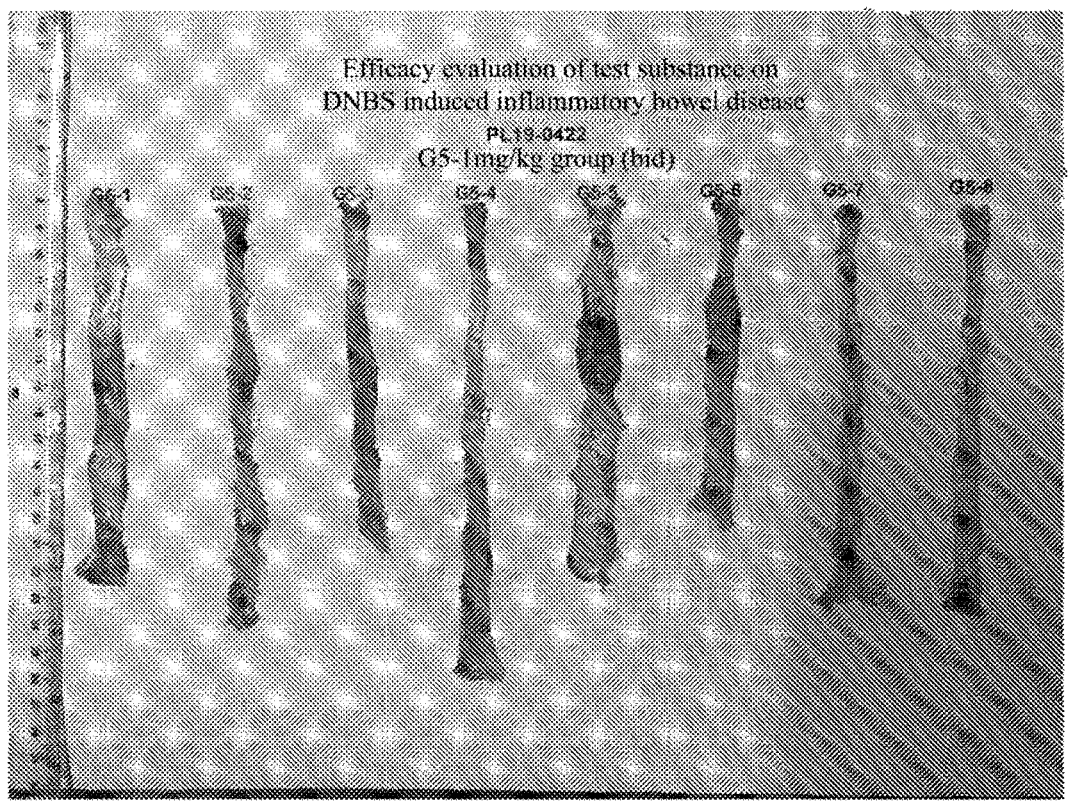
FIG. 31 Colon pictures of rats in group G5.
Figure 32:
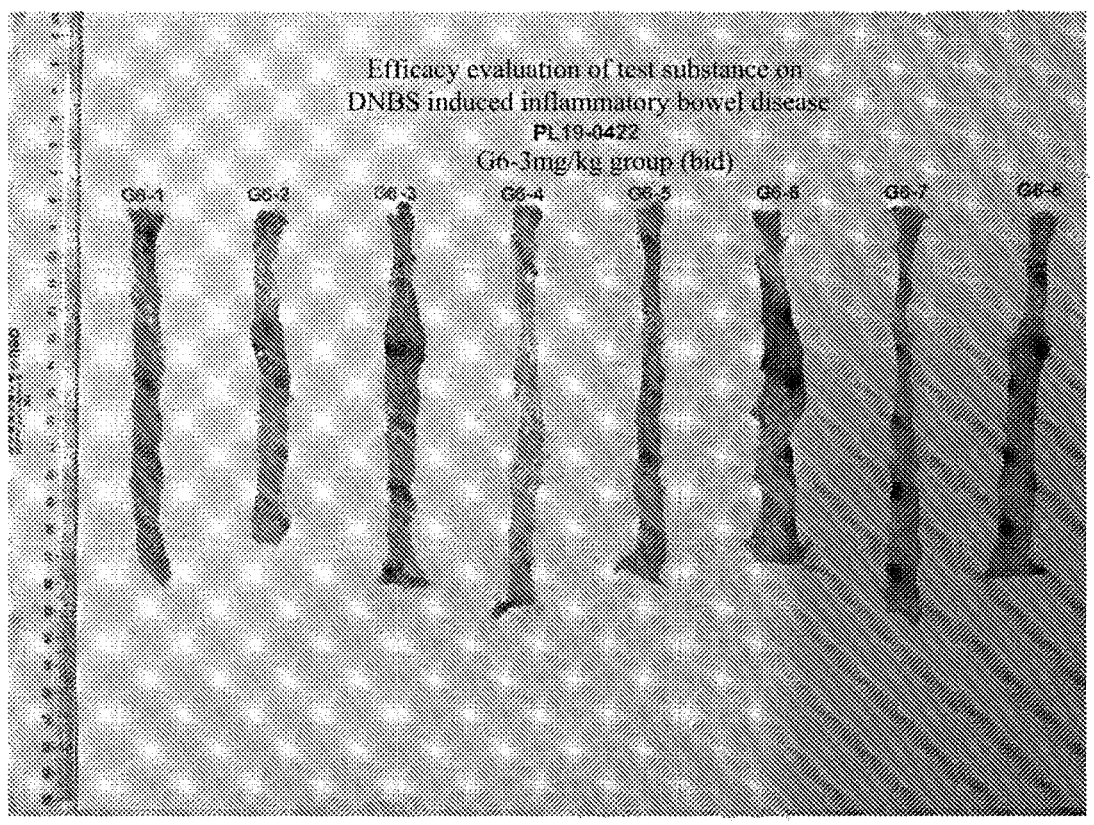
FIG. 32 Colon pictures of rats in group G6.
Figure 33:
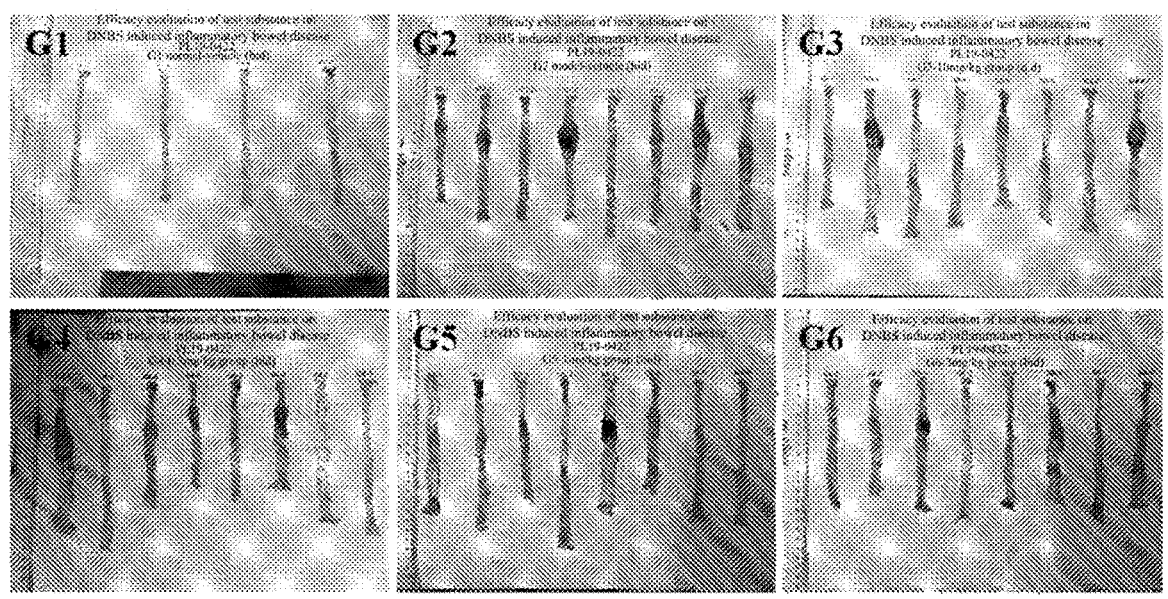
FIG. 33 Comparison of the zoomed-out colon pictures of rats in groups G1-G6.

The influence of the compounds on the colon ulcer area in the rat DNBS induced Crohn's disease model is shown in FIG. 26, where the rat colon ulcer areas of the drug treatment groups G3: ABT494 10 mg/kg-QD, G4: Example 2 0.3 mg/kg-BID, G5: Example 2 1 mg/kg-BID and G6: Example 2 3 mg/kg-BID, are 1.37±1.72, 0.83±1.00, 0.65±1.05 and 0.76±1.21 respectively, which are all lower than the rat colon ulcer area (1.54±2.00) of the model group G2.

Conclusion: the compound of Example 2 of the present invention, even at a relatively low dose, shows a significant effect in inhibiting the DNBS induced enteritis of the rats.

The invention claimed is:

1. A compound of formula (I) and a stereoisomer thereof or a pharmaceutically acceptable salt thereof:

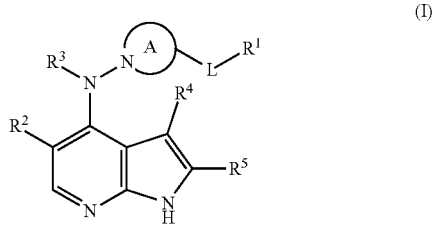

(I)

wherein the ring A is selected from optionally substituted 4-12-membered heterocyclyl or 5-10-membered heteroaryl;

$R^1$ is selected from H, hydroxyl, optionally substituted $C_1$-$C_8$alkyl, $C_3$-$C_8$ cycloalkyl, $C_2$-$C_8$ alkenyl, $C_2$-$C_8$ alkynyl, 4-12-membered heterocyclyl, 6-10-membered aryl or 5-10-membered heteroaryl;

$R^2$ is selected from cyano, —C=ONR$^6$R$^7$, —C=ONR$^6$NR$^7$R$^8$, —C=ONHOR$^6$, —S(O)$_m$R$^8$, —S(O)$_m$—NHR$^8$ or —C=OOR$^6$;

L is selected from amino, —NR$^6$C=O—, —NR$^6$C=ONR$^{10}$—, —C=ONR$^{10}$, —C=ONR$^6$O—, —C=ONR$^6$NR$^{10}$—, —NR$^6$S(O)$_m$—, —S(O)$_m$NR$^6$—, —NR$^6$S(O)$_m$NR$^7$—, —S(O)$_m$—, —C=O— or —C=OO—;

or L is absent;

$R^3$ is selected from H, optionally substituted $C_1$-$C_8$alkyl, $C_3$-$C_8$ cycloalkyl or —C=OR$^6$;

$R^4$ and $R^5$ are each independently selected from H, deuterium, halogen, cyano, nitro, optionally substituted $C_1$-$C_8$ alkyl, $C_3$-$C_8$ cycloalkyl, 6-10-membered aryl or 5-10-membered heteroaryl;

$R^6$, $R^7$ and $R^{10}$ are each independently selected from H, optionally substituted $C_1$-$C_8$ alkyl or $C_3$-$C_8$ cycloalkyl;

or, $R^{10}$ taken with N and $R^1$ to which it is attached can form an optionally substituted 4-12-membered heterocyclyl;

wherein the substituent groups in the ring A and $R^1$ are each independently selected from one or more of halogen, hydroxyl, cyano, amino, sulfydryl, nitro, $C_1$-$C_8$ alkyl, $C_1$-$C_8$ alkoxy, $C_3$-$C_8$ cycloalkyl, 4-12-membered heterocyclyl, 6-10-membered aryl, 5-10-membered heteroaryl, —(CH$_2$)$_n$C=OOR$^8$, —OC=OR$^8$, —C=OR$^8$, —C=ONR$^8$R$^9$, —NHC=OR$^8$, —NR$^8$R$^9$, —OC—ONR$^8$R$^9$, —NHC=ONR$^8$R$^9$, —S(O)$_m$R$^2$, —S(O)$_m$—NHR$^8$, —NHC=OOR$^8$ or —NHS(O)$_m$R$^3$;

m is selected from 1 or 2;

n is selected from 1, 2, 3, 4 or 5;

$R^8$ and $R^9$ are each independently selected from H, optionally substituted $C_1$-$C_8$ alkyl or $C_3$-$C_8$ cycloalkyl; and the substituent groups in the $R^3$, $R^4$, $R^5$, $R^6$, $R^7$, $R^8$, $R^9$ and $R^{10}$ are each independently selected from one or more of deuterium, halogen, hydroxyl, cyano, amino, sulfydryl, nitro, $C_1$-$C_8$alkyl, $C_1$-$C_8$ alkoxy or $C_3$-$C_8$ cycloalkyl.

2. The compound according to claim 1, wherein the ring A is selected from optionally substituted 4-12-membered heterocyclyl;

$R^1$ is selected from H, hydroxyl, optionally substituted $C_1$-$C_8$alkyl, $C_2$-$C_8$ cycloalkyl, $C_2$-$C_5$ alkenyl, $C_2$-$C_5$ alkynyl, 4-12-membered heterocyclyl, 6-10-membered aryl or 5-10-membered heteroaryl;

$R^2$ is selected from cyano or —C=ONR$^6$R$^7$;

L is selected from amino, —NR$^6$C=O—, —NR$^6$C=ONR$^{10}$—, —C=ONR$^{10}$—, —C=ONR$^6$O—, —C=ONR$^6$NR$^{10}$—, —NR$^6$S(O)$_m$—, —S(O)$_m$NR$^6$—, —NR'S(O)$_m$NR$^7$—, —S(O)—, —C=O— or —C=OO;

or L is absent;

$R^3$ is selected from H, optionally substituted $C_1$-$C_8$ alkyl, $C_3$-$C_8$ cycloalkyl or —C=OR$^6$;

$R^4$ and $R^5$ are each independently selected from H, deuterium, halogen, cyano, nitro, optionally substituted $C_1$-$C_8$ alkyl or $C_3$-$C_8$ cycloalkyl;

$R^6$, $R^7$ and $R^{10}$ are each independently selected from H, optionally substituted $C_1$-$C_8$ alkyl or $C_3$-$C_8$ cycloalkyl;

or, $R^{10}$ taken with N and $R^1$ to which it is attached can form an optionally substituted 4-12-membered heterocyclyl;

wherein the substituent groups in the ring A and $R^1$ are each independently selected from one or more of halogen, hydroxyl, cyano, amino, $C_1$-$C_8$ alkyl, $C_1$-$C_8$alkoxy, $C_3$-$C_8$ cycloalkyl, 4-12-membered heterocyclyl, 6-10-membered aryl, 5-10-membered heteroaryl, —C=ONR$^8$R$^9$, —NHC=OR$^3$—, —NR$^8$R$^9$, —OC=ONR$^8$R$^9$, —NHC—ONR$^8$R$^9$, —S(O)$_m$R$^8$, —S(O)$_m$—NHR$^8$, —NHC=OOR$^8$ or —NHS(O)$_m$R$^8$;

m is selected from 1 or 2;

$R^3$ and $R^9$ are each independently selected from H, optionally substituted $C_1$-$C_8$ alkyl or $C_3$-$C_8$ cycloalkyl; and the substituent groups in the $R^3$, $R^4$, $R^5$, Re, $R^7$, $R^8$, $R^9$ and $R^{10}$ are each independently selected from one or more of deuterium, halogen, hydroxyl, cyano, amino, $C_1$-$C_8$ alkyl, $C_1$-$C_8$ alkoxy or $C_3$-$C_8$ cycloalkyl.

3. The compound according to claim 1 or 2, wherein the ring A is selected from optionally substituted 4-12-membered heterocyclyl;

$R^1$ is selected from H, hydroxyl, optionally substituted $C_1$-$C_8$ alkyl, $C_3$-$C_8$ cycloalkyl, $C_2$-$C_8$ alkenyl, $C_2$-$C_8$ alkynyl, 4-12-membered heterocyclyl, 6-10-membered aryl or 5-10-membered heteroaryl;

$R^2$ is selected from cyano or —C═ONR$^6$R$^7$;

L is selected from amino, —NR$^6$C═O—, —NR$^6$C═ONR$^{10}$—, —C═ONR$^{10}$—, —C═ONR$^{60}$—, —C═ONR$^6$NR$^{10}$—, —NR$^6$S(O)$_m$—, —S(O)$_m$NR$^6$—, —NR$^6$S(O)$_m$NR$^7$—, —S(O)$_m$—, —C═O— or —C═OO—;

or L is absent;

$R^3$ is selected from H or methyl;

$R^4$ and $R^5$ are each independently selected from H, deuterium, halogen, cyano, nitro, optionally substituted $C_1$-$C_8$ alkyl or $C_3$-$C_8$ cycloalkyl;

$R^6$, $R^7$ and $R^{10}$ are each independently selected from H, optionally substituted $C_1$-$C_8$ alkyl or $C_3$-$C_8$ cycloalkyl;

or, $R^{10}$ taken with N and $R^1$ to which it is attached can form an optionally substituted 4-12-membered heterocyclyl;

wherein the substituent groups in the ring A and $R^1$ are each independently selected from one or more of halogen, hydroxyl, cyano, amino, $C_1$-$C_8$ alkyl, $C_1$-$C_8$ alkoxy, $C_3$-$C_8$ cycloalkyl, 4-12-membered heterocyclyl, 6-10-membered aryl, 5-10-membered heteroaryl, —C═ONR$^8$R$^9$, —NHC═OR$^8$, —NR$^8$R$^9$, —OC═ONR$^8$R$^9$, —NHC═ONR$^8$R$^9$, —S(O)$_m$R$^8$, —S(O)$_m$—NHR$^8$, —NHC═OOR$^8$ or —NHS(O)$_m$R$^8$;

m is selected from 1 or 2;

$R^8$ and $R^9$ are each independently selected from H, optionally substituted $C_1$-$C_8$ alkyl or $C_3$-$C_8$ cycloalkyl; and the substituent groups in the $R^4$, R$, $R^6$, $R^7$, $R^8$, $R^9$ and $R^{10}$ are each independently selected from one or more of deuterium, halogen, hydroxyl, cyano, amino, $C_1$-$C_8$ alkyl, $C_1$-$C_8$ alkoxy or $C_3$-$C_8$ cycloalkyl.

4. The compound of claim 3, wherein the ring A is selected from the following optionally substituted groups:

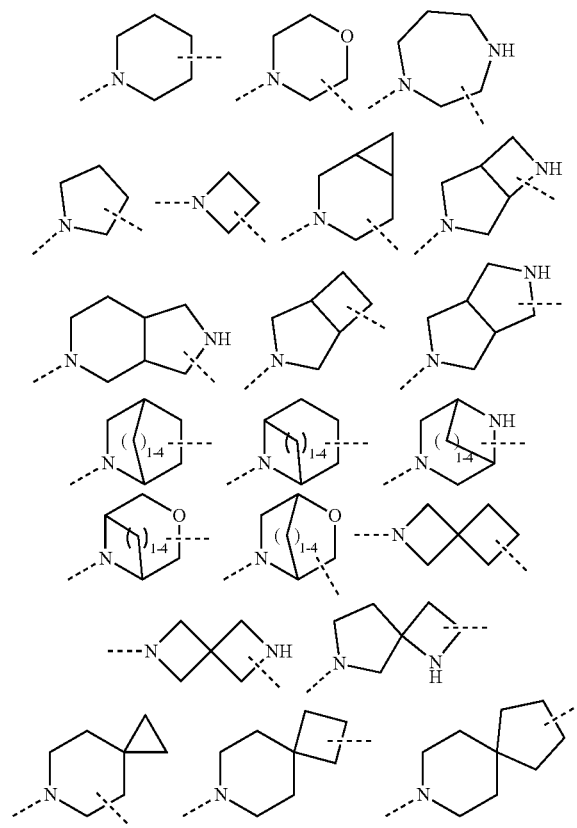

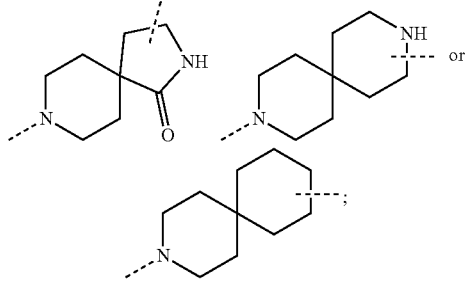

$R^1$ is selected from H, hydroxyl, optionally substituted $C_1$-$C_8$ alkyl, $C_3$-$C_8$ cycloalkyl, 4-12-membered heterocyclyl, 6-10-membered aryl or 5-10-membered heteroaryl;

$R^2$ is selected from cyano or —C═ONR$^6$R$^7$;

L is selected from amino, —NR$^6$C═O—, —NR$^6$C═ONR$^{10}$—, —C═ONR$^{10}$—, —C═ONR$^{60}$—, —C═ONR$^6$NR$^{10}$—, —NR$^6$S(O)$_m$—, —S(O)$_m$NR$^6$—, —NR$^6$S(O)$_m$NR$^7$—, —S(O)$_m$—, —C═O— or —C═OO—;

or L is absent;

$R^3$ is selected from H or methyl;

$R^4$ and $R^5$ are each independently selected from H, deuterium, halogen, cyano, nitro, optionally substituted $C_1$-$C_8$ alkyl or $C_3$-$C_8$ cycloalkyl;

$R^6$, $R^7$ and $R^{10}$ are each independently selected from H, optionally substituted $C_1$-$C_8$ alkyl or $C_3$-$C_8$ cycloalkyl;

or, $R^{10}$ taken with N and $R^1$ to which it is attached can form an optionally substituted 4-12-membered heterocyclyl;

wherein the substituent groups in the ring A and $R^1$ are each independently selected from one or more of halogen, hydroxyl, cyano, amino, $C_1$-$C_8$ alkyl, $C_1$-$C_8$ alkoxy, $C_3$-$C_8$ cycloalkyl, 4-12-membered heterocyclyl, 6-10-membered aryl, 5-10-membered heteroaryl, —C═ONR$^8$R$^9$, —NHC═OR$^8$, —NR$^8$R$^9$, —OC═ONR$^8$R$^9$, —NHC═ONR$^8$R$^9$, —S(O)$_m$R$^8$, —S(O)$_m$—NHR$^8$, —NHC═OOR$^8$ or —NHS(O)$_m$R$^2$;

m is selected from 1 or 2;

$R^8$ and $R^9$ are each independently selected from H, optionally substituted $C_1$-$C_8$ alkyl or $C_3$-$C_8$ cycloalkyl; and the substituent groups in the $R^4$, $R^5$, $R^6$, $R^7$, $R^8$, $R^9$ and $R^{10}$ are each independently selected from one or more of deuterium, halogen, hydroxyl, cyano, amino, $C_1$-$C_8$ alkyl, $C_1$-$C_8$alkoxy or $C_3$-$C_8$ cycloalkyl.

5. The compound of claim 4, wherein the ring A is selected from the following optionally substituted groups:

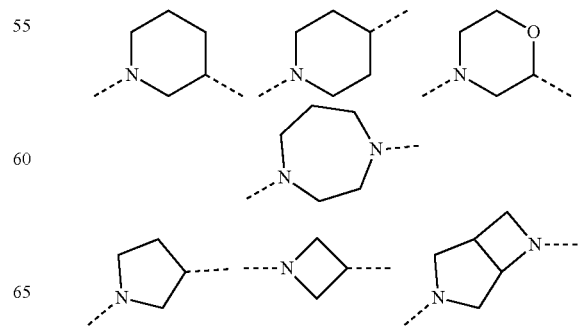

-continued

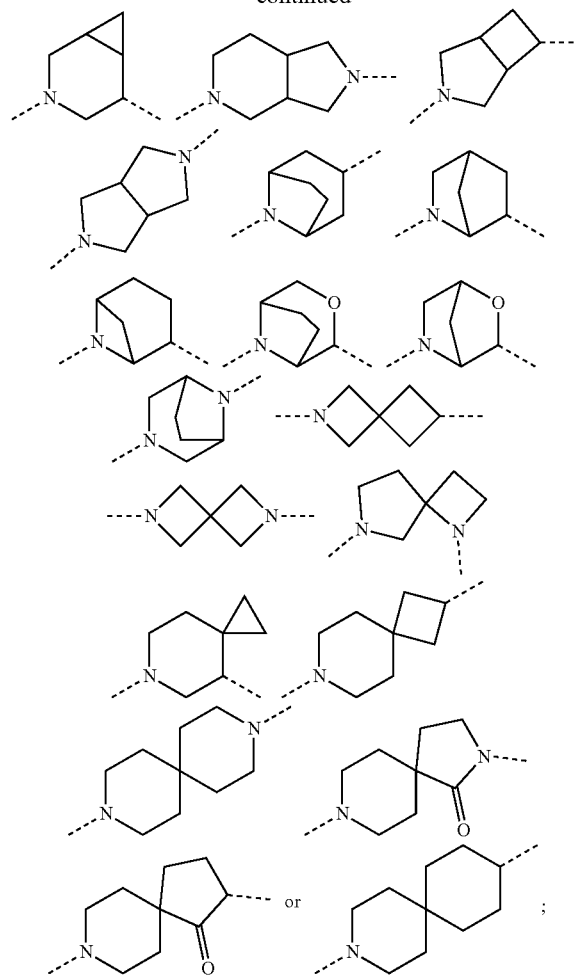

R[1] is selected from H, hydroxyl, optionally substituted methyl, ethyl, propyl, cyclopropyl, n-butyl, tert-butyl, cyclobutyl, phenyl, pyridinyl, imidazolyl, pyrazolyl, oxazolyl, thiazolyl or

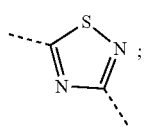;

R[2] is selected from cyano or —C=ONR[6]R[7];
L is selected from amino, —NR[6]C=O—, —NR[6]C=ONR[10]—, —C=ONR[10]—, —C=ONR[60]—, —C=ONR[6]NR[10]—, —NR[6]S(O)$_m$—, —S(O)$_m$NR[6]—, —NR[6]S(O)$_m$NR[7]—, —S(O)$_m$—, —C=O— or —C=OO—;
or L is absent;
R[3] is selected from H or methyl;
R[4] and R[5] are each independently selected from H, deuterium, halogen or cyano;
R[6], R[7] and R[10] are each independently selected from H, optionally substituted Ct-Ca alkyl or $C_3$-$C_8$ cycloalkyl;
or, R[10] taken with N and R[1] to which it is attached can form an optionally substituted 4-12-membered heterocyclyl; and
m is selected from 1 or 2, wherein the substituent groups in the ring A and R[1] are each independently selected from one or more of halogen, hydroxyl, cyano, amino, $C_1$-$C_8$ alkyl, $C_1$-$C_8$ alkoxy, $C_3$-$C_8$ cycloalkyl, 4-12-membered heterocyclyl, 6-10-membered aryl or 5-10-membered heteroaryl;
the substituent groups in the R[6], R[7] and R[10] are each independently selected from one or more of deuterium, halogen, hydroxyl, cyano, amino, $C_1$-$C_8$ alkyl, $C_1$-$C_8$ alkoxy or $C_3$-$C_8$ cycloalkyl.

6. The compound of claim 5, wherein
the ring A is selected from the following optionally substituted groups:

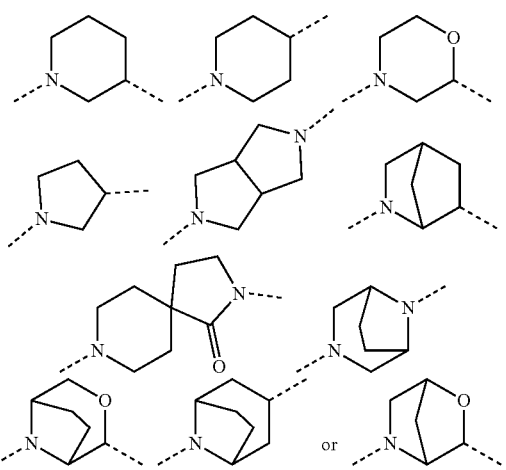

R[1] is selected from H, hydroxyl, optionally substituted methyl, ethyl, propyl, cyclopropyl, n-butyl, tert-butyl, cyclobutyl, phenyl, pyridinyl, imidazolyl, pyrazolyl, oxazolyl, thiazolyl or

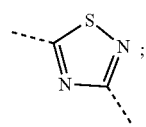;

R[2] is selected from cyano or —C=ONR[6]R[7]:
L is selected from amino, —NR[6]C=O—, —C=ONR[10]—, —S(O)$_m$—, —C=O— or —C=OO—;
or L is absent;
R[3] is selected from H or methyl;
R[4] and R[5] are each independently selected from H, deuterium, F, $C_1$ or cyano;
R[6], R[7] and R[10] are each independently selected from H, optionally substituted $C_1$-$C_8$ alkyl or $C_3$-$C_8$ cycloalkyl;
or, R[10] taken with N and R[1] to which it is attached can form an optionally substituted 4-12-membered heterocyclyl; and
m is selected from 1 or 2,
wherein the substituent groups in the ring A and R[1] are each independently selected from one or more of halogen, hydroxyl, cyano, amino, $C_1$-$C_4$ alkyl or $C_1$-$C_4$ alkoxy;
the substituent groups in the Re, R[7] and R[10] are each independently selected from one or more of deuterium, halogen, hydroxyl, cyano or amino.

7. The compound of claim 6, wherein the ring A is selected from the following optionally substituted groups:

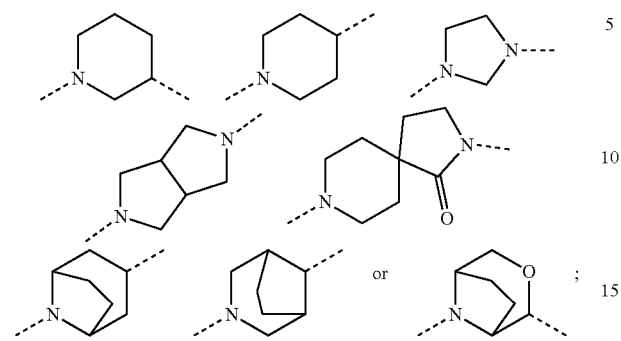

R$^1$ is selected from H, hydroxyl, optionally substituted methyl, ethyl, propyl, cyclopropyl, tert-butyl, cyclobutyl or

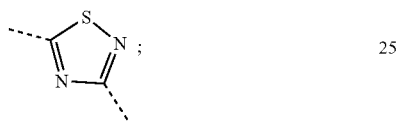

R$^2$ is selected from cyano or —C=ONR$^6$R$^7$;
R$^e$ and R$^7$ are each independently selected from H, methyl or deuterated methyl;
L is selected from —C=ONR$^{10}$—, —S(O)$_m$—, —C=O— or —C=OO—;
or L is absent;
R$^3$ is selected from H or methyl;
R$^4$ and R$^5$ are each independently selected from H or deuterium;
R$^{10}$ is H; and
m is selected from 1 or 2,
wherein the substituent groups in the ring A and R$^1$ are each independently selected from one or more of F, Cl, hydroxyl, cyano, amino, methyl or methoxy.

8. A compound, a stereoisomer thereof or a pharmaceutically acceptable salt thereof, selected from the compounds having the following structures:

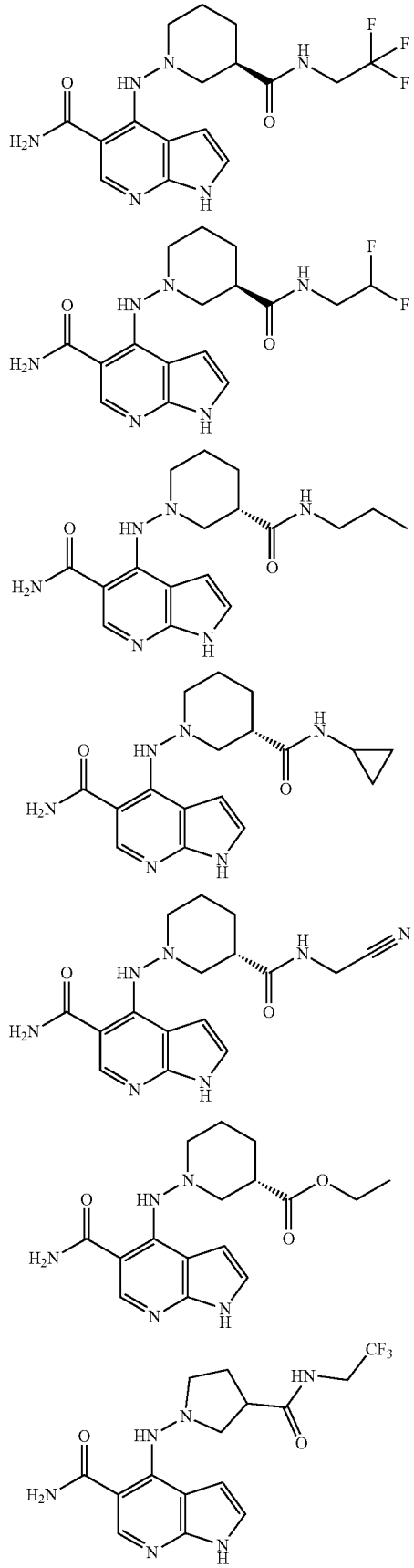

71
-continued
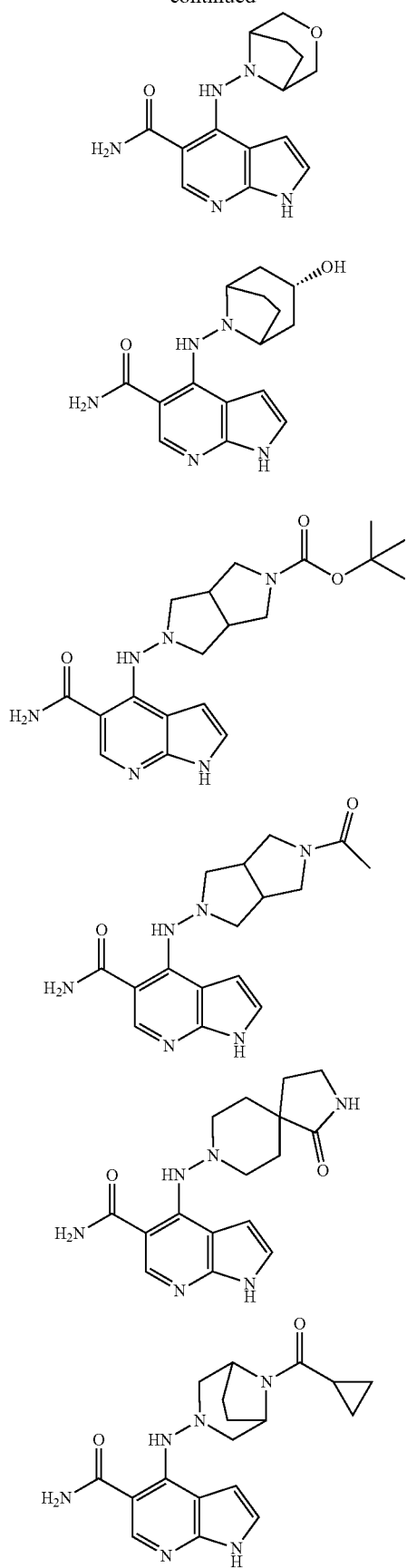
72
-continued
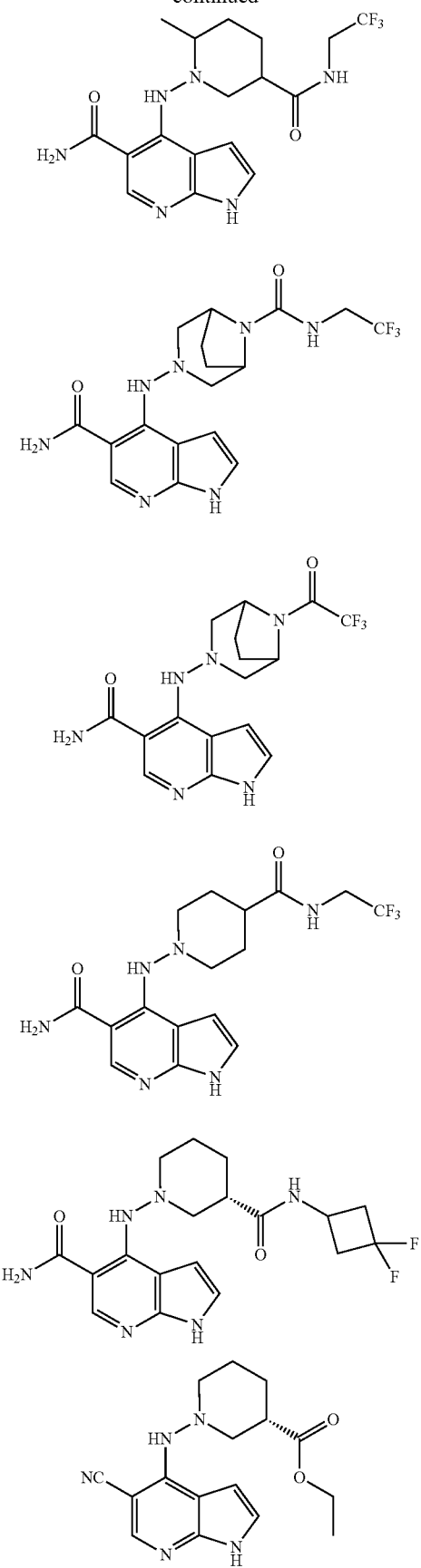

-continued
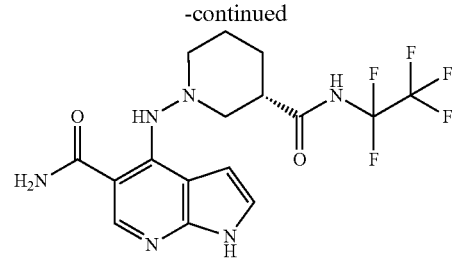
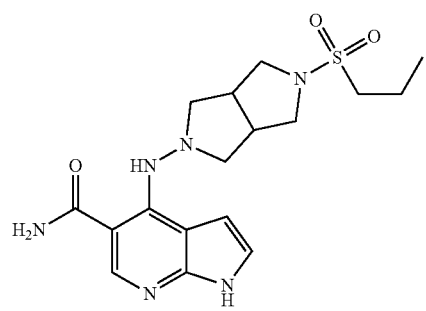
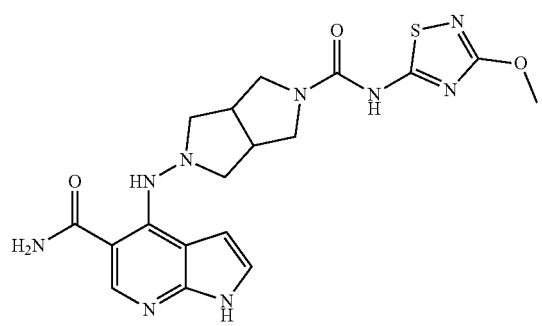
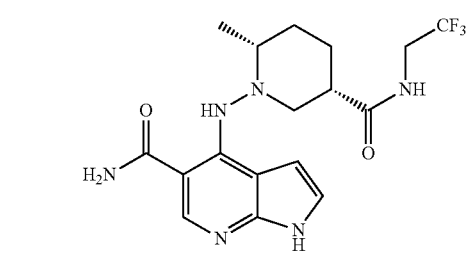
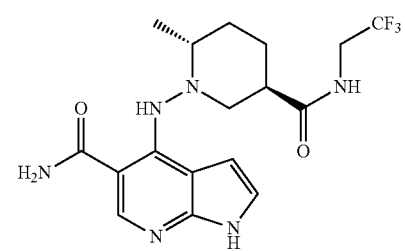
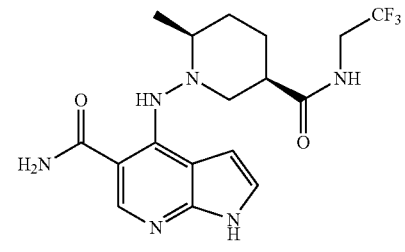
-continued
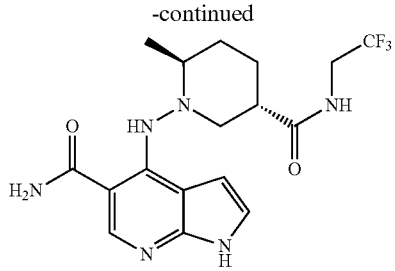
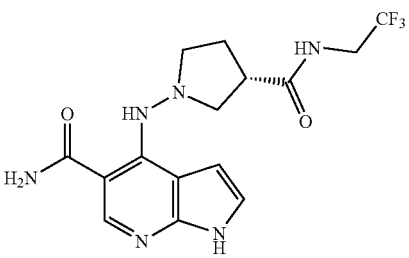
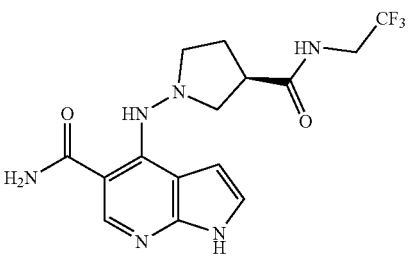
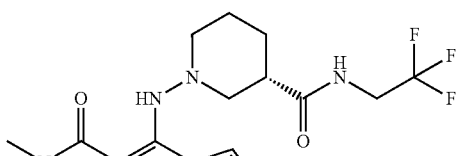
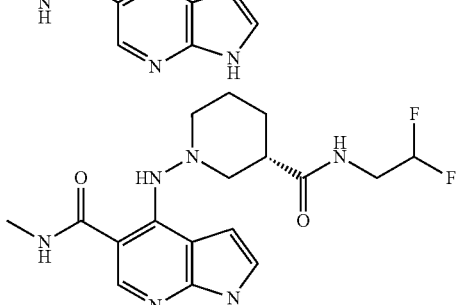
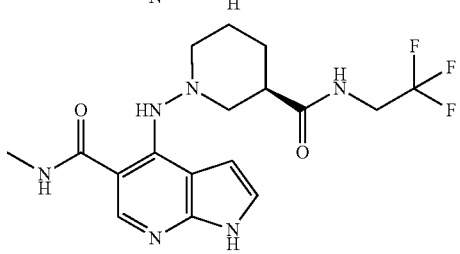
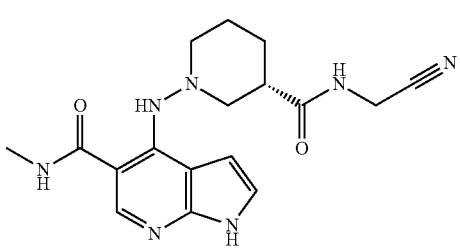

-continued
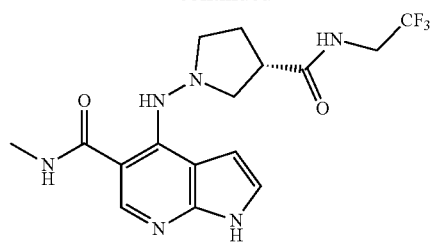
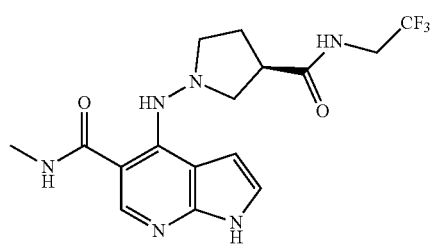
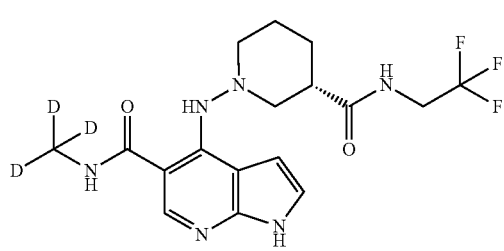
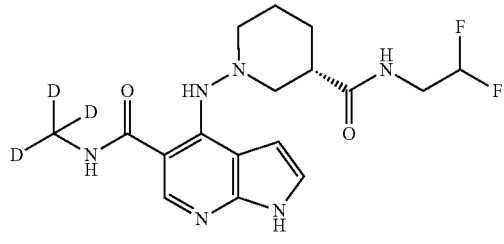
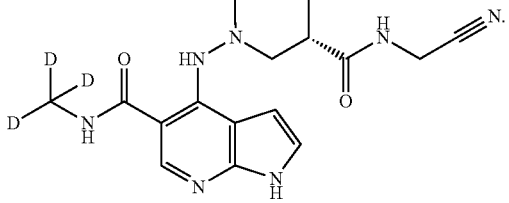
9. A compound, a stereoisomer thereof or a pharmaceutically acceptable salt thereof, selected from the compounds having the following structures:
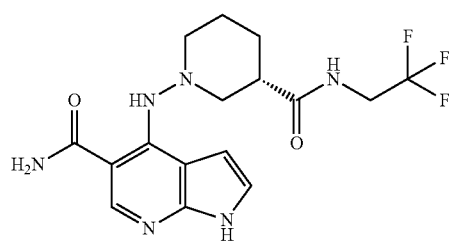
-continued
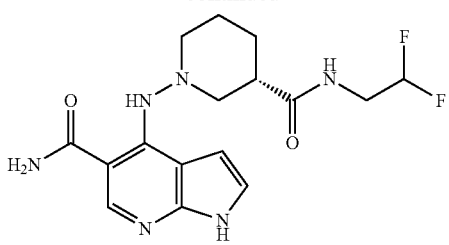
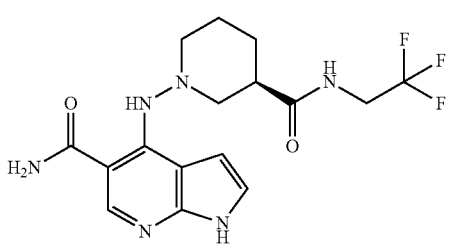
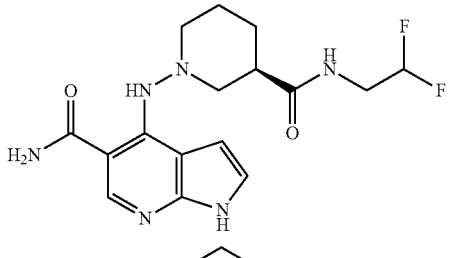
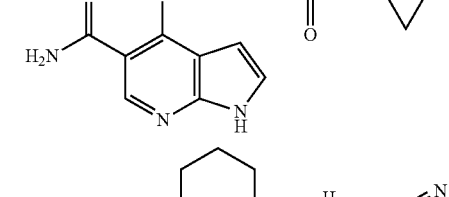
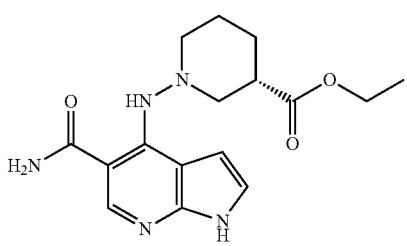

77
-continued
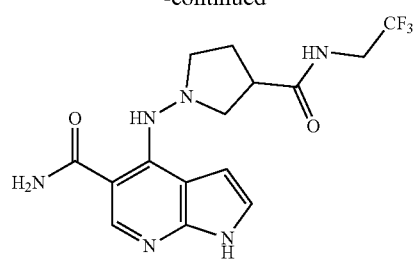
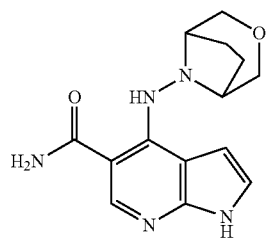
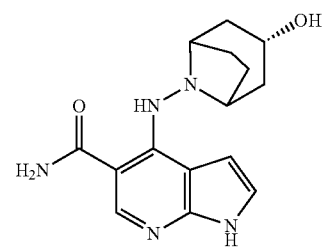
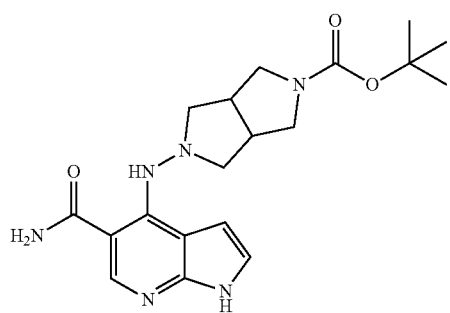
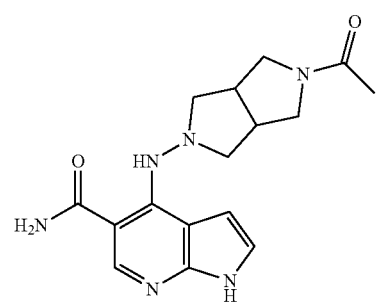
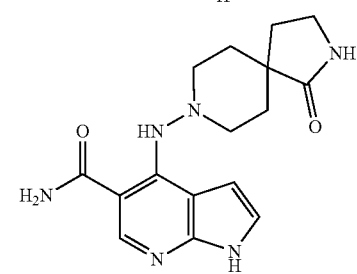
78
-continued
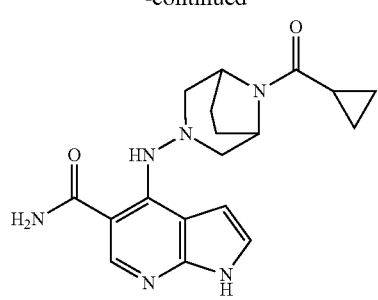
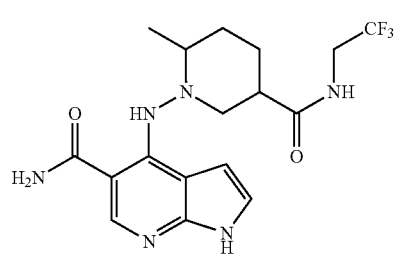
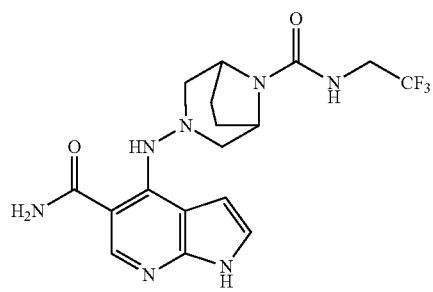
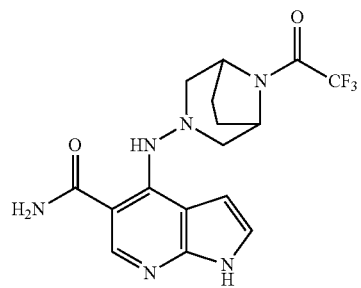
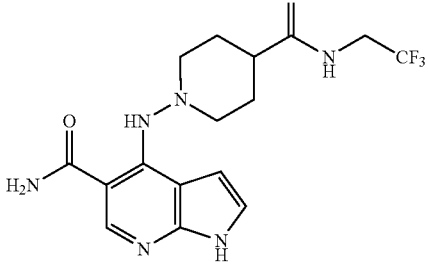
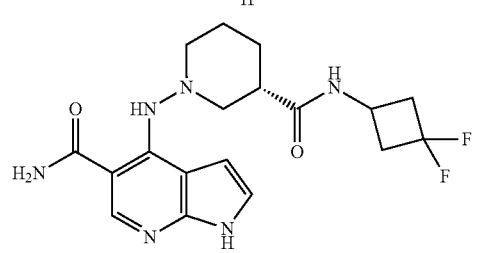

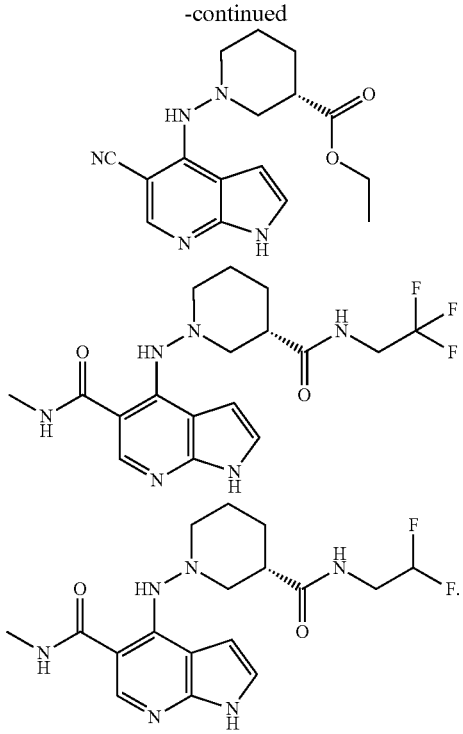

10. A pharmaceutical composition comprising the compound of any one of claims 1-9, a stereoisomer thereof or a pharmaceutically acceptable salt thereof, and a pharmaceutically acceptable carrier.

11. The pharmaceutical composition according to claim 10, selected from capsule, powder, tablet, granule, pill, injection, syrup, oral liquid, inhalant, ointment, suppository or patch.

12. A method for treating a subject for a Janus kinase (JAK) family-mediated disease, the method comprising administering to the subject a compound according to any one of claims 1-9, a stereoisomer thereof or a pharmaceutically acceptable salt thereof, or the pharmaceutical composition according to claim 11.

13. The method according to claim 12, wherein the disease is selected from the group consisting of an immune system disease, an autoimmune disease, a skin disease, an allergic disease, a viral disease, diabetes mellitus type I and diabetic complications, Alzheimer's disease, xerophthalmia, myelofibrosis, thrombocythemia, polycythemia, leukemia and cancer, wherein the immune system disease is organ transplant rejection such as allograft rejection or graft-verse-host disease; the autoimmune disease is selected from systemic lupus erythematosus, multiple sclerosis, rheumatoid arthritis, juvenile arthritis, psoriasis, ulcerative colitis, Crohn's disease and autoimmune thyroid disease; the skin disease is selected from psoriasis, rash, alopecia areata and atopic dermatitis; the allergic disease is selected from asthma and rhinitis; the viral disease is selected from hepatitis B, hepatitis C, chickenpox and herpes zoster virus; the cancer is selected from solid tumor, blood cancer and skin cancer, wherein the solid tumor is selected from prostatic cancer, renal cancer, liver cancer, pancreatic cancer, gastric cancer, breast cancer, lung cancer, head-and-neck cancer, thyroid cancer, glioblastoma and melanoma, the blood cancer is selected from lymphoma and leukemia, and the skin cancer is selected from skin T-cell lymphoma and skin B-cell lymphoma.

* * * * *